US011602550B2

(12) United States Patent
Holzapfel et al.

(10) Patent No.: US 11,602,550 B2
(45) Date of Patent: Mar. 14, 2023

(54) COMPOSITIONS COMPRISING BACTERIAL STRAINS AND USE THEREOF IN CONTROLLING PATHOGENIC MICROORGANISMS

(71) Applicant: Better Air International Limited, Central (HK)

(72) Inventors: Wilhelm H. Holzapfel, Gyung-buk (KR); Yosep Ji, Gyung-buk (KR); Yuli Horesh, Tel-Aviv (IL); Michael Hoffman, Moshav Udim (IL); Shimrit Laor, Netanya (IL)

(73) Assignee: Better Air International Limited, Central (HK)

( * ) Notice: Subject to any disclaimer, the term of this patent is extended or adjusted under 35 U.S.C. 154(b) by 83 days.

(21) Appl. No.: 17/019,596

(22) Filed: Sep. 14, 2020

(65) Prior Publication Data

US 2020/0405781 A1   Dec. 31, 2020

Related U.S. Application Data

(63) Continuation of application No. PCT/IB2019/052016, filed on Mar. 12, 2019.
(Continued)

(51) Int. Cl.
*A61K 35/742*  (2015.01)
*A61P 31/04*  (2006.01)
(Continued)

(52) U.S. Cl.
CPC .......... *A61K 35/742* (2013.01); *A61P 31/04* (2018.01); *A61P 31/10* (2018.01); *C12N 1/205* (2021.05);
(Continued)

(58) Field of Classification Search
CPC ....... C12N 1/205; A61K 35/742; A61P 31/04; A61P 31/10; C12R 2001/125; C12R 2001/07
See application file for complete search history.

(56) References Cited

U.S. PATENT DOCUMENTS

| 2,293,722 A | 8/1942 | Erickson |
| D221,836 S | 9/1971 | Giles et al. |
| (Continued) | | |

FOREIGN PATENT DOCUMENTS

| CN | 1177636 | 4/1998 |
| CN | 1642827 | 7/2005 |
| (Continued) | | |

OTHER PUBLICATIONS

Notice of Allowance dated Mar. 4, 2022 From the US Patent and Trademark Office Re. U.S. Appl. No. 17/019,280. (7 Pages).
(Continued)

*Primary Examiner* — Jana A Hines

(57) ABSTRACT

A composition comprising at least two bacterial strains selected from the group consisting of *Bacillus subtilis* 281, *Bacillus subtilis* 3, *Bacillus amyloliquefaciens* 298 and a functional homolog of any of the preceding, wherein the composition does not comprise more than 5 different species of microbes, wherein:
  a sample of *Bacillus subtilis* 281, has been deposited as KCTC 13468BP at the Korean Collection for Type Cultures;
  a sample of *Bacillus subtilis* 3, has been deposited as KCTC 13467BP at the Korean Collection for Type Cultures; and
  a sample of *Bacillus amyloliquefaciens* 298, has been deposited as KCTC 13469BP at the Korean Collection
(Continued)

for Type Cultures. Also provided are methods that utilize the bacterial strains or functional homologs of same.

4 Claims, 12 Drawing Sheets

Specification includes a Sequence Listing.

Related U.S. Application Data

(60) Provisional application No. 62/641,443, filed on Mar. 12, 2018, provisional application No. 62/641,444, filed on Mar. 12, 2018, provisional application No. 62/641,445, filed on Mar. 12, 2018, provisional application No. 62/641,464, filed on Mar. 12, 2018.

(51) Int. Cl.
*A61P 31/10* (2006.01)
*C12N 1/20* (2006.01)
*C12R 1/07* (2006.01)
*C12R 1/125* (2006.01)

(52) U.S. Cl.
CPC .... *C12R 2001/07* (2021.05); *C12R 2001/125* (2021.05)

(56) References Cited

U.S. PATENT DOCUMENTS

| | | |
|---|---|---|
| D239,922 S | 5/1976 | Utley |
| D250,394 S | 11/1978 | Menius |
| D279,452 S | 7/1985 | Beechuk |
| D284,362 S | 6/1986 | Biesecker |
| D309,711 S | 8/1990 | Biesecker |
| D376,760 S | 12/1996 | Sykes |
| D433,336 S | 11/2000 | Weber |
| 6,405,944 B1 | 6/2002 | Benahkhoudja |
| D472,471 S | 4/2003 | McClure et al. |
| D473,143 S | 4/2003 | McClure et al. |
| D489,992 S | 5/2004 | Brauner et al. |
| D571,662 S | 6/2008 | Clark et al. |
| 7,858,336 B1 | 12/2010 | Garner et al. |
| D630,946 S | 1/2011 | Crawford |
| D656,599 S | 3/2012 | Browder |
| D663,215 S | 7/2012 | Clay et al. |
| D667,101 S | 9/2012 | Browder |
| D673,253 S | 12/2012 | Mack |
| D678,496 S | 3/2013 | Browder |
| 8,986,610 B2 | 3/2015 | Ben Haim |
| 9,486,552 B1 | 11/2016 | Ansley et al. |
| D805,909 S | 12/2017 | Matsuishi |
| D875,532 S | 2/2020 | Lehanneur |
| D879,613 S | 3/2020 | Lehanneur |
| 2003/0189066 A1 | 10/2003 | Schiller |
| 2005/0160553 A1 | 7/2005 | Gregory |
| 2005/0252930 A1 | 11/2005 | Contadini et al. |
| 2007/0217945 A1 | 9/2007 | Selander |
| 2009/0238716 A1 | 9/2009 | Weening |
| 2009/0324815 A1 | 12/2009 | Nielsen et al. |
| 2010/0021576 A1 | 1/2010 | Chang et al. |
| 2011/0214245 A1 | 9/2011 | Bassett |
| 2012/0152882 A1 | 6/2012 | Tune |
| 2012/0168971 A1 | 7/2012 | Hansen et al. |
| 2013/0015956 A1 | 1/2013 | Wegelin et al. |
| 2013/0068783 A1 | 3/2013 | Gasper et al. |
| 2014/0263426 A1 | 9/2014 | Gasper |
| 2016/0101925 A1 | 4/2016 | Franz et al. |
| 2016/0183538 A1* | 6/2016 | Taghavi. et al. ......... C05G 5/27 424/93.46 |
| 2017/0035262 A1 | 2/2017 | Li et al. |
| 2017/0035925 A1 | 2/2017 | Sevy |
| 2017/0348364 A1 | 12/2017 | Garner et al. |
| 2020/0407807 A1 | 12/2020 | Holzapfel et al. |
| 2020/0407808 A1 | 12/2020 | Holzapfel et al. |
| 2020/0407809 A1 | 12/2020 | Holzapfel et al. |
| 2021/0046256 A1 | 2/2021 | Hoffman et al. |
| 2021/0046497 A1 | 2/2021 | Hoffman et al. |
| 2021/0204774 A1 | 7/2021 | Dery et al. |

FOREIGN PATENT DOCUMENTS

| | | | |
|---|---|---|---|
| CN | 1934241 | 3/2007 | |
| CN | 103589655 | 2/2014 | |
| CN | 103703121 | 4/2014 | |
| CN | 104487566 | 4/2015 | |
| CN | 104688895 | 6/2015 | |
| CN | 104736162 | 6/2015 | |
| CN | 204501790 | 7/2015 | |
| CN | 303340433 S | 8/2015 | |
| CN | 105087423 | 11/2015 | |
| CN | 105219669 | 1/2016 | |
| CN | 205032305 | 2/2016 | |
| CN | 107567493 | * 1/2018 | .......... A61K 35/742 |
| CN | 107723267 | 2/2018 | |
| KR | 20-2009-0007893 | 8/2009 | |
| KR | 10-2014-0128870 | 11/2014 | |
| KR | 10-2017-0130341 | 11/2017 | |
| WO | WO 01/34182 | 5/2001 | |
| WO | WO 2016/060934 | 4/2016 | |
| WO | WO 2016/118864 | 7/2016 | |
| WO | WO 2019/175774 | 9/2019 | |
| WO | WO 2019/175775 | 9/2019 | |
| WO | WO 2019/175777 | 9/2019 | |
| WO | WO 2019/175777 A8 | 9/2019 | |
| WO | WO 2019/175780 | 9/2019 | |
| WO | WO 2019/175782 | 9/2019 | |
| WO | WO 2019/175782 A8 | 9/2019 | |
| WO | WO 2019/175783 | 9/2019 | |
| WO | WO 2019/224691 | 11/2019 | |
| WO | WO 2019/175783 A8 | 10/2020 | |

OTHER PUBLICATIONS

Notice of Allowance dated Mar. 9, 2022 together with Interview SUmmary Dated Feb. 16, 2022 from US Patent and Trademark Office Re. U.S. Appl. No. 16/645,509. (6 pages).
International Preliminary Report on Patentability dated Dec. 3, 2020 From the International Bureau of WIPO Re. Application No. PCT/IB2019/054141. (9 Pages).
Notice of Allowability dated Apr. 20, 2022 from US Patent and Trademark Office Re. U.S. Appl. No. 17/019,568. (4 pages).
Notice of Allowance dated Feb. 16, 2022 From the US Patent and Trademark Office Re. U.S. Appl. No. 17/019,281. (7 Pages).
Restriction Official Action dated Jul. 7, 2021 from the US Patent and Trademark Office Re. U.S. Appl. No. 17/019,280. (5 pages).
Restriction Official Action dated Jul. 7, 2021 from the US Patent and Trademark Office Re. U.S. Appl. No. 17/019,281, (5 pages).
Examination Report dated Sep. 7, 2018 From the Government of India, Patent Office, Intellectual Property Building Re.: Application No. 309690.
Examination Report dated Sep. 11, 2018 From the Government of India, Patent Office, Intellectual Property Building Re.: Application No. 309744.
International Preliminary Report on Patentability dated Sep. 24, 2020 From the International Bureau of WIPO Re. Application No. PCT/IB2019/052016. (7 Pages).
International Preliminary Report on Patentability dated Sep. 24, 2020 From the International Bureau of WIPO Re. Application No. PCT/IB2019/052008. (6 Pages).
International Preliminary Report on Patentability dated Sep. 24, 2020 From the International Bureau of WIPO Re. Application No. PCT/IB2019/052010. (7 Pages).
International Preliminary Report on Patentability dated Sep. 24, 2020 From the International Bureau of WIPO Re. Application No. PCT/IB2019/052014. (7 Pages).
International Preliminary Report on Patentability dated Sep. 24, 2020 From the International Bureau of WIPO Re. Application No. PCT/IB2019/052017. (7 Pages).

(56) References Cited

OTHER PUBLICATIONS

International Search Report and the Written Opinion dated Jul. 3, 2019 From the International Searching Authority Re. Application No. PCT/IB2019/052014. (16 Pages).
International Search Report and the Written Opinion dated Jul. 3, 2019 From the International Searching Authority Re. Application No. PCT/IB2019/052017. (14 Pages).
International Search Report and the Written Opinion dated Sep. 17, 2019 From the International Searching Authority Re. Application No. PCT/IB2019/054141. (11 Pages).
International Search Report and the Written Opinion dated Jun. 26, 2019 From the International Searching Authority Re. Application No. PCT/IB2019/052016. (15 Pages).
International Search Report and the Written Opinion dated Jun. 27, 2019 From the International Searching Authority Re. Application No. PCT/IB2019/052007. (12 Pages).
International Search Report and the Written Opinion dated Jun. 27, 2019 From the International Searching Authority Re. Application No. PCT/IB2019/052008. (10 Pages).
International Search Report and the Written Opinion dated Jun. 27, 2019 From the International Searching Authority Re. Application No. PCT/IB2019/052010. (17 Pages).
Notice of Amendment dated Dec. 11, 2018 From the State Intellectual Property Office of the People's Republic of China Re. Application No. 201830508569.8. (2 pages).
Notification of Reason for Rejection dated Jan. 30, 2019 From the Japanese Patent Office Re. Application No. 2018-019747. (2 Pages).
Official Action dated Jun. 12, 2020 from the US Patent and Trademark Office Re. U.S. Appl. No. 29/640,027. (19 pages).
Official Action dated Jun. 12, 2020 from the US Patent and Trademark Office Re. U.S. Appl. No. 29/640,032. (13 pages).
Official Action dated Jun. 25, 2020 from the US Patent and Trademark Office Re. U.S. Appl. No. 29/653,164. (9 pages).
Cho "Characterization of Potential Probiotics Bacillus Subtilis CS90 From Soybean Paste (Doenjang) and Its Antimicrobial Activity Against Food-Borne Pathogens", Journal of Applied Biological Chemistry, 51(5): 285-291, 2008.
Gu et al. "The Preventive Effect and Therapeutic Effect of Spraying Agent of Bacillus Pab02 on Respiratory Infection in Broilers", Proceedings of the 10th in the 4th National Academic Seminar and Animal Micro-Ecology Enterprise Development Forum, p. 450-458, Aug. 1, 2010.
Jeon et al. "Screening and Characterization of Potential Bacillus Starter Cultures for Fermenting Low-Salt Soybean Past (Doenjang)", Journal of Microbiology and Biotechnology, 26(4): 666-674, Apr. 2016.
Ji et al. "Probiotic Bacillus Amyloliquefaciens SC06 Prevents Bacterial Translocation in Weaned Mice", Indian Journal of Microbiology, 53(3): 323-328, Published Online Mar. 16, 2013.
Wong et al. "An Antifungal Protein From Bacillus Amyloliquefaciens", Journal of Applied Microbiology, 105(6): 1888-1898, Dec. 2008.
Xie et al. "Isolation and Characterization of A Bacteriocin Produced by an Isolated Bacillus Subtihs LFB112 That Exhibits Antimicrobial Activity Against Domestic Animal Pathogens", African Journal of Biotechnology, 8(20): 5611-5619, Oct. 19, 2009.
Restriction Official Action dated Jul. 13, 2021 from the US Patent and Trademark Office Re. U.S. Appl. No. 17/019,568. (5 pages).
Official Action dated Sep. 22, 2021 from the US Patent and Trademark Office Re. U.S. Appl. No. 17/019,280. (26 pages).
International Preliminary Report on Patentability dated Sep. 24, 2020 From the International Bureau of WIPO Re. Application No. PCT/IB2019/052007. (6 Pages).
Notice of Allowance dated Mar. 24, 2022 from US Patent and Trademark Office Re. U.S. Appl. No. 17/019,280. (4 pages).

\* cited by examiner

| | | |
|---|---|---|
|  |  |  |
| *Escherichia coli* ATCC 22922 | *Pseudomonas aeruginosa* | *Bacillus cereus* ATCC 27348 |
|  |  |  |
| *Staphylococcus aureus* ATCC 11335 | *Salmonella typhi* ATCC 14028 | *Listeria inocua* ATCC 3586 |

| | | |
|---|---|---|
|  |  |  |
| *Alternaria alternata* (Fries) Keissler ATCC® MYA-4642™ | *Cladosporium sphaerospermum* Penzig ATCC® MYA-4645™ | *Penicillium chrysogenum* Thom ATCC® MYA-4644™ |

COMPOSITIONS COMPRISING BACTERIAL STRAINS AND USE THEREOF IN CONTROLLING PATHOGENIC MICROORGANISMS

RELATED APPLICATIONS

This application is a US Continuation of PCT Patent Application No. PCT/IB2019/052016 having international filing date of Mar. 12, 2019 which claims the benefit of priority under 35 USC § 119(e) of U.S. Provisional Patent Application Nos. 62/641,443, 62/641,444, 62/641,445 and 62/641,464, all filed on Mar. 12, 2018. The contents of the above applications are all incorporated by reference as if fully set forth herein in their entirety.

PCT Patent Application No. PCT/IB2019/052016 is also related to co-filed PCT Patent Application Nos. PCT/IB2019/052008, PCT/IB2019/052007, PCT/IB2019/052010, PCT/IB2019/052017 and PCT/IB2019/052014 entitled "CARTRIDGE FOR AN AUTOMATED AEROSOL DISPENSING DEVICE", "ELECTRONIC SAFETY FEATURE FOR AN AUTOMATED AEROSOL DISPENSING DEVICE", "COMPOSITIONS COMPRISING BACTERIAL STRAINS AND USE THEREOF IN CONTROLLING PATHOGENIC MICROORGANISMS", "COMPOSITIONS COMPRISING BACTERIAL STRAINS AND USE THEREOF IN CONTROLLING PATHOGENIC MICROORGANISMS", "COMPOSITIONS COMPRISING BACTERIAL STRAINS AND USE THEREOF IN CONTROLLING PATHOGENIC MICROORGANISMS". The contents of the above applications are all incorporated by reference as if fully set forth herein in their entirety.

SEQUENCE LISTING STATEMENT

The ASCII file, entitled 84587SequenceListing.txt, created on Sep. 14, 2020, comprising 15,755,105 bytes, submitted concurrently with the filing of this application is incorporated herein by reference.

FIELD AND BACKGROUND OF THE INVENTION

The present invention, in some embodiments thereof, relates to compositions comprising bacterial strains and use thereof in controlling pathogenic microorganisms.

A respiratory tract infection (RTI) refers to any of a number of infectious diseases involving the respiratory tract. An infection of this type is normally further classified as an upper respiratory tract infection (URI or URTI) or a lower respiratory tract infection (LRI or LRTI). Lower respiratory infections, such as pneumonia, tend to be far more serious conditions than upper respiratory infections, such as the common cold.

Identifying probiotic microbial strains which can be used in the effective and safe treatment and prophylaxis of respiratory tract infections is therefore highly desired.

Additional background art includes:

Jeon, Jung et al. 2016 *J. Microbiol. Biotechnol* 26(4): 666-674;

Cho 2008 Journal of Applied Biological Chemistry 51(6): 285-291;

U.S. Publication No. 20170348364;

U.S. Pat. No. 8,986,610.

SUMMARY OF THE INVENTION

According to an aspect of some embodiments of the present invention there is provided a composition comprising at least two bacterial strains selected from the group consisting of *Bacillus subtilis* 281, *Bacillus subtilis* 3, *Bacillus amyloliquefaciens* 298 and a functional homolog of any of the preceding, wherein the composition does not comprise more than 5 different species of microbes, wherein:

a sample of *Bacillus subtilis* 281, has been deposited as KCTC 13468BP at the Korean Collection for Type Cultures;

a sample of *Bacillus subtilis* 3, has been deposited as KCTC 13467BP at the Korean Collection for Type Cultures; and a sample of *Bacillus amyloliquefaciens* 298, has been deposited as KCTC 13469BP at the Korean Collection for Type Cultures.

According to an aspect of some embodiments of the present invention there is provided an article of manufacture comprising at least two bacterial strains selected from the group consisting of *Bacillus subtilis* 281, *Bacillus subtilis* 3, *Bacillus amyloliquefaciens* 298 and a functional homolog of any of the preceding, wherein the composition does not comprise more than 5 different species of microbes, wherein:

a sample of *Bacillus subtilis* 281, has been deposited as KCTC 13468BP at the Korean Collection for Type Cultures;

a sample of *Bacillus subtilis* 3, has been deposited as KCTC 13467BP at the Korean Collection for Type Cultures; and a sample of *Bacillus amyloliquefaciens* 298, has been deposited as KCTC 13469BP at the Korean Collection for Type Cultures.

According to some embodiments of the invention, said bacterial strain or functional homolog of same is attached to a solid support.

According to some embodiments of the invention, said bacterial strain or functional homolog of same is soluble.

According to some embodiments of the invention, the article of manufacture comprises a commodity selected from the group consisting of a food, a feed, a beverage, a pharmaceutical, a nutraceutical, a cosmetic, a filter, a matrix and an aerosol system.

According to an aspect of some embodiments of the present invention there is provided an aerosol dispensing device comprising an effective amount of at least two bacterial strains selected from the group consisting of *Bacillus subtilis* 281, *Bacillus subtilis* 3, *Bacillus amyloliquefaciens* 298 and a functional homolog of any of the preceding, wherein the composition does not comprise more than 5 different species of microbes, wherein:

a sample of *Bacillus subtilis* 281, has been deposited as KCTC 13468BP at the Korean Collection for Type Cultures;

a sample of *Bacillus subtilis* 3, has been deposited as KCTC 13467BP at the Korean Collection for Type Cultures; and a sample of *Bacillus amyloliquefaciens* 298, has been deposited as KCTC 13469BP at the Korean Collection for Type Cultures.

According to some embodiments of the invention, the aerosol dispensing device is automated.

According to some embodiments of the invention, said bacterial strain or said functional homolog comprises a genomic nucleic acid sequence at least 97% identical to the nucleic acid sequence set forth in SEQ ID NO: 4, 6 or 8.

According to some embodiments of the invention, said bacterial strain or said functional homolog exhibits:

(i) growth inhibitory effects against bacteria and fungi, as shown in Tables 3, 4, 8, 9, 13, 14, 18 and 19.

(ii) no lecithinase activity as determined by the absence of a white precipitate when the isolated bacterial strain or functional homolog of same is streaked out onto egg yolk agar and incubated for 24 h at 37° C.; and (iii) gamma hemolytic activity when streaked onto 5% sheep blood agar and incubated for 24 h at 37° C.

According to some embodiments of the invention, the bacterial strain or functional homolog of same is sensitive to an antibiotic selected from the group consisting of erythromycin, gentamicin, tetracycline, streptomycin, vancomycin, chloramphenicol, kanamycin and clindamycin according to the European Food Safety Authority MIC breakpoints for *Bacillus* species.

According to some embodiments of the invention, the bacterial strain or functional homolog of same is incapable of colonizing a mammalian lung.

According to some embodiments of the invention, the bacterial strain or functional homolog of same exhibits growth inhibitory effects against bacteria and fungi, as shown in Tables 3, 4, 8, 9, 13, 14, 18 and 19.

According to some embodiments of the invention, said functional homolog is characterized by at least one of:

at least 70% DNA-DNA relatedness to the deposited strain with 5 uC or less DTm;

at least 97% genomic DNA sequence identity to the genomic DNA sequence of the deposited strain;

having an average nucleotide identity (ANI) of at least about 97% with the deposited strain;

having a tetranucleotide signature frequency correlation coefficient of at least about 0.99 with the deposited strain;

having a Dice similarity coefficient;

being of the same ribotype as that of the deposited strain;

having a Pearson correlation coefficient of at least about 0.99 with the deposited strain;

having a multilocus sequence typing (MLST) of at least about 0.99 with the deposited strain;

having a functionality conserved gene that is at least about 97% identical to that of the deposited strain as determined at a level of a single gene or multilocus sequence analysis (MLSA);

having a 16S nucleic acid sequence that is at least about 97% identical to that of the deposited strain;

having substantially the same biochemical profiling as determined by the GEN III redox chemistry;

maintaining the coding and/or non-coding sequence order as that of the deposited strain;

having the same codon usage as that of the deposited strain.

According to some embodiments of the invention, the composition, article of manufacture or device comprises *Bacillus subtilis* 281, *Bacillus subtilis* 3 and *Bacillus amyloliquefaciens* 298 or a functional homolog of same.

According to some embodiments of the invention, said *Bacillus subtilis* 281, *Bacillus subtilis* 3 and *Bacillus amyloliquefaciens* 298 or a functional homolog of same are present in a ration of about 1:1:1.

According to an aspect of some embodiments of the present invention there is provided a method of controlling a population of pathogenic bacteria and/or fungi, the method comprising providing an effective amount of the composition, thereby controlling the population of pathogenic bacteria and/or fungi.

According to some embodiments of the invention, said controlling is prophylactic.

According to some embodiments of the invention, said controlling is therapeutic.

According to some embodiments of the invention, said contacting comprises in vivo contacting.

According to some embodiments of the invention, said contacting is by inhalation.

According to some embodiments of the invention, said contacting is by oral administration.

According to some embodiments of the invention, said contacting is by enteral administration.

According to some embodiments of the invention, said contacting is by paraenteral administration.

According to some embodiments of the invention, said contacting comprises in vitro contacting.

According to some embodiments of the invention, said contacting is by using the aerosol dispensing device.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

DESCRIPTION OF SPECIFIC EMBODIMENTS OF THE INVENTION

Figure 1:
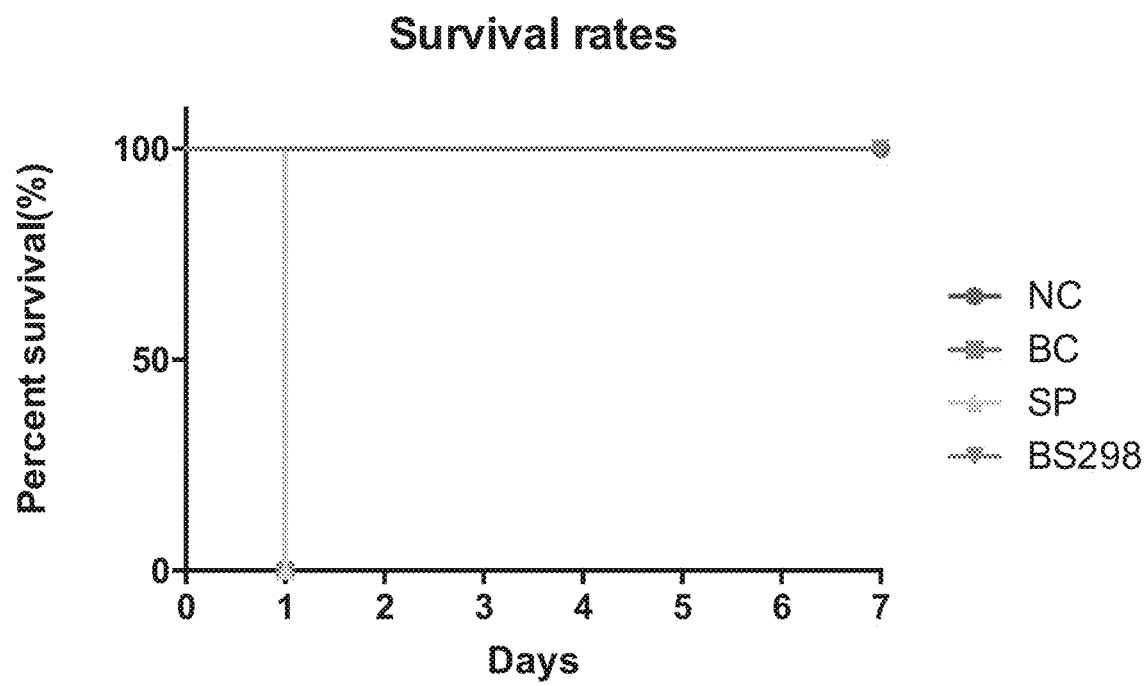
FIG. 1 is a graph showing the survival rates of mice after respiratory tract infection (NC: negative control, BC: *B. cereus*, SP: *S. pneumoniae*, BS298: *B. amyloliquefaciens* 298).

The present invention, in some embodiments thereof, relates to compositions comprising bacterial strains and use thereof in controlling pathogenic microorganisms. Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

In a search for probiotic bacterial strains that can be effectively and safely used in controlling pathogenic microorganisms, the present inventors have identified a novel strains of *Bacillus* strains. The pathogenicity of the strains was assessed using in-vitro methods such as lecithinase activity, hemolysis tests and resistance to therapeutic antibiotics. Safety was also evaluated in-vivo through a lung infection model in mice. Lastly, the efficacy of the strains in inhibiting the growth of pathogenic microorganisms was affirmed in-vitro.

Collectively these assays place the compositions described according to some embodiments as both safe for respiratory tract infection and functional with high potential to be used in various domestic, clinical and industrial applications.

According to an aspect of some embodiments of the present invention there is provided a composition comprising at least two bacterial strains selected from the group consisting of *Bacillus subtilis* 281, *Bacillus subtilis* 3, *Bacillus amyloliquefaciens* 298 and a functional homolog of any of the preceding, wherein the composition does not comprise more than 5 different species of microbes, wherein:

a sample of *Bacillus subtilis* 281, has been deposited as KCTC 13468BP at the Korean Collection for Type Cultures;

a sample of *Bacillus subtilis* 3, has been deposited as KCTC 13467BP at the Korean Collection for Type Cultures; and a sample of *Bacillus amyloliquefaciens* 298, has been deposited as KCTC 13469BP at the Korean Collection for Type Cultures.

According to an aspect of some embodiments of the present invention there is provided an article of manufacture comprising at least two bacterial strains selected from the group consisting of *Bacillus subtilis* 281, *Bacillus subtilis* 3, *Bacillus amyloliquefaciens* 298 and a functional homolog of any of the preceding, wherein the composition does not comprise more than 5 different species of microbes, wherein:

a sample of *Bacillus subtilis* 281, has been deposited as KCTC 13468BP at the Korean Collection for Type Cultures;

a sample of *Bacillus subtilis* 3, has been deposited as KCTC 13467BP at the Korean Collection for Type Cultures; and a sample of *Bacillus amyloliquefaciens* 298, has been deposited as KCTC 13469BP at the Korean Collection for Type Cultures.

According to some embodiments of the invention, said bacterial strain or functional homolog of same is attached to a solid support.

According to some embodiments of the invention, said bacterial strain or functional homolog of same is soluble.

According to some embodiments of the invention, the article of manufacture comprises a commodity selected from the group consisting of a food, a feed, a beverage, a pharmaceutical, a nutraceutical, a cosmetic, a filter, a matrix and an aerosol system.

According to an aspect of some embodiments of the present invention there is provided an aerosol dispensing device comprising an effective amount of at least two bacterial strains selected from the group consisting of *Bacillus subtilis* 281, *Bacillus subtilis* 3, *Bacillus amyloliquefaciens* 298 and a functional homolog of any of the preceding, wherein the composition does not comprise more than 5 different species of microbes, wherein:

a sample of *Bacillus subtilis* 281, has been deposited as KCTC 13468BP at the Korean Collection for Type Cultures;

a sample of *Bacillus subtilis* 3, has been deposited as KCTC 13467BP at the Korean Collection for Type Cultures; and a sample of *Bacillus amyloliquefaciens* 298, has been deposited as KCTC 13469BP at the Korean Collection for Type Cultures.

According to some embodiments of the invention, the aerosol dispensing device is automated.

According to some embodiments of the invention, said bacterial strain or said functional homolog comprises a genomic nucleic acid sequence at least 97% identical to the nucleic acid sequence set forth in SEQ ID NO: 4, 6 or 8.

According to some embodiments of the invention, said bacterial strain or said functional homolog exhibits:

(i) growth inhibitory effects against bacteria and fungi, as shown in Tables 3, 4, 8, 9, 13, 14, 18 and 19.

(ii) no lecithinase activity as determined by the absence of a white precipitate when the isolated bacterial strain or functional homolog of same is streaked out onto egg yolk agar and incubated for 24 h at 37° C.; and (iii) gamma hemolytic activity when streaked onto 5% sheep blood agar and incubated for 24 h at 37° C.

According to some embodiments of the invention, the bacterial strain or functional homolog of same is sensitive to an antibiotic selected from the group consisting of erythromycin, gentamicin, tetracycline, streptomycin, vancomycin, chloramphenicol, kanamycin and clindamycin according to the European Food Safety Authority MIC breakpoints for *Bacillus* species.

According to some embodiments of the invention, the bacterial strain or functional homolog of same is incapable of colonizing a mammalian lung.

According to some embodiments of the invention, the bacterial strain or functional homolog of same exhibits growth inhibitory effects against bacteria and fungi, as shown in Tables 3, 4, 8, 9, 13, 14, 18 and 19.

According to some embodiments of the invention, said functional homolog is characterized by at least one of:

at least 70% DNA-DNA relatedness to the deposited strain with 5 uC or less DTm;

at least 97% genomic DNA sequence identity to the genomic DNA sequence of the deposited strain;

having an average nucleotide identity (ANI) of at least about 97% with the deposited strain;

having a tetranucleotide signature frequency correlation coefficient of at least about 0.99 with the deposited strain;

having a Dice similarity coefficient;

being of the same ribotype as that of the deposited strain;

having a Pearson correlation coefficient of at least about 0.99 with the deposited strain;

having a multilocus sequence typing (MLST) of at least about 0.99 with the deposited strain;

having a functionality conserved gene that is at least about 97% identical to that of the deposited strain as determined at a level of a single gene or multilocus sequence analysis (MLSA);

having a 16S nucleic acid sequence that is at least about 97% identical to that of the deposited strain;

having substantially the same biochemical profiling as determined by the GEN III redox chemistry;

maintaining the coding and/or non-coding sequence order as that of the deposited strain;

having the same codon usage as that of the deposited strain.

According to some embodiments of the invention, the composition, article of manufacture or device comprises *Bacillus subtilis* 281, *Bacillus subtilis* 3 and *Bacillus amyloliquefaciens* 298 or a functional homolog of same.

According to some embodiments of the invention, said *Bacillus subtilis* 281, *Bacillus subtilis* 3 and *Bacillus amyloliquefaciens* 298 or a functional homolog of same are present in a ration of about 1:1:1.

According to an aspect of some embodiments of the present invention there is provided a method of controlling a population of pathogenic bacteria and/or fungi, the method comprising providing an effective amount of the composition, thereby controlling the population of pathogenic bacteria and/or fungi.

According to some embodiments of the invention, said controlling is prophylactic.

According to some embodiments of the invention, said controlling is therapeutic.

According to some embodiments of the invention, said contacting comprises in vivo contacting.

According to some embodiments of the invention, said contacting is by inhalation.

According to some embodiments of the invention, said contacting is by oral administration.

According to some embodiments of the invention, said contacting is by enteral administration.

According to some embodiments of the invention, said contacting is by paraenteral administration.

According to some embodiments of the invention, said contacting comprises in vitro contacting.

According to some embodiments of the invention, said contacting is by using the aerosol dispensing device.

KCTC 13469BP has been deposited in the Korean Collection for Type Cultures, Korea Research Institute of Bioscience and Biotechnology (KRIBB) 181, Ipsin-gil, Jeongeup-si, Jeolllabuk-do 56212, Republic of Korea on Jan. 25, 2018.

The bacterial strain can be as deposited or a variant thereof, also referred to herein as a "functional homolog".

KCTC 13467BP has been deposited in the Korean Collection for Type Cultures, Korea Research Institute of Bioscience and Biotechnology (KRIBB) 181, Ipsin-gil, Jeongeup-si, Jeolllabuk-do 56212, Republic of Korea on Jan. 25, 2018.

The bacterial strain can be as deposited or a variant thereof, also referred to herein as a "functional homolog".

KCTC 13468BP has been deposited in the Korean Collection for Type Cultures, Korea Research Institute of Bioscience and Biotechnology (KRIBB) 181, Ipsin-gil, Jeongeup-si, Jeolllabuk-do 56212, Republic of Korea on Jan. 25, 2018.

The bacterial strain can be as deposited or a variant thereof, also referred to herein as a "functional homolog".

The term "the microbial strain" or "the bacterial strain" can refer to the deposited strain and/or the functional homolog.

As used herein "functional homolog" or "functionally homologous" or "variant" or a grammatical equivalent as used herein, refers to a modification (i.e., at least one mutation) of the deposited microbial strain resulting in a microbial strain that is endowed with substantially the same ensemble of biological activities (+/−10%, 20%, 40%, 50%, 60% when tested under the same conditions) as that of the deposited strain (see hereinbelow and in the Examples section which follows) and can be classified to the same species or strain based on known methods of species/strain classifications.

Following are non-limiting criteria for identifying a functional homolog. These criteria, which are mostly genetic, combined with the functional characteristic as defined hereinbelow and in the Examples section, which follows, will be facilitate the skilled artisan in defining the scope of the functional homolog.

Thus, according to a specific embodiment, the deposited strain and the functional homolog belong to the same operational taxonomic units (OTU).

An "OTU" (or plural, "OTUs") refers to a terminal leaf in a phylogenetic tree and is defined by a nucleic acid sequence, e.g., the entire genome, or a specific genetic sequence, and all sequences that share sequence identity to this nucleic acid sequence at the level of species. In some embodiments the specific genetic sequence may be the 16S-rRNA sequence or a portion of the 16S-rRNA (also referred to herein as "16S") sequence or other functionally conserved genes as listed below. In other embodiments, the entire genomes of two entities are sequenced and compared. In another embodiment, selected regions such as multilocus sequence tags (MLST, MLSA), specific genes, or sets of genes may be genetically compared. In 16S-rRNA embodiments, OTUs that share at least 97% average nucleotide identity across the entire 16S or some variable region of the 16S are considered the same OTU (see e.g. Claesson M J, Wang Q, O'Sullivan O, Greene-Diniz R, Cole J R, Ros R P, and O'Toole P W. 2010. Comparison of two next-generation sequencing technologies for resolving highly complex microbiota composition using tandem variable 16S rRNA gene regions. Nucleic Acids Res 38: e200. Konstantinidis K T, Ramette A, and Tiedje J M. 2006. The bacterial species definition in the genomic era. Philos Trans R Soc Lond B Biol Sci 361: 1929-1940). In embodiments involving the complete genome, MLSTs, specific genes, or sets of genes OTUs that share at least 95% average nucleotide identity are considered the same OTU (see e.g. Achtman M, and Wagner M. 2008. Microbial diversity and the genetic nature of microbial species. Nat. Rev. Microbiol. 6: 431-440. Konstantinidis K T, Ramette A, and Tiedje J M. 2006. The bacterial species definition in the genomic era. Philos Trans R Soc Lond B Biol Sci 361: 1929-1940). OTUs are frequently defined by comparing sequences between organisms. Such characterization employs, e.g., WGS data or a whole genome sequence.

According to a specific embodiment, the classification is based on DNA-DNA pairing data and/or sequence identity to functionally conserved genes or fragments thereof.

According to a specific embodiment a species/strain can be defined by DNA-DNA hybridization involving a pairwise comparison of two entire genomes and reflects the overall sequence similarity between them. According to a specific embodiment, a species is defined as a set of strains with at least about 70%, e.g., at least about 75%, at least about 80%, at least about 85%, at least about 90%, at least about 91%, at least about 92%, at least about 93%, at least about 94%, at least about 95% or more DNA-DNA relatedness and with 5 uC or less DTm and having the activities as defined hereinbelow and in the Examples section which follows.

According to a specific embodiment, the genomic nucleic acid sequence is at least about 97%, at least about 97.1%, at least about 97.2%, at least about 97.3%, at least about 97.4%, at least about 97.5%, at least about 97.6%, at least about 97.7%, at least about 97.8%, at least about 97.9%, at least about 98%, at least about 98.1%, at least about 98.2%, at least about 98.3%, at least about 98.4%, at least about 98.5%, at least about 98.6%, at least about 98.7%, at least about 98.8%, at least about 98.9%, at least about 99%, at least about 99.1%, at least about 99.2%, at least about 99.3%, at least about 99.4%, at least about 99.5%, at least about 99.6%, at least about 99.7%, at least about 99.8%, at least about 99.8%, at least about 99.9%, at least about 99.95% 99.95%, at least about 99.99%, at least about 99.999%, at least about 99.9999%, at least about 99.99999%, at least about 99.999999% or more DNA-DNA relatedness and with 5 uC or less DTm and having the activities hereinbelow and in the Examples section which follows.

Thus, for example, if there is DNA-DNA hybridization on the basis of the article of Goris et al. [Goris, J., Konstantinidis, K. T., Klappenbach, J. A., Coenye, T., Vandamme, P., and Tiedje, J M. (2007). DNA-DNA hybridization values and their relationship to whole-genome sequence similarities. Int J Syst Evol Microbiol 57:81-91], some microorganisms expressing a DNA-DNA relatedness value of 70% or more (as described above) can be regarded as functional homologs according to some embodiments of the invention.

According to a specific embodiment, the reference genomic sequence is as set forth in SEQ ID NO: 4, 6 or 8.

As used herein, "sequence identity" or "identity" or grammatical equivalents as used herein in the context of two nucleic acid or polypeptide sequences includes reference to the residues in the two sequences which are the same when aligned. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are considered to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Henikoff S and Henikoff J G. [Amino acid substitution matrices from protein blocks. Proc. Natl. Acad. Sci. U.S.A. 1992, 89(22): 10915-9].

Identity can be determined using any homology comparison software, including for example, the BlastN software of the National Center of Biotechnology Information (NCBI) such as by using default parameters.

According to some embodiments of the invention, the identity is a global identity, i.e., an identity over the entire nucleic acid sequences of the invention and not over portions thereof.

According to a specific embodiment, the genomic nucleic acid sequence is at least about 70%, e.g., at least 75%, at least about 80%, at least about 85%, at least about 90%, at least about 91%, at least about 92%, at least about 93%, at least about 94%, at least about 95%, at least about 96% least about 97%, at least about 97.1%, at least about 97.2%, at least about 97.3%, at least about 97.4%, at least about 97.5%, at least about 97.6%, at least about 97.7%, at least about 97.8%, at least about 97.9%, at least about 98%, at least about 98.1%, at least about 98.2%, at least about 98.3%, at least about 98.4%, at least about 98.5%, at least about 98.6%, at least about 98.7%, at least about 98.8%, at least about 98.9%, at least about 99%, at least about 99.1%, at least about 99.2%, at least about 99.3%, at least about 99.4%, at least about 99.5%, at least about 99.6%, at least about 99.7%, at least about 99.8%, at least about 99.8%, at least about 99.9%, at least about 99.95% 99.95%, at least about 99.99%, at least about 99.999%, at least about 99.9999%, at least about 99.99999%, at least about 99.999999% or more to the genomic sequence of the deposited strain (SEQ ID NO: 4, 6 or 8).

According to a specific embodiment, the genomic nucleic acid sequence is at least about 97%, at least about 97.1%, at least about 97.2%, at least about 97.3%, at least about 97.4%, at least about 97.5%, at least about 97.6%, at least about 97.7%, at least about 97.8%, at least about 97.9%, at least about 98%, at least about 98.1%, at least about 98.2%, at least about 98.3%, at least about 98.4%, at least about 98.5%, at least about 98.6%, at least about 98.7%, at least about 98.8%, at least about 98.9%, at least about 99%, at least about 99.1%, at least about 99.2%, at least about 99.3%, at least about 99.4%, at least about 99.5%, at least about 99.6%, at least about 99.7%, at least about 99.8%, at least about 99.8%, at least about 99.9%, 99.95%, at least about 99.99%, at least about 99.999%, at least about 99.9999%, at least about 99.99999%, at least about 99.999999% or more identical to that of the deposited strain (SEQ ID NO: 4, 6 or 8).

According to an additional or alternative embodiment, a functional homolog is determined as the average nucleotide identity (ANI), which detects the DNA conservation of the core genome (Konstantinidis K and Tiedje J M, 2005, Proc. Natl. Acad. Sci. USA 102: 2567-2592). In some embodiments, the ANI between the functional homolog and the deposited strain is of at least about 95%, at least about, 96%, at least about 97%, at least about 98%, at least about 99%, at least about 99.1%, at least about 99.5%, at least about 99.6%, at least about 99.7%, at least about 99.8%, at least about 99.9%, at least about 99.99%, at least about 99.999%, at least about 99.9999%, at least about 99.99999%, at least about 99.999999% or more.

According to an additional or alternative embodiment, a functional homolog is determined by the degree of relatedness between the functional homolog and deposited strain determined as the Tetranucleotide Signature Frequency Correlation Coefficient, which is based on oligonucleotide frequencies (Bohlin J. et al. 2008, BMC Genomics, 9:104). In some embodiments, the Tetranucleotide Signature Frequency Correlation coefficient between the variant and the deposited strain is of about 0.99, 0.999, 0.9999, 0.99999, 0.999999, 0.999999 or more.

According to an additional or alternative embodiment, the degree of relatedness between the functional homolog and the deposited strain is determined as the degree of similarity obtained when analyzing the genomes of the parent and of the variant strain by Pulsed-field gel electrophoresis (PFGE) using one or more restriction endonucleases. The degree of similarity obtained by PFGE can be measured by the Dice similarity coefficient. In some embodiments, the Dice similarity coefficient between the variant and the deposited strain is of at least about 96%, at least about 97%, at least about 98%, at least about 99%, at least about 99.1%, at least about 99.5%, at least about 99.6%, at least about 99.7%, at least about 99.8%, at least about 99.9%, at least about 99.99%, at least about 99.999%, at least about 99.9999%, at least about 99.99999%, at least about 99.999999% or more.

According to an additional or alternative embodiment, the functional homolog is defined as having the same ribotype, as obtained using any of the methods known in the art and described, for instance, by Bouchet et al. (Clin. Microbiol. Rev., 2008, 21:262-273).

According to an additional or alternative embodiment, the degree of relatedness between the functional homolog and the deposited strain is determined by the Pearson correlation coefficient obtained by comparing the genetic profiles of both strains obtained by repetitive extragenic palindromic element-based PCR (REP-PCR) (see e.g. Chou and Wang, Int J Food Microbiol. 2006, 110:135-48). In some embodiments, the Pearson correlation coefficient obtained by comparing the REP-PCR profiles of the variant and the deposited strain is of at least about 0.99, at least about 0.999, at least about 0.9999, at least about 0.99999, at least about 0.999999, at least about 0.999999 or more.

According to an additional or alternative embodiment, the degree of relatedness between the functional homolog and the deposited strains is defined by the linkage distance obtained by comparing the genetic profiles of both strains obtained by Multilocus sequence typing (MLST) (see e.g. Maiden, M. C., 1998, Proc. Natl. Acad. Sci. USA 95:3140-3145). In some embodiments, the linkage distance obtained by MLST of the functional homolog and the deposited strain is of at least about 0.99, at least about 0.999, at least about 0.9999, at least about 0.99999, at least about 0.999999, at least about 0.999999 or more.

According to an additional or alternative embodiment, the functional homolog comprises a functionally conserved gene or a fragment thereof e.g., a house-keeping gene e.g., 16S-rRNA or Internal Transcribed Spacer" (ITS), recA, glnII, atpD, gap, glnA, gltA, gyrB, pnp, rpoB, thrC or dnaK that is at least about 97%, at least about 98%, at least about 99%, at least about 99.1%, at least about 99.5%, at least about 99.6%, at least about 99.7%, at least about 99.8%, at least about 99.9%, at least about 99.99%, at least about 99.999%, at least about 99.9999%, at least about 99.99999%, at least about 99.999999% or more identical to that of the deposited strain.

As mentioned, and according to a specific additional or an alternative embodiment, a functional homolog can also be determined on the basis of a multilocus sequence analysis (MLSA) determination of various functionally conserved genes or fragments thereof e.g., at least one, 2, 3, 4, 5, 6, 7, 8, 9, 10, 11, 12, 13, 14, 15 or more functionally conserved genes or fragments thereof, such as of e.g., 16S, ITS, recA, glnII, atpD, gap, glnA, gltA, gyrB, pnp, rpoB, thrC and dnaK.

According to a specific embodiment, the 16S ribosomal RNA (16S-rRNA) nucleic acid sequence is at least about 97%, e.g., at least about 97.1%, at least about 97.2%, at least about 97.3%, at least about 97.4%, at least about 97.5%, at least about 97.6%, at least about 97.7%, at least about 97.8%, at least about 97.9%, at least about 98%, at least about 98.1%, at least about 98.2%, at least about 98.3%, at least about 98.4%, at least about 98.5%, at least about 98.6%, at least about 98.7%, at least about 98.8%, at least about 98.9%, at least about 99%, at least about 99.1%, at least about 99.2%, at least about 99.3%, at least about 99.4%, at least about 99.5%, at least about 99.6%, at least about 99.7%, at least about 99.8%, at least about 99.8%, at least about 99.9%, at least about 99.95%, at least about 99.999%, at least about 99.9999%, at least about 99.99999%, at least about 99.999999% or more identical to that of the deposited strain (SEQ ID NO: 3, 5 or 7).

According to a specific embodiment, the ITS nucleic acid sequence is at least about 97%, e.g. at least about 97.1%, at least about 97.2%, at least about 97.3%, at least about 97.4%, at least about 97.5%, at least about 97.6%, at least about 97.7%, at least about 97.8%, at least about 97.9%, at least about 98%, at least about 98.1%, at least about 98.2%, at least about 98.3%, at least about 98.4%, at least about 98.5%, at least about 98.6%, at least about 98.7%, at least about 98.8%, at least about 98.9%, at least about 99%, at least about 99.1%, at least about 99.2%, at least about 99.3%, at least about 99.4%, at least about 99.5%, at least about 99.6%, at least about 99.7%, at least about 99.8%, at least about 99.8%, at least about 99.9%, at least about 99.95%, at least about 99.999%, at least about 99.9999%, at least about 99.99999%, at least about 99.999999% or more identical to that of the deposited strain.

According to a specific embodiment, the recA nucleic acid sequence is at least about 97%, e.g., at least about 97.1%, at least about 97.2%, at least about 97.3%, at least about 97.4%, at least about 97.5%, at least about 97.6%, at least about 97.7%, at least about 97.8%, at least about 97.9%, at least about 98%, at least about 98.1%, at least about 98.2%, at least about 98.3%, at least about 98.4%, at least about 98.5%, at least about 98.6%, at least about 98.7%, at least about 98.8%, at least about 98.9%, at least about 99%, at least about 99.1%, at least about 99.2%, at least about 99.3%, at least about 99.4%, at least about 99.5%, at least about 99.6%, at least about 99.7%, at least about 99.8%, at least about 99.8%, at least about 99.9%, at least about 99.95%, at least about 99.999%, at least about 99.9999%, at least about 99.99999%, at least about 99.999999% or more identical to that of the deposited strain.

According to a specific embodiment, the atpD nucleic acid sequence is at least about 97%, e.g., at least about 97.1%, at least about 97.2%, at least about 97.3%, at least about 97.4%, at least about 97.5%, at least about 97.6%, at least about 97.7%, at least about 97.8%, at least about 97.9%, at least about 98%, at least about 98.1%, at least about 98.2%, at least about 98.3%, at least about 98.4%, at least about 98.5%, at least about 98.6%, at least about 98.7%, at least about 98.8%, at least about 98.9%, at least about 99%, at least about 99.1%, at least about 99.2%, at least about 99.3%, at least about 99.4%, at least about 99.5%, at least about 99.6%, at least about 99.7%, at least about 99.8%, at least about 99.8%, at least about 99.9%, at least about 99.95%, at least about 99.999%, at least about 99.9999%, at least about 99.99999%, at least about 99.999999% or more identical to that of the deposited strain.

According to a specific embodiment, the dnaK nucleic acid sequence is at least about 97%, e.g., at least about 97.1%, at least about 97.2%, at least about 97.3%, at least about 97.4%, at least about 97.5%, at least about 97.6%, at least about 97.7%, at least about 97.8%, at least about 97.9%, at least about 98%, at least about 98.1%, at least about 98.2%, at least about 98.3%, at least about 98.4%, at least about 98.5%, at least about 98.6%, at least about 98.7%, at least about 98.8%, at least about 98.9%, at least about 99%, at least about 99.1%, at least about 99.2%, at least about 99.3%, at least about 99.4%, at least about 99.5%, at least about 99.6%, at least about 99.7%, at least about 99.8%, at least about 99.8%, at least about 99.9%, at least about 99.95%, at least about 99.999%, at least about 99.9999%, at least about 99.99999%, at least about 99.999999% or more identical to that of the deposited strain.

According to a specific embodiment, the glnII nucleic acid sequence is at least about 97%, e.g., at least about 97.1%, at least about 97.2%, at least about 97.3%, at least about 97.4%, at least about 97.5%, at least about 97.6%, at least about 97.7%, at least about 97.8%, at least about 97.9%, at least about 98%, at least about 98.1%, at least about 98.2%, at least about 98.3%, at least about 98.4%, at least about 98.5%, at least about 98.6%, at least about 98.7%, at least about 98.8%, at least about 98.9%, at least about 99%, at least about 99.1%, at least about 99.2%, at least about 99.3%, at least about 99.4%, at least about 99.5%, at least about 99.6%, at least about 99.7%, at least about 99.8%, at least about 99.8%, at least about 99.9%, at least about 99.95%, at least about 99.999%, at least about 99.9999%, at least about 99.99999%, at least about 99.999999% or more identical to that of the deposited strain.

According to a specific embodiment, the gap nucleic acid sequence is at least about 97%, e.g., at least about 97.1%, at least about 97.2%, at least about 97.3%, at least about 97.4%, at least about 97.5%, at least about 97.6%, at least about 97.7%, at least about 97.8%, at least about 97.9%, at least about 98%, at least about 98.1%, at least about 98.2%, at least about 98.3%, at least about 98.4%, at least about 98.5%, at least about 98.6%, at least about 98.7%, at least about 98.8%, at least about 98.9%, at least about 99%, at least about 99.1%, at least about 99.2%, at least about 99.3%, at least about 99.4%, at least about 99.5%, at least about 99.6%, at least about 99.7%, at least about 99.8%, at least about 99.8%, at least about 99.9%, at least about 99.95%, at least about 99.999%, at least about 99.9999%, at least about 99.99999%, at least about 99.999999% or more identical to that of the deposited strain.

According to a specific embodiment, the glnA nucleic acid sequence is at least about 97%, e.g., at least about 97.1%, at least about 97.2%, at least about 97.3%, at least about 97.4%, at least about 97.5%, at least about 97.6%, at least about 97.7%, at least about 97.8%, at least about 97.9%, at least about 98%, at least about 98.1%, at least about 98.2%, at least about 98.3%, at least about 98.4%, at least about 98.5%, at least about 98.6%, at least about 98.7%, at least about 98.8%, at least about 98.9%, at least about 99%, at least about 99.1%, at least about 99.2%, at least about 99.3%, at least about 99.4%, at least about 99.5%, at least about 99.6%, at least about 99.7%, at least about 99.8%, at least about 99.8%, at least about 99.9%, at least about 99.95%, at least about 99.999%, at least about 99.9999%, at least about 99.99999%, at least about 99.999999% or more identical to that of the deposited strain.

According to a specific embodiment, the gltA nucleic acid sequence is at least about 97%, e.g., at least about 97.1%, at least about 97.2%, at least about 97.3%, at least about 97.4%, at least about 97.5%, at least about 97.6%, at least about 97.7%, at least about 97.8%, at least about 97.9%, at least about 98%, at least about 98.1%, at least about 98.2%, at least about 98.3%, at least about 98.4%, at least about 98.5%, at least about 98.6%, at least about 98.7%, at least about 98.8%, at least about 98.9%, at least about 99%, at least about 99.1%, at least about 99.2%, at least about 99.3%, at least about 99.4%, at least about 99.5%, at least about 99.6%, at least about 99.7%, at least about 99.8%, at least about 99.8%, at least about 99.9%, at least about 99.95%, at least about 99.999%, at least about 99.9999%, at least about 99.99999%, at least about 99.999999% or more identical to that of the deposited strain.

According to a specific embodiment, the gyrB nucleic acid sequence is at least about 97%, e.g., at least about 97.1%, at least about 97.2%, at least about 97.3%, at least about 97.4%, at least about 97.5%, at least about 97.6%, at least about 97.7%, at least about 97.8%, at least about 97.9%, at least about 98%, at least about 98.1%, at least about 98.2%, at least about 98.3%, at least about 98.4%, at least about 98.5%, at least about 98.6%, at least about 98.7%, at least about 98.8%, at least about 98.9%, at least about 99%, at least about 99.1%, at least about 99.2%, at least about 99.3%, at least about 99.4%, at least about 99.5%, at least about 99.6%, at least about 99.7%, at least about 99.8%, at least about 99.8%, at least about 99.9%, at least about 99.95%, at least about 99.999%, at least about 99.9999%, at least about 99.99999%, at least about 99.999999% or more identical to that of the deposited strain.

According to a specific embodiment, the pnp nucleic acid sequence is at least about 97%, e.g., at least about 97.1%, at least about 97.2%, at least about 97.3%, at least about 97.4%, at least about 97.5%, at least about 97.6%, at least about 97.7%, at least about 97.8%, at least about 97.9%, at least about 98%, at least about 98.1%, at least about 98.2%, at least about 98.3%, at least about 98.4%, at least about 98.5%, at least about 98.6%, at least about 98.7%, at least about 98.8%, at least about 98.9%, at least about 99%, at least about 99.1%, at least about 99.2%, at least about 99.3%, at least about 99.4%, at least about 99.5%, at least about 99.6%, at least about 99.7%, at least about 99.8%, at least about 99.8%, at least about 99.9%, at least about 99.95%, at least about 99.999%, at least about 99.9999%, at least about 99.99999%, at least about 99.999999% or more identical to that of the deposited strain.

According to a specific embodiment, the rpoB nucleic acid sequence is at least about 97%, e.g., at least about 97.1%, at least about 97.2%, at least about 97.3%, at least about 97.4%, at least about 97.5%, at least about 97.6%, at least about 97.7%, at least about 97.8%, at least about 97.9%, at least about 98%, at least about 98.1%, at least about 98.2%, at least about 98.3%, at least about 98.4%, at least about 98.5%, at least about 98.6%, at least about 98.7%, at least about 98.8%, at least about 98.9%, at least about 99%, at least about 99.1%, at least about 99.2%, at least about 99.3%, at least about 99.4%, at least about 99.5%, at least about 99.6%, at least about 99.7%, at least about 99.8%, at least about 99.8%, at least about 99.9%, at least about 99.95%, at least about 99.999%, at least about 99.9999%, at least about 99.99999%, at least about 99.999999% or more identical to that of the deposited strain.

According to a specific embodiment, the thrC nucleic acid sequence is at least about 97%, e.g., at least about 97.1%, at least about 97.2%, at least about 97.3%, at least about 97.4%, at least about 97.5%, at least about 97.6%, at least about 97.7%, at least about 97.8%, at least about 97.9%, at least about 98%, at least about 98.1%, at least about 98.2%, at least about 98.3%, at least about 98.4%, at least about 98.5%, at least about 98.6%, at least about 98.7%, at least about 98.8%, at least about 98.9%, at least about 99%, at least about 99.1%, at least about 99.2%, at least about 99.3%, at least about 99.4%, at least about 99.5%, at least about 99.6%, at least about 99.7%, at least about 99.8%, at least about 99.8%, at least about 99.9%, at least about 99.95%, at least about 99.999%, at least about 99.9999%, at least about 99.99999%, at least about 99.999999% or more identical to that of the deposited strain.

According to an additional or alternative embodiment the deposited strain and the functional homolog is characterized by substantially the same (+/−about 10%, 20%, 40%, 50%, 60% when tested under the same conditions) biochemical profiling (e.g., biochemical fingerprinting) using for example, the GEN III redox chemistry (BIOLOG Inc. 21124 Cabot Blvd. Hayward Calif., 94545, USA), which can analyze both Gram-negative and Gram-positive bacteria, for their ability to metabolize all major classes of biochemicals, in addition to determining other important physiological properties such as pH, salt, and lactic acid tolerance. Further details can be obtained in "Modern Phenotypic Microbial Identification", B. R. Bochner, Encyclopedia of Rapid Microbiological Methods, 2006, v.2, Ch. 3, pp. 55-73, which is incorporated herein by reference in its entirety.

Example 7 of the Examples section provides a metabolite analysis of the deposited strain.

According to an additional or alternative embodiment, the functional homolog is defined by a comparison of coding sequences (gene) order.

According to an additional or alternative embodiment, the functional homolog is defined by a comparison of order of non-coding sequences.

According to an additional or alternative embodiment, the functional homolog is defined by a comparison of order of coding and non-coding sequences.

According to some embodiments of the invention, the combined coding region of the functional homolog is such that it maintains the original order of the coding regions as within the genomic sequence of the bacterial isolate yet without the non-coding regions.

Coding sequences of the deposited strain and their annotations are provided in Table 5 of the Examples section which follows.

For example, in case the genomic sequence has the following coding regions, A, B, C, D, E, F, G, each flanked by non-coding sequences (e.g., regulatory elements, introns and the like), the combined coding region will include a single nucleic acid sequence having the A+B+C+D+E+F+G coding regions combined together while maintaining the original order of their genome, yet without the non-coding sequences.

According to some embodiments of the invention, the combined non-coding region of the functional homolog is such that it maintains the original order of the non-coding regions as within the genomic sequence of the bacterial isolate yet without the coding regions as originally present in the bacterial deposit.

According to some embodiments of the invention, the combined non-coding region and coding region (i.e., the genome) of the functional homolog is such that it maintains the original order of the coding and non-coding regions as within the genomic sequence of the microbial deposit.

As used herein "maintains" relate to at least about 90%, 91%, 92%, 93%, 94%, 95%, 96%, 97%, 98%, 99% or 100% is maintained as compared to the deposited strain.

According to an additional or alternative embodiment, the functional homolog is defined by a comparison of gene content.

According to a specific embodiment, the functional homolog comprises a combined coding region where at least about 90%, at least about 91%, at least about 92%, at least about 93%, at least about 94%, at least about 95%, at least about 96%, at least about 97%, at least about 98%, at least about 99%, or more (e.g., 100%) is identical to a combined coding region existing in genome of the deposited strain.

As used herein "combined coding region" refers to a nucleic acid sequence including all of the coding regions of the bacterial isolate yet without the non-coding regions of the bacterial isolate.

According to an additional or alternative embodiment, the functional homolog is defined by a comparison of nucleotide composition and codon usage.

According to an additional or alternative embodiment, the functional homolog is defined by a method based on random genome fragments and DNA microarray technology. These methods are of sufficiently high resolution to for strain-to-species level identification.

One of ordinary skill in the art, based on knowledge of the classification criteria would know how to identify strains that are considered functional homologs.

An additional and more detailed description of species-to-strain classification can be found in:

Cho and Tiedje 2001 Bacterial species determination from DNA-DNA hybridization by using genome fragments and DNA microarrays;

Coenye et al. 2005 Towards a prokaryotic genomic taxonomy. FEMS Microbiol. Rev. 29:147-167;

Konstantinidis and Tiedje (2005) Genomic insights that advance the species definition for prokaryotes. Proc. Natl. Acad. Sci. USA 102:189-197;

Konstantinidis et al. 2006 Toward a more robust assessment of intraspecies diversity using fewer genetic markers. Appl. Environ. Microbiol. 72:7286-7293.

It is to be understood that one or more methods as described herein can be used to identify a functional homolog.

Genomic data can be obtained by methods which are well known in the art e.g., DNA sequencing, bioinformatics, electrophoresis, an enzyme-based mismatch detection assay and a hybridization assay such as PCR, RT-PCR, RNase protection, in-situ hybridization, primer extension, Southern blot, Northern Blot and dot blot analysis.

According to a specific embodiment, the functional homolog and the deposited strain belong to the same species (Bacillus amyloliquefaciens).

According to a specific embodiment, the functional homolog and the deposited strain belong to the same subspecies.

As mentioned, the functional homolog is endowed with or maintains (as defined herein) the functional properties of the deposited strain.

Thus according to a specific embodiment, the bacterial strain has no lecithinase activity as determined by the absence of a white precipitate when the isolated bacterial strain or functional homolog of same is streaked out onto egg yolk agar and incubated for 24 h at 37° C.

According to an additional or an alternative embodiment, the bacterial strain exhibits gamma hemolytic activity when streaked onto 5% sheep blood agar and incubated for 24 h at 37° C.

According to an additional or an alternative embodiment, the bacterial strain is sensitive to an antibiotic selected from the group consisting of erythromycin, gentamicin, tetracycline, streptomycin, vancomycin, chloramphenicol, kanamycin and clindamycin according to the European Food Safety Authority MIC breakpoints for Bacillus species such as shown in Table 2 hereinbelow.

According to an additional or an alternative embodiment, the bacterial strain is incapable of colonizing a mammalian (e.g., murine) lung.

According to an additional or an alternative embodiment, the bacterial strain is growth inhibitory effects against bacteria and fungi, as shown in Tables 3 and 4, respectively.

According to an additional or an alternative embodiment, the bacterial strain exhibits a secreted metabolome composition as shown in the Examples section which follows. As used herein "isolated" refers to an isolate of bacteria in which the prevalence (i.e., concentration) of the bacterial stain or functional homolog is enriched over that (exceeds that) found in nature (e.g., in Doenjang, a fermented soybean paste). Thus, the present teachings refer to cultures, preparations, compositions (interchangeably used), which comprise the bacterial strain.

The isolated bacterial strain can be comprised in a composition, preparation, formulation, culture, article of manufacture.

According to some embodiments, the composition, preparation, formulation, culture, article of manufacture, comprises more than 1 microbial strains or species.

According to some embodiments, the composition, preparation, formulation, culture, article of manufacture, comprises 2 microbial strains or species.

According to some embodiments, the composition, preparation, formulation, culture, article of manufacture, comprises 3 microbial strains or species.

According to some embodiments, the composition, preparation, formulation, culture, article of manufacture, comprises 4 microbial strains or species.

According to some embodiments, the composition, preparation, formulation, culture, article of manufacture does not comprise more than 5 different species or strains of microbes.

According to some embodiments, the composition, preparation, formulation, culture, article of manufacture does not comprise more than 4 different species or strains of microbes.

According to some embodiments, the composition, preparation, formulation, culture, article of manufacture does not comprise more than 3 different species or strains of microbes.

According to some embodiments, the composition, preparation, formulation, culture, article of manufacture does not comprise more than 2 different species or strains of microbes.

According to some embodiments of the invention, the composition, preparation, formulation, culture, article of manufacture comprises less than 10 microbial species.

According to some embodiments of the invention, the composition, preparation, formulation, culture, article of manufacture comprises less than 9 microbial species.

According to some embodiments of the invention, the composition, preparation, formulation, culture, article of manufacture comprises less than 8 microbial species.

According to some embodiments of the invention, the composition, preparation, formulation, culture, article of manufacture comprises less than 7 microbial species.

According to some embodiments of the invention, the composition, preparation, formulation, culture, article of manufacture comprises less than 6 microbial species.

According to some embodiments of the invention, the composition, preparation, formulation, culture, article of manufacture comprises less than 5 microbial species.

According to some embodiments of the invention, the composition, preparation, formulation, culture, article of manufacture comprises 4 microbial species.

According to some embodiments of the invention, the composition, preparation, formulation, culture, article of manufacture comprises 3 microbial species.

According to some embodiments of the invention, the composition, preparation, formulation, culture, article of manufacture comprises 2 microbial species.

According to some embodiments of the invention, the composition, preparation, formulation, culture, article of manufacture comprises 3 microbial strains.

According to some embodiments of the invention, the composition, preparation, formulation, culture, article of manufacture comprises 2 microbial strains.

According to a specific embodiment of the invention, the composition, preparation, formulation, culture, article of manufacture comprises a single microbial species i.e., the isolated bacterial stain.

According to a specific embodiment, the composition, preparation, formulation, culture, article of manufacture comprises the bacterial strain at a level of purity of at least about 20%, at least about 30%, at least about 40%, at least about 50%, at least about 60%, at least about 70%, at least about 80%, at least about 85%, at least about 90%, at least about 91%, at least about 92%, at least about 93%, at least about 94%, at least about 95%, 96%, at least about, 97%.

According to a specific embodiment, the composition, preparation, formulation, culture, article of manufacture comprises the bacterial strain at a level of purity of at least about 98%, at least about 99%, at least about 99.1%, at least about 99.2%, at least about 99.3%, at least about 99.4%, at least about 99.5%, at least about 99.6%, at least about 99.7%, at least about 99.8%, at least about 99.9%, at least about 99.95%, at least about 99.99% or more, say 100% pure.

According to a specific embodiment, the microbial strain comprises viable (more than 50%) microbial cells.

As used herein "viable" refers to a microorganism that is alive and capable of regeneration and/or propagation, while in a vegetative, frozen, preserved, or reconstituted state.

According to a specific embodiment, the microbial strain comprises spores of the bacterial strain.

As used herein ""spores" or "endospores" refer to microbes that are generally viable, more resistant to environmental influences such as heat and bactericidal than other forms of the same bacterial species, and typically capable of germination and out-growth. Bacteria that are "capable of forming spores" are those bacteria comprising the genes and other necessary abilities to produce spores under suitable environmental conditions.

As used in herein, the term "CFUs" or "Colony Forming Units" refers to the number of microbial cells e.g., bacterial strain, in a defined sample (e g milliliter of liquid, gram of powder) that form colonies and thereafter numbered, on a semi-solid bacteriological growth medium.

According to specific embodiments, the enrichment in the composition, preparation, formulation, culture, article of manufacture is $10^2$ CFUs-$10^9$ CFUs/gr powder or $10^2$ CFUs-$10^9$ CFUs/ml.

According to specific embodiments, the enrichment in the composition, preparation, formulation, culture, article of manufacture is $10^2$ CFUs-$10^8$ CFUs/gr powder or $10^2$ CFUs-$10^8$ CFUs/ml.

According to specific embodiments, the enrichment in the composition, preparation, formulation, culture, article of manufacture is $10^2$ CFUs-$10^7$ CFUs/gr powder or $10^2$ CFUs-$10^7$ CFUs/ml.

According to specific embodiments, the enrichment in the composition, preparation, formulation, culture, article of manufacture is $10^2$ CFUs-$10^6$ CFUs/gr powder or $10^2$ CFUs-$10^6$ CFUs/ml.

According to specific embodiments, the enrichment in the composition, preparation, formulation, culture, article of According to a specific embodiment, the composition, preparation, formulation, culture, article of manufacture comprises the bacterial strain at a level of purity of $10^2$ CFUs-$10^5$ CFUs/gr powder or $10^2$ CFUs-$10^5$ CFUs/ml.

According to specific embodiments, the enrichment in the composition, preparation, formulation, culture, article of manufacture is $10^2$ CFUs-$10^4$ CFUs/gr powder or $10^2$ CFUs-$10^4$ CFUs/ml.

According to specific embodiments, the enrichment in the composition, preparation, formulation, culture, article of manufacture is $10^2$ CFUs-$10^3$ CFUs/gr powder or $10^2$ CFUs-$10^3$ CFUs/ml.

According to specific embodiments, the enrichment in the composition, preparation, formulation, culture, article of manufacture is $10^3$ CFUs-$10^9$ CFUs/gr powder or $10^3$ CFUs-$10^9$ CFUs/ml.

According to specific embodiments, the enrichment in the composition, preparation, formulation, culture, article of manufacture is $10^4$ CFUs-$10^9$ CFUs/gr powder or $10^4$ CFUs-$10^9$ CFUs/ml.

According to specific embodiments, the enrichment in the composition, preparation, formulation, culture, article of manufacture is $10^5$ CFUs-$10^9$ CFUs/gr powder or $10^5$ CFUs-$10^9$ CFUs/ml.

According to specific embodiments, the enrichment in the composition, preparation, formulation, culture, article of manufacture is $10^6$ CFUs-$10^9$ CFUs/gr powder or $10^6$ CFUs-$10^9$ CFUs/ml.

According to specific embodiments, the enrichment in the composition, preparation, formulation, culture, article of manufacture is $10^7$ CFUs-$10^9$ CFUs/gr powder or $10^7$ CFUs-$10^9$ CFUs/ml.

According to specific embodiments, the enrichment in the composition, preparation, formulation, culture, article of manufacture is $10^8$ CFUs-$10^9$ CFUs/gr powder or $10^8$ CFUs-$10^9$ CFUs/ml.

According to specific embodiments, the enrichment in the composition, preparation, formulation, culture, article of manufacture is $10^8$ CFUs-$10^9$ CFUs/gr powder or $10^8$ CFUs-$10^9$ CFUs/ml.

According to a specific embodiment the composition, preparation, formulation, culture, article of manufacture comprises at least about 100 CFUs or spores, at least about $10^2$ CFUs/gr or CFUs/ml, at least about $10^2$ CFUs/gr or CFUs/ml, at least about $10^3$ CFUs/gr or CFUs/ml, at least about $10^4$ CFUs/gr or CFUs/ml, at least about $10^5$ CFUs/gr or CFUs/ml, at least about $10^6$ CFUs/gr or CFUs/ml, at least about $10^7$ CFUs/gr or CFUs/ml, at least about $10^8$ CFUs/gr or CFUs/ml, at least about $10^9$ CFUs/gr or CFUs/ml, at least about $10^{10}$ CFUs/gr or CFUs/ml, at least about $10^{11}$ CFUs/gr or CFUs/ml, at least about $10^{12}$ CFUs/gr or CFUs/ml.

According to a specific embodiment the composition, preparation, formulation, culture, article of manufacture (especially for a liquid formulation) comprises at least about $10^6$ CFUs/gr or CFUs/ml, at least about $10^7$ CFUs/gr or CFUs/ml, at least about $10^8$ CFUs/gr or CFUs/ml, at least about $10^9$ CFUs/gr or CFUs/ml.

According to a specific embodiment the composition, preparation, formulation, culture, article of manufacture (especially for a dry formulation) comprises at least about $10^8$ CFUs/gr or CFUs/ml, at least about $10^9$ CFUs/gr or CFUs/ml, at least about $10^{10}$ CFUs/gr or CFUs/ml, at least about $10^{11}$ CFUs/gr or CFUs/ml, at least about $10^{12}$ CFUs/gr or CFUs/ml.

According to a specific embodiment, the composition, preparation, formulation, culture, article of manufacture is selected from the group consisting of a still culture, whole cultures stored stock of cells (particularly glycerol stocks), agar strip, stored agar plug in glycerol/water, freeze dried stock, and dried stocks such as lyophilisate dried onto filter paper.

According to a specific embodiment, the composition, preparation, culture or formulation is devoid of animal contaminants to render it safe for human use.

As used herein "a culture" refers to a fluid, pellet, scraping, dried sample, lyophilisate or a support, container, or medium such as a plate, paper, filter, matrix, straw, pipette or pipette tip, fiber, needle, gel, swab, tube, vial, particle, etc. that contains the deposited strain or the functional homolog thereof in an amount that exceeds that found in nature, as described hereinabove. In the present invention, an isolated culture of a microbial strain is a culture fluid or a scraping, pellet, dried composition, preparation, formulation, culture, article of manufacture, lyophilisate, or a support, container, or medium that contains the microorganism, in the absence of other organisms (or in combination with other microbes which were preselected and grown for the purpose of combined administration).

According to a specific embodiment, the bacterial strain within the composition, preparation, formulation, culture, article of manufacture is viable.

The bacterial strain can be produced or manufactured using methods which are well known in the art of microbiology.

According to a specific embodiment, the microbial strain is isolated from Doenjang, such as by using Luria Bertani Miller agar (BD, Difco) agar for plating. According to a specific embodiment, representative colonies are picked from plates with the highest dilution still showing colonies.

After purification, the strain was stored at −80° C. The stock culture is propagated in LB Miller broth.

According to an aspect, the bacterial strain is cultured under conditions that allow propagation; after which (and/or during which) the bacterial strain is harvested.

Thus, according to some embodiments, cultures of the microbial strain may be prepared using standard static drying and liquid fermentation techniques known in the art. Growth is commonly effected in a bioreactor.

A bioreactor refers to any device or system that supports a biologically active environment. As described herein a bioreactor is a vessel in which microorganisms including the microorganism of the invention can be grown. A bioreactor may be any appropriate shape or size for growing the microorganisms. A bioreactor may range in size and scale from 10 mL (e.g., small scale) to liter's to cubic meters (e.g., large scale) and may be made of stainless steel, disposable material (e.g., nylon, plastic bags) or any other appropriate material as known and used in the art. The bioreactor may be a batch type bioreactor, a fed batch type or a continuous-type bioreactor (e.g., a continuous stirred reactor). For example, a bioreactor may be a chemostat as known and used in the art of microbiology for growing and harvesting microorganisms. A bioreactor may be obtained from any commercial supplier (See also Bioreactor System Design, Asenjo & Merchuk, CRC Press, 1995).

For small scale operations, a batch bioreactor may be used, for example, to test and develop new processes, and for processes that cannot be converted to continuous operations.

Microorganisms grown in a bioreactor may be suspended or immobilized. Growth in the bioreactor is generally under aerobic conditions at suitable temperatures and pH for growth. For the organisms of the invention, cell growth can be achieved at temperatures between 5-40° C., with an exemplary temperature range selected from 20 to 10° C., 15 to 28° C., 20 to 30° C., or 15 to 25° C. The pH of the nutrient medium can vary between 4.0 and 9.0. For example, the operating range can be usually slightly acidic to neutral at pH 5.0 to 8.5, or 4.5 to 6.5, or pH 5.0 to 6.0.

According to a specific embodiment, the cell growth is achieved at 20-40° C. at pH of 5.0-8.5.

Typically, maximal cell yield is obtained in 20-72 hours after inoculation. By virtue of the conditions applied in the selection process and general requirements of most microorganisms, a person of ordinary skill in the art would be able to determine essential nutrients and conditions. The microorganisms would typically be grown in aerobic liquid cultures on media which contain sources of carbon, nitrogen, and inorganic salts that can be assimilated by the microorganism and supportive of efficient cell growth. Exemplary carbon sources are hexoses such as glucose, but other sources that are readily assimilated such as amino acids, may be substituted. Many inorganic and proteinaceous materials may be used as nitrogen sources in the growth process. Exemplary nitrogen sources are amino acids and urea but others include gaseous ammonia, inorganic salts of nitrate and ammonium, vitamins, purines, pyrimidines, yeast extract, beef extract, proteose peptone, soybean meal, hydrolysates of casein, distiller's solubles, and the like. Among the inorganic minerals that can be incorporated into the nutrient medium are the customary salts capable of yielding calcium, zinc, iron, manganese, magnesium, copper, cobalt, potassium, sodium, molybdate, phosphate, sulfate, chloride, borate, and like ions.

The culture can be a pure culture, whereby a single microbial strain is included or a mixed culture. This is of course pending the compliance of the microbial strains to co-exist and proliferate under the same culturing conditions. When needed, an antibiotic or other growth-restricting conditions can be employed during culturing to restrict the growth of other microorganisms (contaminants) not desired in the culture/co-culture e.g., temperature, essential nutrients and the like.

According to an alternative or an additional embodiment, the desired combination is produced following culturing, such as when the microbial strains do not share the same or optimal culturing conditions.

The ratio of each type of microorganism in the final product will depend on the intended use (some are listed hereinbelow).

According to a specific embodiment the ration between the B. amyloliquefaciens 298, B. subtilis 3 and B. subtilis 281 strains is 10:1:1.

According to a specific embodiment the ration between the B. amyloliquefaciens 298, B. subtilis 3 and B. subtilis 281 strains is 1:1:10.

According to a specific embodiment the ration between the B. amyloliquefaciens 298, B. subtilis 3 and B. subtilis 281 strains is 1:10:1.

According to a specific embodiment the ration between the B. amyloliquefaciens 298, B. subtilis 3 and B. subtilis 281 strains is 1:10:10.

According to a specific embodiment the ration between the B. amyloliquefaciens 298, B. subtilis 3 and B. subtilis 281 strains is 10:10:1.

According to a specific embodiment the ration between the B. amyloliquefaciens 298, B. subtilis 3 and B. subtilis 281 strains is 10:1:10.

According to a specific embodiment the ration between the B. amyloliquefaciens 298, B. subtilis 3 and B. subtilis 281 strains is 5:1:1.

According to a specific embodiment the ration between the B. amyloliquefaciens 298, B. subtilis 3 and B. subtilis 281 strains is 1:1:5.

According to a specific embodiment the ration between the B. amyloliquefaciens 298, B. subtilis 3 and B. subtilis 281 strains is 1:5:1.

According to a specific embodiment the ration between the B. amyloliquefaciens 298, B. subtilis 3 and B. subtilis 281 strains is 1:5:5.

According to a specific embodiment the ration between the B. amyloliquefaciens 298, B. subtilis 3 and B. subtilis 281 strains is 5:5:1.

According to a specific embodiment the ration between the B. amyloliquefaciens 298, B. subtilis 3 and B. subtilis 281 strains is 5:1:5.

According to a specific embodiment the ration between the B. amyloliquefaciens 298, B. subtilis 3 and B. subtilis 281 strains is 2:1:1.

According to a specific embodiment the ration between the B. amyloliquefaciens 298, B. subtilis 3 and B. subtilis 281 strains is 1:1:2.

According to a specific embodiment the ration between the B. amyloliquefaciens 298, B. subtilis 3 and B. subtilis 281 strains is 1:2:1.

According to a specific embodiment the ration between the B. amyloliquefaciens 298, B. subtilis 3 and B. subtilis 281 strains is 1:2:2.

According to a specific embodiment the ration between the B. amyloliquefaciens 298, B. subtilis 3 and B. subtilis 281 strains is 2:2:1.

According to a specific embodiment the ration between the *B. amyloliquefaciens* 298, *B. subtilis* 3 and *B. subtilis* 281 strains is 2:1:2.

According to a specific embodiment the ration between the *B. amyloliquefaciens* 298, *B. subtilis* 3 and *B. subtilis* 281 strains is 1:1:1.

The identity of the microorganism(s) in the culture can be experimentally validated at the nucleic acid level, protein level, metabolite levels, functional level and/or by using classical microbiology tools, e.g., streaking (e.g., with selection).

After production, the microbial strain can be stored or used fresh, either as is or subject to further formulation.

Also contemplated herein are a lysate and/or a fermentation product of the above described methods. Methods of cell lysis of bacterial strains e.g., of the species *B. amyloliquefaciens* are well known in the art.

The formulation of the microbial strain much depends on the intended use. Following is a non-limiting description of various formulations that can be used along with the present teachings.

According to a specific embodiment, the bacterial strain is formulated in a liquid formulation.

According to a specific embodiment, the bacterial strain is formulated in a dry formulation.

According to a specific embodiment, the bacterial strain is formulated in a gel formulation.

Microbial strains formulations used to reduce the incidence of pathogenic microorganisms (bacteria and/or fungi), can be in vivo administered, can be released into the air or in conjunction with an HVAC system, applied to waste, food products, food processing areas, food preparation tools, agricultural products, agricultural water (irrigation water, agricultural soils, agricultural crops) and the like. The formulations of bacteria described herein can be applied in a powder, liquid, foam, gelled, aerosol or solid form. In liquid formulations, the microbial strain formulations may be dispensed from conventional dispensing devices, including pump sprayers, aerosol containers, squirt bottles etc. For application over larger areas, hoses, sprinkler systems or other suitable devices may be used. In the alternative, the formulations can be applied as a dry powder such as lyophilized bacteria or using any of the techniques currently known to a person of skill in the art. The optimal frequency of applications of the microbial strain formulations may depend on the target on which the formulation is to be applied. In certain embodiments, wherein formulations are contemplated, a microorganism is harvested and concentrated using a method that does not markedly decrease the viable cell concentration through centrifugation or filtration.

In embodiments wherein formulations are contemplated for preservation, such preservation may include a process of freezing, freeze-drying and/or spray-drying.

In certain embodiments, the preserved cells can be used in a microbial-based product. The preserved bacterial strain can be provided "as-is" without further dilution or modification. Additionally, in certain embodiments, the bacterial strain can be mixed with a carrier to dilute the concentration of cells to an appropriate concentration for administration. The carrier can be as simple as one element, or a more complex molecule or mixture of molecules in any proportion in order to act as a suitable carrier. This carrier and composition may, in certain instances, have defined properties such as solubility in water or other media. The diluting carrier can be of any composition or combination including but not limited to: lactose, glucose, non-fat dry milk powder, oligosaccharides, glycerol, oil, lecithin, or other materials.

In particular formulations, other chemicals or materials may be used to reduce or absorb moisture and/or oxygen for further protection and preservation of the viable microbial cells. Such chemicals or materials include, but are not limited to: calcium stearate, sodium aluminosilicate, sodium sulfide, sodium carbonate, silica, iron oxides, calcium carbonate, zeolite, bicarbonates, sodium sulfate, silicon dioxide and other silica materials.

In certain embodiments, a microbial strain formulation for administration to a subject or a surface or other target can include a preservation matrix, which contains and preserves the culture. Such a matrix may include a biologically active binding agent, an antioxidant, a polyol, a carbohydrate and a proteinaceous material.

Antioxidants included in a preservation matrix may be provided to retard oxidative damage to the microbial cells during the preservation and storage process.

Polyols (i.e., polyhydric alcohols) included in a preservation matrix may be provided to maintain the native, uncollapsed state of cellular proteins and membranes during the preservation and storage process. In particular, polyols interact with the cell membrane and provide support during the dehydration portion of the preservation process. Examples of polyols include, but are not limited to xylitol, adonitol, glycerol, dulcitol, inositol, mannitol, sorbitol and/or arabitol.

Carbohydrates included in a preservation matrix may be provided to maintain the native, uncollapsed state of cellular proteins and membranes during the preservation and storage process. In particular, carbohydrates provide cell wall integrity during the dehydration portion of the preservation process. Exemplary carbohydrates include, but are not limited to dextrose, lactose, maltose, sucrose, fructose and/or any other monosaccharide, disaccharide or polysaccharide.

A proteinaceous material included in a preservation matrix may provide further protection of the microbial cell during the dehydration portion of the preservation process. Exemplary proteinaceous materials include, but are not limited to skim milk and albumin.

The microbial cells can be preserved within a preservation matrix including coating the cell matrix suspension onto an inert carrier e.g., a maltodextrin bead. The coated beads can then be dried, e.g., by a fluid bed drying method. Fluid bed drying methods are well known in the art. The coated beads can be stored as a powder, placed into gelatin capsules, or pressed into tablets.

In other formulations, the microbial strain contemplated can be formulated as a hard gelatin capsule. Gelatin capsules are commercially available and are well known in the art. In this embodiment, the method further comprises dispensing the cell suspension matrix to a gelatin capsule, chilling the gelatin capsule until the cell suspension matrix forms a non-fluid matrix and to affix the gel to the interior wall of the gelatin capsule, and desiccating the gelatin capsule in a desiccation chamber. Further examples of embodiments of preservation matrices and gelatin capsule formulations may be found in U.S. Pat. No. 6,468,526 which is herein incorporated by reference in its entirety.

In certain applications, the microbial strain may be placed in a microencapsulation formulation. Such microencapsulation formulations may have applicability for example in administration to subjects via oral, nasal, rectal, vaginal or urethral routes. Spray drying is the most commonly used microencapsulation method in the food industry, is economical and flexible, and produces a good quality product. The process involves the dispersion of the core material into a polymer solution, forming an emulsion or dispersion, followed by homogenisation of the liquid, then atomisation of the mixture into the drying chamber. This leads to evaporation of the solvent (water) and hence the formation of matrix type microcapsules.

Examples of microencapsulation can be found for example in U.S. Pat. No. 5,641,209 that is herein incorporated by reference.

An embodiment of preserving by freezing is to prepare frozen beads or pellets comprising the microbial strain. After a suitable fermentation, the liquid is removed from the viable bacteria by a method including but not limited to centrifugation, ultrafiltration, or sedimentation. An additive compound may be added to the bacteria prior to freezing. Suitable additives include but are not limited to, lactose, sucrose, trehalose, maltodextrin, cyclodextrin, spray gum, fish gelatin bloom, and maltitol.

Suitable additives may also serve as cryoprotective agents to improve the stability of the frozen culture. Cryoprotective agents include, but are not limited to, proteins, protein hydrosolates, carbohydrates, or a compound involved in the biosynthesis of nucleic acids. U.S. Publ. Appl. 20070254353. Proteins or protein hydrolysates include but are not limited to, malt extract, milk powder, whey powder, yeast extract, gluten, collagen, gelatin, elastin, keratin, or albumin. Carbohydrates include but are not limited to pentoses (e.g. ribose, xylose), hexoses (e.g. fructose, mannose, sorbose), disaccharides (e.g. sucrose, trehalose, melibiose, lactulose), oligosaccharides (e.g. raffinose), oligofrutoses (e.g. actilight, fribroloses), polysaccharides (e.g. maltodextrins, xanthan gum, pectin, alginate, microcrystalline cellulose, dextran, PEG), and sugar alcohols (sorbitol, manitol). U.S. Publ. Appl. 20070254353.

A foam is defined herein is a composition that is formed by trapping many gas bubbles in a liquid. Methods pertaining to the formulation and administration of foams are set forth in U.S. Pat. Nos. 4,112,942, 5,652,194, 6,140,355, 6,258,374, and 6,558,043, each of which is herein specifically incorporated by reference in its entirety.

A typical foam formulation may, for example, be constructed by introducing a gas into a gel or aqueous pharmaceutical composition such that bubbles of the gas are within the pharmaceutical composition.

A microbial strain formulation can be applied to a surface or simply to the air using an electrostatic spray apparatus. This apparatus should have a chamber for containing the microbial strain formulation and an opening in fluid connection with the chamber through which the microbial strain formulation can be dispensed and deposited on a desired surface. The apparatus should allow for electrically charging the microbial strain formulation. For example, a conductor can be used to connect the chamber to a voltage power source. One of skill in the art would be aware of other suitable devices that can function as such a conductor.

To apply the formulation to a surface or to the air, the formulation is placed into the chamber of the electrostatic spray apparatus. The microbial strain formulation can be pumped into the chamber. When the microbial strain formulation is placed into the chamber, it contacts the conductor, such as a high-voltage DC electrode, and becomes charged. Once the formulation in the chamber is charged, it carries the same charge as the conductor. As a result the formulation and conductor repel each other. This repulsive force discharges the microbial strain formulation through the opening of the nozzle to create streams of droplets. Therefore, no additional gas source is required for atomization of the coating formulation. Accordingly, a cloud of highly charged, highly uniform-sized droplets can be formed.

Since the droplets that are formed carry a charge, when they are deposited on a grounded surface, they will be guided by their electrostatic attraction to the grounded and hence electrically neutral surface. Since the droplets carry the same electrical charge, they will repel each other. This repulsion causes the droplets arriving at the surface to avoid the areas where other droplets have already been deposited and instead land on areas of the surface that have not been coated. In this way, an inherently uniform coating is formed.

One example of a suitable nozzle apparatus that can be used in the method of some embodiments of the invention is an apparatus for electrohydrodynamic spray-coating that is disclosed in U.S. Pat. No. 4,749,125. This apparatus has a metal shim that is placed within the nozzle apparatus to define a plurality of nozzle openings. The metal shim is also connected to a voltage source that allows for the formation of electrically charged droplets of coating formulation. Aerosol dispending system and automated embodiments thereof are further described hereinbelow.

Lyophilization—Dry microorganism cultures may be prepared according to methods which are well known in the art. In addition to constituents present in the culture medium, the medium may comprise at least one matrix material with or without other stabilizing substances. These materials may be selected from inorganic salts or buffers, at least one other compound which is selected from mono-, oligo- and polysaccharides, polyols, polyethers, amino acids, oligo- and polypeptides, milk-derived compounds, organic carboxylic acids, mineral compounds, organic carrier materials such as wheat semolina bran, alginates, DMSO, PVP (polyvinylpyrrolidone), CMC (carboxymethylcellulose), alpha-tocopherol, beta.-carotene and mixtures thereof.

Examples of suitable saccharide carrier components are sucrose, fructose, maltose, dextrose, lactose and maltodextrin. An example of a suitable polyol is glycerol. Examples of suitable amino acids are glutamic acid, aspartic acid and the salts thereof. An example of a suitable peptide carrier is peptone. An example of a milk-derived compound is sweet whey powder. Suitable organic carboxylic acids are, for example, citric acid, malic acid and L-ascorbic acid. Examples of suitable mineral carriers are montmorillonite and palygorskite.

The microorganism suspension containing the carrier can be dried in various ways. Suitable drying processes are in principle freeze drying, fluidized-bed drying and, spray-drying. Spray-drying also comprises modified spray-drying processes, such as spray-agglomeration or agglomerating spray-drying. The latter process is also known under the name FSD (fluidized spray-dryer) process.

Freeze-drying for preparing dry microorganism cultures according to some embodiments of the present invention can be carried out, for example, on the basis of the freeze-drying process described in U.S. Pat. No. 3,897,307, the contents of which is incorporated completely by reference.

Another drying process contemplated for use according to some embodiments of the present invention is spray-drying. Those methods which can be used according to some embodiments of the present invention are essentially all spray-drying techniques known in the art. The material to be sprayed can, for example, be dried concurrently or countercurrently; spraying can be carried out by means of a single-component or multiple-component nozzle or by means of an atomizer wheel.

The drying process according to some embodiments of the present invention may be carried out in such a manner that a very low residual moisture content is present in the dry material. The percentage water content is typically from about 2 to 3% by weight. This may be achieved by adding a post-drying step subsequently to the spray-drying step. The drying material is, for example, post-dried in a fluidized bed, such as at a temperature in the range of from 15 to 50° C., for a period of, for example, from 15 minutes to 20 hours. Conditioned compressed air or conditioned nitrogen serves as drying gas.

Instead of the above-described physical post-drying processes, it is also conceivable to add specific desiccants to the dry material obtained from the spray-drying. Examples of suitable desiccants are inorganic salts, such as calcium chloride and sodium carbonate, organic polymers, such as the product obtainable under the trade name Kollidion 90 F, and silicon-dioxide-containing desiccants, such as silica gel, zeolites and desiccants which are obtainable under the trade name Tixosil 38, Sipernat 22 S or Aerosil 200.

In certain embodiments, the microbial; strain may be refrigerated after harvesting and concentrating. In certain embodiments, after a suitable fermentation, the liquid is removed from the viable bacteria by a method including but not limited to centrifugation, ultrafiltration, or sedimentation. An additive compound may be added to the bacteria prior to refrigeration. Suitable additives include but are not limited to, lactose, sucrose, trehalose, maltodextrin, cyclodextrin, spray gum, fish gelatin bloom, and maltitol.

Suitable additives may also serve as cryoprotective agents to improve the stability of the refrigerated culture. Cryoprotective agents include, but are not limited to, proteins, protein hydrolosates, carbohydrates, or a compound involved in the biosynthesis of nucleic acids. U.S. Publ. Appl. 20070254353. Proteins or protein hydrolysates include but are not limited to, malt extract, milk powder, whey powder, yeast extract, gluten, collagen, gelatin, elastin, keratin, or albumin. Carbohydrates include but are not limited to pentoses (e.g. ribose, xylose), hexoses (e.g. fructose, mannose, sorbose), disaccharides (e.g. sucrose, trehalose, melibiose, lactulose), oligosaccharides (e.g. raffinose), oligofrutoses (e.g. actilight, fribroloses), polysaccharides (e.g. maltodextrins, xanthan gum, pectin, alginate, microcrystalline cellulose, dextran, PEG), and sugar alcohols (sorbitol, manitol). U.S. Publ. Appl. 20070254353.

The type of formulation depends on the intended use.

It will be appreciated that the present inventors have identified for the first time certain activities of the bacterial strain *Bacillus amyloliquefaciens*. This bacterial strain was found effective and safe for use in the treatment of respiratory tract infections.

As used herein, the term "treating" includes abrogating, substantially inhibiting, slowing or reversing the progression of a condition, substantially ameliorating clinical or other symptoms of a condition or substantially preventing the appearance of clinical or other symptoms of a condition.

Thus, according to an aspect of the invention there is provided a method of controlling a population of pathogenic bacteria and/or fungi in a respiratory system, the method comprising administering to a subject in need thereof an effective amount of bacteria of the species *Bacillus amyloliquefaciens* or any composition comprising same such as described herein, thereby controlling the population of pathogenic bacteria and/or fungi in the respiratory system.

As used herein "*Bacillus amyloliquefaciens*" refers to a bacterial species in the genus *Bacillus*. It is a gram positive soil bacteria closely related to the species *Bacillus subtilis*. According to a specific embodiment strains of this bacterial species are as described herein, e.g., *Bacillus amyloliquefaciens* 298 and functional homologs thereof.

According to an aspect of the invention there is provided a method of controlling a population of pathogenic bacteria and/or fungi, the method comprising providing an effective amount of the isolated bacterial strain or functional homolog of same or the composition such as described herein, thereby controlling the population of pathogenic bacteria and/or fungi.

As used herein "controlling" refers to preventing or reducing microbial infections such as a bacterial or fungal infection or inhibiting the rate and extent of such infection. Therapeutic treatment is also contemplated.

According to a specific embodiment, the controlling is prevention of an infection.

As described hereinbelow, the present inventors identified the use of the bacterial strain as described herein in controlling various species of microbes.

Thus, according to some embodiments, the present compositions and methods are useful in controlling *E. coli*.

*Escherichia coli* is a Gram-negative, facultatively anaerobic, rod-shaped, coliform bacterium of the genus *Escherichia* that is commonly found in the lower intestine of warm-blooded organisms. Some *E. coli* serotypes can cause serious food poisoning in their hosts, and are occasionally responsible for product recalls due to food contamination. It is most abundant in food and water supply and industrial sites (e.g., paper production).

According to some additional or alternative embodiments, the present compositions and methods are useful in controlling *Pseudomonas aeruginosa*.

*Pseudomonas aeruginosa* is a common Gram-negative, rod-shaped bacterium that can cause disease in plants and animals, including humans. It is the most common cause of infections of burn injuries and of the outer ear (otitis externa), and is the most frequent colonizer of medical devices (e.g., catheters). *Pseudomonas* can be spread by equipment that gets contaminated and is not properly cleaned or on the hands of healthcare workers. *Pseudomonas* can cause community-acquired pneumonias, as well as ventilator-associated pneumonias, being one of the most common agents isolated in several studies. One in ten hospital-acquired infections is from *Pseudomonas*. Cystic fibrosis patients are also predisposed to *P. aeruginosa* infection of the lungs. *P. aeruginosa* may also be a common cause of "hot-tub rash" (dermatitis), caused by lack of proper, periodic attention to water quality. Since these bacteria like moist environments, such as hot tubs and swimming pools, they can cause skin rash or swimmer's ear. *Pseudomonas* is also a common cause of postoperative infection in radial keratotomy surgery patients. The organism is also associated with the skin lesion ecthyma gangrenosum. *P. aeruginosa* is frequently associated with osteomyelitis involving puncture wounds of the foot, believed to result from direct inoculation with *P. aeruginosa* via the foam padding found in tennis shoes, with diabetic patients at a higher risk.

According to some additional or alternative embodiments, the present compositions and methods are useful in controlling *Bacillus cereus*.

*Bacillus cereus* is a Gram-positive, rod-shaped, aerobic, facultatively anaerobic, motile, beta hemolytic bacterium commonly found in soil and food. Some strains are harmful to humans and cause foodborne disease. *Bacillus* foodborne diseases occur due to survival of the bacterial endospores when food is improperly cooked. Cooking temperatures less than or equal to 100° C. (212° F.) allow some *B. cereus* spores to survive. This problem is compounded when food is then improperly refrigerated, allowing the endospores to germinate.

According to some additional or alternative embodiments, the present compositions and methods are useful in controlling *Staphylococcus aureus*.

*Staphylococcus aureus* is a Gram-positive, round-shaped bacterium that is a member of the Firmicutes, and it is a member of the normal flora of the body, frequently found in the nose, respiratory tract, and on the skin. It is often positive for catalase and nitrate reduction and is a facultative anaerobe that can grow without the need for oxygen. It is a common cause of skin infections including abscesses, respiratory infections such as sinusitis, and food poisoning. Pathogenic strains often promote infections by producing virulence factors such as potent protein toxins, and the expression of a cell-surface protein that binds and inactivates antibodies. The emergence of antibiotic-resistant strains of *S. aureus* such as methicillin-resistant *S. aureus* (MRSA) is a worldwide problem in clinical medicine. Despite much research and development there is no approved vaccine for *S. aureus*. Spread of *S. aureus* (including MRSA) generally is through human-to-human contact, although recently some veterinarians have discovered the infection can be spread through pets. Recently, myriad cases of *S. aureus* have been reported in hospitals across America. Transmission of the pathogen is facilitated in medical settings where healthcare worker hygiene is insufficient. *S. aureus* is an incredibly hardy bacterium, as was shown in a study where it survived on polyester for just under three months; polyester is the main material used in hospital privacy curtains. The bacteria are transported on the hands of healthcare workers, who may pick them up from a seemingly healthy patient carrying a benign or commensal strain of *S. aureus*, and then pass it on to the next patient being treated. Introduction of the bacteria into the bloodstream can lead to various complications, including endocarditis, meningitis, and, if it is widespread, sepsis.

According to some additional or alternative embodiments, the present compositions and methods are useful in controlling *Salmonella typhimurium*.

*Salmonella typhimurium*. is a serogroup of a rod-shaped, flagellated, facultative anaerobic, Gram-negative bacterium and a member of the genus *Salmonella*. It is a serovar that is a serious human pathogen. The encounter of humans to *S. typhimurium* is made via fecal-oral route from infected individuals or animals to healthy ones, with food as a common vector. Poor hygiene of patients shedding the organism can lead to secondary infection, as well as consumption of shellfish from polluted bodies of water. Most common source of infection, however, are food of animal origin and drinking water tainted by urine and feces of infected individuals and animals.

According to some additional or alternative embodiments, the present compositions and methods are useful in controlling *Alternaria alternata*.

*Alternaria alternata* is a fungus which has been recorded causing leaf spot and other diseases on over 380 host species of plant. It is an opportunistic pathogen on numerous hosts causing leaf spots, rots and blights on many plant parts. In order to survive, *Alternaria alternata* needs a moist warm environment. It is often found in areas with humid climates, or where there has been significant rainfall. The fungus lives in seeds and seedlings, and is also spread by spores. This disease flourishes in dead plants that have been left in gardens over winter. Additionally, when dead infected debris is added to compost pile it can spread to other vegetables throughout the garden.

According to some additional or alternative embodiments, the present compositions and methods are useful in controlling *Cladosporium sphaerospermum*.

*Cladosporium sphaerospermum* is a fungus belonging to the genus *Cladosporium*. *Cladosporium sphaerospermum* is mainly known as a spoilage agent of harvested fruits and vegetables. *Cladosporium sphaerospermum* is a cosmopolitan fungus that inhabits city buildings and the environment and because of its airborne nature it can move rapidly between locations. *Cladosporium sphaerospermum* is also been shown to inhabit paint films on walls and other surfaces as well as old paintings. This fungus is also able to grow on gypsum-based material with and without paint and wallpaper. Plant materials that are affected include citrus leaves on various other decaying plant leaves, on the stems of herbaceous and woody plants, on fruits and vegetables. The fungus has also been reported from wheat-based bakery items.

According to some additional or alternative embodiments, the pathogenic bacteria and/or fungi are airborne pathogens that typically cause inflammation in the respiratory system e.g., nose, throat, sinuses and the lungs.

Examples of severe infections caused by airborne bacteria include, but are not limited to tuberculosis, pneumonia, and legionellosis.

As mentioned, according to some embodiments, the methods described herein are directed to controlling a population of pathogenic bacteria and/or fungi in a respiratory system which may cause a respiratory tract disease.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

In one embodiment, the composition according to the present invention may be administered in an aerosol, for example by way of a nasal spray, for instance for administration to the respiratory tract.

As used herein the term “respiratory tract disease” refers to diseases of the upper and/or lower respiratory tracts. The term disease as used herein is synonymous with the term disorder.

In one embodiment the respiratory tract disease is an upper respiratory tract disease.

Upper respiratory tract diseases include, for example, one or more of throat soreness, sneezing, blocked nose, runny nose or a cough is a symptom of one or more of the group consisting of: tonsillitis, otitis media rhinitis (inflammation of the nasal mucosa); rhinosinusitis or sinusitis (inflammation of the nares and paranasal sinuses, including frontal, ethmoid, maxillary, and sphenoid); nasopharyngitis, rhinopharyngitis or the common cold (inflammation of the nares, pharynx, hypopharynx, uvula, and tonsils); pharyngitis (inflammation of the pharynx, hypopharynx, uvula, and tonsils); epiglottitis or supraglottitis (inflammation of the superior portion of the larynx and upraglottic area); laryngitis (inflammation of the larynx); laryngotracheitis (inflammation of the larynx, trachea, and subglottic area); and tracheitis (inflammation of the trachea and subglottic area).

In one embodiment the respiratory tract disease is a lower respiratory tract disease.

Lower respiratory tract diseases include, for example, bronchitis, acute bronchitis, pneumonia, lung abscesses.

According to some embodiments, the present teachings are directed at controlling pathogenic microbes which include, but are not limited to, *Salmonella Typhimurium, Salmonella enterica, Salmonella enteritidis, Clostridium botulinum, Staphylococcus aureus, Campylobacter jejuni, Yersinia enterocolitica* and *Yersinia pseudotuberculosis, Vibrio cholerae* O1, *Vibrio cholerae* non-O1, *Vibrio parahaemolyticus* and other *Vibrio* spp., *Vibrio vulnificus, Clostridium perfringens, Bacillus cereus, Aeromonas hydrophila, Plesiomonas shigelloides, Shigella* spp., miscellaneous enteric pathogens, and *Streptococcus* spp.

According to some embodiments the diseases caused by the pathogenic microbes include, but are not limited to, staphylococcal infections (caused, for example, by *Staphylococcus aureus, Staphylococcus epidermidis,* or *Staphylococcus saprophyticus*), streptococcal infections (caused, for example, by *Streptococcus pyogenes, Streptococcus pneumoniae,* or *Streptococcus agalactiae*), enterococcal infections (caused, for example, by *Enterococcus faecalis*) diphtheria (caused, for example, by *Corynebacterium diptheriae*), anthrax (caused, for example, by *Bacillus anthracis*), listeriosis, gangrene (caused, for example, by *Clostridium perfringens*), tetanus (caused, for example, by *Clostridium tetani*), botulism (caused, for example, by *Clostridium botulinum*), toxic enterocolitis (caused, for example, by *Clostridium difficile*), bacterial meningitis (caused, for example, by *Neisseria meningitidis*), bacteremia (caused, for example, by *Neisseria gonorrhoeae*), *E. coli* infections (colibacilliocis), including urinary tract infections and intestinal infections, shigellosis (caused, for example, by *Shigella* species), *salmonellosis* (caused, for example, by *Salmonella* species), *yersinia* infections (caused, for example, by *Yersinia pestis, Yersinia pseudotuberculosis,* or *Yersinia enterocolitica*), cholera (caused, for example, by *Vibrio cholerae*), campylobacteriosis (caused, for example, by *Campylobacter jejuni* or *Campylobacter fetus*), gastritis (caused, for example, by *Helicobacter pylori*), *pseudomonas* infections (caused, for example, by *Pseudomonas aeruginosa* or *Pseudomonas mallei*), *Haemophilus influenzae* type B (HIB) meningitis, HIB acute epiglottitis, or HIB cellulitis (caused, for example, by *Haemophilus influenzae*), pertussis (caused, for example, by *Bordetella pertussis*), *mycoplasma* pneumonia (caused, for example, by *Mycoplasma pneumoniae*), nongonococcal urethritis (caused, for example, by *Ureaplasma urealyticum*), legionellosis (caused, for example, by *Legionella pneumophila*), syphillis (caused, for example, by *Treponema pallidum*), leptospirosis (caused, for example, by Leptospira interrogans), Lyme borreliosis (caused, for example, by *Borrelia burgdorferi*), tuberculosis (caused, for example, by *Mycobacterium tuberculosis*), leprosy (caused, for example, by *Mycobacterium leprae*), actinomycosis (caused, for example, by *Actinomyces* species), nocardiosis (caused, for example, by *Nocardia* species), *chlamydia* (caused, for example, by *Chlamydia psittaci, Chlamydia trachomatis,* or *Chlamydia pneumoniae*), Rickettsial diseases, including spotted fever (caused, for example, by *Rickettsia* rickesii) and Rickettsial pox (caused, for example, by *Rickettsia akari*), typhus (caused, for example, by *Rickettsia prowazekii*), brucellosis (caused, for example, by *Brucella abortus, Brucella melitens,* or *Brucella suis*), and tularemia (caused, for example, by *Francisella tularensis*). Diseases with similar origins and symptoms are also known to affect animals.

According to a specific embodiment, the controlling is prophylactic (reduces the incidence of infection).

According to a specific embodiment, the controlling is therapeutic (reduces the symptoms and/or duration of infection).

The bacterial strains/species can be administered to subjects in need thereof using methods which are well known in the art.

When used as a medicament, the bacterial strains/species of the present invention may be used in any suitable form—whether when alone or when present in a combination with other components or ingredients.

The microorganism of the present invention or composition of the present invention may be used in the form of solid or liquid preparations or alternatives thereof. Examples of solid preparations include, but are not limited to tablets, capsules, dusts, granules and powders which may be wettable, spray-dried or freeze-dried. Examples of liquid preparations include, but are not limited to, aqueous, organic or aqueous-organic solutions, suspensions and emulsions.

Suitable examples of forms include one or more of: tablets, pills, capsules, ovules, solutions or suspensions, which may contain flavouring or colouring agents, for immediate-, delayed-, modified-, sustained-, pulsed- or controlled-release applications.

By way of example, if the composition of the present invention is used in a tablet form—such for use as a functional ingredient—the tablets may also contain one or more of: excipients such as microcrystalline cellulose, lactose, sodium citrate, calcium carbonate, dibasic calcium phosphate and glycine; disintegrants such as starch (preferably corn, potato or tapioca starch), sodium starch glycollate, croscarmellose sodium and certain complex silicates; granulation binders such as polyvinylpyrrolidone, hydroxypropylmethylcellulose (HPMC), hydroxypropylcellulose (HPC), sucrose, gelatin and acacia; lubricating agents such as magnesium stearate, stearic acid, glyceryl behenate and talc may be included.

Examples of nutritionally acceptable carriers for use in preparing the forms include, for example, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, petroethral fatty acid esters, hydroxymethyl-cellulose, polyvinylpyrrolidone, and the like.

Exemplary excipients for the forms include lactose, starch, a cellulose, milk sugar or high molecular weight polyethylene glycols.

For aqueous suspensions and/or elixirs, the composition of the present invention may be combined with various sweetening or flavouring agents, colouring matter or dyes, with emulsifying and/or suspending agents and with diluents such as water, propylene glycol and glycerin, and combinations thereof.

The forms may also include gelatin capsules; fibre capsules, fibre tablets etc.; or even beverages.

Further examples of forms are in the form of a cream for example. For some aspects the microorganism may be included in pharmaceutical and/or cosmetic creams such as sun creams and/or after-sun creams for example.

In one aspect, the composition according to the present invention may be administered in an aerosol, for example by way of a nasal spray, for instance for administration to the respiratory tract.

According to a specific embodiment, the microbial species/strains as described herein are dispensed from an aerosol dispensing device (or system).

There are devices known to atomize a liquid and deliver the atomized liquid into the surrounding air.

According to a specific embodiment the aerosol dispensing device is automated.

Such an aerosol dispersing device can work on its own as well as in conjunction with an HVAC system.

Reference is now made to FIG. 13 showing a simplified schematic drawing of an example aerosol dispensing device with a replaceable cartridge that is actuated with compressed air in accordance with some example embodiments. An aerosol dispensing device 200 includes a housing 201 that may house an air compressor 104 to actuate atomizing a liquid 159 contained in a cartridge 150. Pressurized air provided by compressor 104 may be delivered through valve 102 and a channel 112, e.g. a tube to a connector 118. Connector 118 may establish a fluid connection between compressor 104, cartridge 150 and an aerosol outlet 129 from which atomized liquid 125 may be expelled. An atomizer 120 may be integrated in connector 118 or in collar 152 of cartridge 150. Optionally, an adaptor 119 provides a sealed connection between cartridge 150 and connector 118. Although connector 118 and adaptor 119 are shown as two separate elements, it is understood that functionality of these two elements may be integrated into a single part.

According to some example embodiments, at least one of a cartridge for an aerosol dispensing device and the aerosol dispensing device includes a mechanism for stirring liquid contents of the cartridge. Optionally, liquid content in the cartridge may be stirred continuously or periodically during use to maintain a substantially constant concentration of active material over a height of the liquid.

In some example embodiments, device 200 is self-powered with a power source 108. Alternatively, device 200 may be powered by an external power source. In some example embodiments, device 200 includes a user interface including for example a display 103 and one or more user actuated buttons or knobs 107.

Device 200 may be positioned in an indoor environment. The indoor environment may be a public space such as a hospital or a shopping center or may be a personal space such as an office, a home or a vehicle. Optionally, device 200 may be configured to direct aerosol 125 expelled from channel 129 into airflow ducts of a heating, ventilation and air conditioning (HVAC) system. Optionally, circuit 105 is in communication or receives input from an HVAC system and is operated in coordination with the HVAC system. Alternatively, device 200 may be operated independently from an HVAC system and the aerosol may also be dispersed directly into the indoor space, e.g. not through the HVAC ducts.

One such configuration is described in U.S. Pat. No. 8,986,610 entitled "Apparatus and method for dispersing liquid in aerosol," the contents of which is incorporated by reference herein, describes a system and method to deliver an atomized solution to the interior volume of a building or room utilizing a Venturi effect for the atomization. It is described that the solution may contain at least one active material including at least one of a medicament, probiotic, nutraceutical, or combinations thereof. The system includes a solution chamber; a Venturi configuration operatively associated with said solution chamber; an air inlet associated with a pressurized air inlet source; an actuator and a sensor. The solution chamber may be in the form of a replaceable cartridge.

In known automated aerosol dispensing devices, the live organism or active material is typically in the form of a water based solution stored in a replaceable cartridge. A device with embodiments having cartridge replacement embodiments is further described hereinbelow.

Reference is now made to FIGS. 14A and 14B showing a simplified schematic drawing of an example aerosol dispensing device and an example replaceable cartridge respectively and to FIG. 15 showing an example replaceable cartridge installed in an example aerosol dispensing device all in accordance with some example embodiments. An aerosol dispensing device 100 includes a housing 101 that may house an actuator 109 configured to actuate atomization of a liquid 159 in a cartridge 150, an outlet channel 129 from which atomized liquid 125 may be expelled and a circuit 105 configured to control operation of actuator 109. An atomizer 120 for creating aerosol 125 based on actuation with actuator 109, may be integrated as part of actuator 109 or may be integrated in cartridge 150. Optionally, actuator 109 is configured to establish fluid connection with cartridge 150. According to some example embodiments, aerosol dispensing device 100 additionally includes a reader 106 configured to read data on a tag 160 included on cartridge 150.

In some example embodiments, device 100 is self-powered with a power source 108. Alternatively, device 100 may be powered by an external power source. In some example embodiments, device 100 includes a user interface including for example a display 103 and one or more user actuated buttons or knobs 107. Optionally, device 100 additionally includes a sensor 117 configured to sense when cartridge 150 is installed in device 100. Sensor 117 may for example be an opto-coupler sensor that detects a break in a line of sight due to insertion of neck 152 into actuator 109. In another example, sensor 117 may be a button switch that is compressed based on insertion of collar 152 into actuator 109.

Device 100 may be positioned in an indoor environment. The indoor environment may be a public space such as a hospital or a shopping center or may be a personal space such as an office, a home or a vehicle. Optionally, device 100 may be configured to direct aerosol 125 expelled from channel 129 into airflow ducts of a heating, ventilation and air conditioning (HVAC) system. Optionally, circuit 105 is in communication or receives input from an HVAC system and is operated in coordination with the HVAC system. Alternatively, device 100 may be operated independently from an HVAC system and the aerosol may also be dispersed directly into the indoor space, e.g. not through the HVAC ducts.

According to some example embodiments, liquid 159 may include sensitive material such as a pro-biotic, medicament, nutraceutical, or combinations thereof that may be prone to contamination. The material when contaminated may pose a health hazard. Furthermore, any malicious tampering with cartridge 150 may also lead to a hazardous situation. For example an offender may maliciously insert a harmful bacteria or an irritant into cartridge 150. Alternately, an offender may attempt to refill cartridge 150 with unknown or unregulated contents that may not be suitable or safe in general or for a particular indoor space. In other examples, a hazardous situation may be created without malicious intent, for example when a solution in the cartridge has passed its expiration date or when a property of the solution has been altered due to prolonged exposure to humidity or air.

According to some example embodiments, circuit 105 includes safety verification functionality to verify compatibility, authenticity and safety of cartridge 150 when it is inserted into housing 101 and optionally to provide ongoing monitoring while cartridge 150 is maintained in device 100. The verification may be based on input received from reader 106. In some example embodiments, circuit 105 receives data from reader 106 and compares the data received to information stored in memory. Optionally, if an identification code read by reader 106 matches an identification code listed in the memory, verification may be established. The memory may be memory included in circuit 105, memory included in a remote server 800 or memory included in a cloud. Optionally, the information needed to verify authentication of cartridges may be uploaded by a remote server 800 and circuit 105 may access the information based on wireless communication. According to some example embodiments, circuit 105 is configured to terminate dispersion or formation of atomized liquid 125 and provide an alert when cartridge 150 cannot be positively verified.

Reader 106 may be configured to scan a code or interrogate a tag 160 positioned on cartridge 150, when cartridge 150 is installed in device 100 and provide the data to circuit 105. In some examples, reader 106 is or includes a camera or a RFID scanner that is configured to detect data stored on cartridge 150. Preferably, reader 106 is an active reader that is controlled and powered with circuit 105. In some example embodiments, controller 105 activates reader 106 at a defined frequency, e.g. every 5-60 minutes to scan or interrogate tag 160. Additionally or alternatively, controller 105 may activate reader at defined events. For example controller 105 may activate reader when power of device 100 is turned on and during installation of cartridge 150 in the device 100. In some example embodiments communication between reader 106 and tag 160 is wireless or contactless. In other example embodiments, communication between reader 106 and tag 160 is based on electrical contact.

Optionally, cartridge 150 configured for use with device 100 includes tag or code 160 with data to verify its compatibility. Tag or code 160 may be a barcode, e.g. a one dimensional or two dimensional barcode, maybe in passive RFID tag and may be an active RFID tag. Tag or code 160 may be positioned in an inner surface of cartridge 150 that is in contact with fluid 159 or may be positioned on an outer surface of cartridge 150. According to some example embodiments, tag or code 160 may be positioned on cartridge 150 so that it aligns with reader 106 while establishing a sealed connection with actuator 109.

In some example embodiments, tag or code 160 includes passive storage. Information tagged or coded on tag or code 160 may include one or more of the following items: state of a seal on the cartridge, identification data, part number of the product, batch number, production date, expiration date, quantity of material in the cartridge, contents of the cartridge and operating instructions.

Optionally, contents 159 of cartridge 150 are sealed with a seal under cap 151 that is configured to be broken in actuator 109 while inserting cartridge 150 into housing 101. Optionally, breaking of the seal alters data stored in tag or code 160 so that the event may be recorded and detected by reader 106. Optionally, this information may be used to prevent operating device 100 with cartridges that have been refilled. Cartridge 150 may be in the form of a bottle or may be any container that can contain fluid 159 to be dispersed as an aerosol. Typically cartridge 150 is configured to be replaced after its contents have been emptied.

In some example embodiments, tag 160 may be an active tag and reader 106 may transmit data to tag 160 that may be stored in tag 160. Active storage may be a microchip with RAM memory in which case a small power source may be included on cartridge 150. Alternatively, active storage may be an active RFID.

FIG. 16 shows a simplified schematic drawing of an example aerosol dispensing device including one or more sensors in accordance with some example embodiments. According to some example embodiments, the aerosol dispensing device 500 includes a regulator configured to regulate activity of device 500 installed with a cartridge 150. Functionality of the regulator may be included in circuit 105. Optionally, device 500 includes reader 106 and circuit 105 may regulate activity of device 500 based on information received from reader 106, e.g. instruction that may be specific to liquid 159 contained in the cartridge. Circuit 105 may additionally or alternatively regulate activity of device 500 based on inputs from one or more sensors in communication with circuit 105. In some example embodiment, device 500 includes sensors 128 configured to detect a parameter related to content 159 in cartridge 150. Optionally, sensor 128 is a level sensor for detecting a level of liquid 159 in cartridge 150. Optionally, one sensor 128 may be positioned to sense liquid at 1-3 cm from a bottom of cartridge 150 to detect when contents of cartridge 150 are nearly emptied. In some example embodiments, when contents of cartridge 150 are nearly emptied, circuit 105 may provide an alert on display 103 and may also communicate this information to a remote server 800 in communication with circuit 105. Remote server 800 may then alert a service provider or deliver a new cartridge to the site including device 500.

Device 500 may additionally include sensors 127 that may detect environmental conditions. Optionally, humidity is detected. In some example embodiments, temperature is detected. At times, an expiration date may be adjusted based on the detected environmental conditions. For example an expiration date may be shortened in environments with higher humidity as compared to environments that are more arid. Optionally, frequency or duration of actuation may be adjusted based on output detected from one or more of sensors 127, sensors 128 and based on data read with reader 106.

In some example embodiments, device 500 may be configured to receive input from a stand-alone sensor 126 that is remote from device 500. Input may be received based on tethered or wireless connection. Stand-alone sensor 126 may be for example an air quality probe similar to E4000 indoor air quality probe offered by NanoSense, France, a thermostat associated with an HVAC, or a humidity sensor. Input from remote sensors 126 may similarly be used to adjust an expiration date or to adjust frequency or duration of actuation based on the detected environmental conditions.

According to some example embodiments, the aerosol dispensing device 500 additionally includes safety verification functionality as described herein above to verify compatibility, authenticity and safety of cartridge 150 when it is inserted into device 500 and optionally to provide ongoing monitoring while cartridge 150 is maintained in device 500. In some example embodiments, the safety verification functionality is based on reader 106 reading data on a tag 160 included on cartridge 150 and circuit 105 processing the data.

According to some embodiments the bacterial species/strains as described herein or compositions comprising same are not to be used in the treatment of agricultural water (irrigation water), agricultural soils and agricultural crops.

According to some embodiments, the bacterial species/strains as described herein or compositions comprising same can be used in the treatment of agricultural water (irrigation water), agricultural soils and agricultural crops. In still other embodiments, the formulations of cultured bacteria can be applied in the treatment at food processing facilities. In the case of food processing facilities, agricultural waters and soils, the formulations of cultured bacteria can be applied prophylactically or as a sanitizing agent following an exposure. The product can be used to treat foods including meat and meat products. The meat product can generally be any whole, cut, ground or processed meat product, including, ground beef ("hamburger"), ground turkey, ground chicken, ground pork, beef sausage, pork sausage, chicken sausage, turkey sausage, hot dogs, bologna, salami, cold cuts, game hens, whole chicken, lamb, ham, pork, cube meat, steaks, roasts, fillets, fish, or liver.

Any type of agricultural produce sold in marketplaces, such as those derived from plant or fungi, can be treated by the methods and compositions disclosed herein. Additional types of produce products that can be treated by the disclosed antimicrobial compositions include but are not limited to those derived from leaves, stems, fruit, flowers, seeds, roots, and like components that form the plant, as well as those derived from fungi, including the cap, stem, mycelium and annulus, and like components that form the fungi.

Any type of surface can be treated with the bacterial strains/species as described herein. Examples of surfaces that may be treated include of animate surfaces such, as those of animals or plants, and inanimate surface, such as food, buildings, furniture, objects and the like. Specific examples of surfaces that the composition could be applied to include, but are not limited to the following: meat, grinders, processors, extruders, cutting surfaces, cutting apparatus, blades, seafood, agricultural produce (fruit, vegetables, etc.), nuts, legumes, sprouts, trees, leaves, seeds, bulbs, flowers, animals (livestock and pets), eggs shells, skin, hair, bone, horn, hooves, wool, leather, lawns, fields, soil, floors, walls, countertops, cabinets, toilets, bathtubs, bathrooms (portable and non-portable), sinks, laundry equipment, kitchen appliances (refrigerators, freezers, dishwashers, etc.), heating and refrigeration coils, fans, ceiling fans, heating systems, air conditioning system, ventilation systems, internal and external ducts for ventilation, heating and air conditioning, tabletops, chairs and sofas, desks, luggage, fabrics, clothing, footwear, sports equipment, audio/visual equipment, computers, clocks, boxes (cardboard, wood, etc.), books, paper surfaces, garbage/trash receptacles, building materials, interior and exterior of transportation equipment (automobiles, airplanes, trains, boats, etc.), interior and exterior of spacecraft and other space facilities, trailers, tires, metal, ceramic, tile, linoleum, carpet, wall paper, painted surfaces, plastic, vinyl, polyvinyl chloride (PVC) and the like, plastic, rubber, glass, hose line, plumbing (inside and outside), other application machinery, lighting, heating and cooling filaments, ovens, storage containers, bottles, cans, reception areas, milking parlors, food processing facilities, and the like.

The article of manufacture may be packaged in a form that is appropriate or convenient for shipment, administration, or storage. For example, the product can be placed into a hermetically sealed pouch of plastic, paper, metalized plastic, or metal (e.g. aluminum), bottle, cartridge capsule, plastic bag, or a box. In the article of manufacture each strain can be packaged in a separate package or some strains can be combined (e.g., *B. subtilis* 3 and *B. subtilis* 281 strains) or all combined together (composition which comprises all the bacteria).

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is understood that any Sequence Identification Number (SEQ ID NO) disclosed in the instant application can refer to either a DNA sequence or a RNA sequence, depending on the context where that SEQ ID NO is mentioned, even if that SEQ ID NO is expressed only in a DNA sequence format or a RNA sequence format.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Materials and Methods

Strains

Bacillus strain was isolated from home-made Doenjang using Luria Bertani Miller agar (BD, Difco) agar for plating. Representative colonies were picked from plates with the highest dilution still showing colonies. After purification, the strain was stored at −80° C. The stock culture was propagated first in 10 ml LB Miller broth (in 50 ml Falcon sterile tube) for 18 hours (rotary shaker, 120 RPM), and then the culture was 1% diluted into a fresh media and was propagated in the same conditions as described previously, before each experiment.

Reference strains were obtained from ATCC (American Type Culture Collection) and KACC (Korean Agricultural Culture Collection) and KCTC (Korea, Collection for Type Cultures).

16S rDNA Sequencing

Pure cultures of *Bacillus amyloliquefaciens* 298 was grown on LB Miller agar (BD Difco) at 37° C. for 24 hours. The plate was sent to Solgent Inc. (Deajun, South Korea) for bi-directional 16S rDNA sequencing using (5'-AGA GTT TGATCMTGG CTC AG-3', SEQ ID NO: 1) and 1492R (5'-TAC GGY TAC CTT GTT ACG ACTT-3' SEQ ID NO: 2) primers by (Reysenbach, Giver et al. 1992). Bi-directional sequencing results were assembled using Codon Code Aligner (Codon Code Corporation, USA) and compared with reference sequences of *Bacillus* species on the GenBank database (www(dot)ncbidotnlm(dot)nih(dot)gov/Blastn/).

API Test

Specific sugar fermentation pattern was monitored using API 50CHB strips (Biomerieux). The *Bacillus* strain pellet was prepared using LB Miller agar (BD Difco) at 37° C. for 24 hours and centrifuged 14,000 rpm for 5 min. The pellet was suspended using the preparation media in the kit and applied on different sugars according to the instruction manual.

Hemolysis Test

*B. amyloliquefaciens* 298 was grown at 37° C. for 18 hours in LB broth and then streaked onto 5% sheep blood agar (Hanil Komed) and incubated for 24 h at 37° C. Alpha (α) hemolysis was considered as the partial decomposition of the hemoglobin of the red blood cells, beta (β) hemolysis as the complete breakdown of the hemoglobin of the red blood cells observed as a clear zone in the agar plate and gamma (γ) hemolysis as the lack of hemolysis. *B. cereus* ATCC 27348 was used as a positive control.

Lecithinase Test

*B. amyloliquefaciens* 298 and *B. cereus* ATCC 27348 (positive control) were grown at 37° C. for 18 hours in LB Miller broth and streaked out onto egg yolk agar. The plates were incubated for 24 h at 37° C. and the formation of a white precipitate around the colonies was considered as positive for lecithinase activity (Hong, Huang et al. 2008, Sorokulova, Pinchuk et al. 2008).

Antibiotic Resistance Test

The basic protocol was followed by CLSI recommendation (Jorgensen and Turnidge 2015). Pure cultures of *B.*

*amyloliquefaciens* 298 were cultivated at 37° C. for 18 hours in LB Miller agar. The agar dilution method was used to assess the minimal inhibitory concentration (MIC) of the antibiotics against the strain. A single colony was resuspended in phosphate buffer saline (PBS) 1× and adjusted 0.01 optical density (OD). Ten microliters (1×10$^5$ CFU/mL) of strain were inoculated on the plates using multipin-inoculator and incubated at 37 C for 24 hours. The strain was considered susceptible when they were inhibited at a concentration for a specific antimicrobial equal or lower than the established cut-off value and resistant bacterial strain when it was not inhibited at a concentration of a specific antimicrobial higher than the established cut-off value according to the parameters established by the European Food Safety Authority (EFSA).

Inhalation Infection Test

The animal study was approved by Handong Global University Ethical committee. For the experiment, 40 mice were divided into four groups comprising negative control, two positive controls. infected with pathogenic microorganisms of *Streptococcus pneumoniae* ATCC49619 and *Bacillus cereus* ATCC27348 and one group infected with the tested microorganism. Potential probiotic *B. amyloliquefaciens* 298 was infected at a dose of 1×10$^7$ CFU/mouse with pre-treatment of cyclophosphamide to induce immunocompromised status. The cyclophosphamide was used to derive immunocompromised animal model to monitor more emphasized influence of infected microorganism so called worst case scenario (Kong, Hellermann et al. 2005).

The *B. amyloliquefaciens* 298 was grown for 18 hours in LB Miller broth (BD Difco) at 37° C. while *S. pneumoniae* ATCC49619 was cultured on 5% Sheep blood agar and sub-cultured to Brain Heart Infusion broth (BD Difco) and incubated at 37° C. The bacterial solution was diluted using 1×PBS to 1×10$^7$ CFU/mouse. The inoculum concentration was determined by enumeration of cultured bacteria on agar plates.

The animal lung infection model was carried out in 4-week-old female ICR mice (Hyo-chang science). The mice were anesthetized during respiratory infection (*Streptococcus pneumoniae* ATCC49619 and *Bacillus cereus* ATCC27348) using 50 μL of bacterial suspension through intranasal route. After 24 h post infection, 2 mice of each group were selected randomly and sacrificed with diethyl ether for enumeration of viable colonies in lungs. Lungs were extracted and homogenized with Phosphate-buffered saline (PBS). Before homogenization, lungs were monitored visually. The homogenized lung samples were diluted and spread on 5% Sheep blood agar to enumerate number of pathogens in the lungs. The plates were incubated for 18 hours. The rest of the mice were monitored during 1 week to measure their survival rates (Ginsberg, Moldawer et al. 1991).

Efficacy Tests

The agar well diffusion assay was performed to evaluate the antagonistic activity of *B. amyloliquefaciens* 298 against the growth of pathogenic bacteria including *Escherichia coli* ATCC 22922, *Pseudomonas aeruginosa*, *B. cereus* ATCC 27348, *Staphylococcus aureus* ATCC 11335, *Salmonella Typhimurium* ATCC 14028 and *Listeria innocua* ATCC 3586. The antagonistic activity of *B. amyloliquefaciens* 298 was also verified against molds such as *Alternaria alternata* (Fries) Keissler (ATCC® MYA-4642™), *Cladosporium sphaerospermum* Penzig (ATCC® MYA-4645™) and *Penicillium chrysogenum* Thom (ATCC® MYA-4644™). Brain Heart Infusion (BHI) Agar was used for the antagonism against pathogenic microorganisms while the Potato Dextrose Agar (PDA) was used for evaluation against molds. Reference pathogens were prepared using BHI broth at 37° C. for 18 hours while *B. amyloliquefaciens* 298 was grown using LB broth at 37° C. for 18 hours. Molds were prepared using PDA at 25° C. with 85% HR for 7 days. Mold spores, pathogens and *B. amyloliquefaciens* 298 were harvested and resuspended in PBS. Pathogens and *B. amyloliquefaciens* 298 were adjusted to an optical density of 0.2 and 100 uL of pathogen suspended in PBS was spread on BHI agar plates. The same amount of mold spore suspension was inoculated on PDA. Wells were made in all the plates and 20 μL of *B. amyloliquefaciens* 298 suspensions were inoculated in the wells while the BHI plates were incubated at 37° C. for 24 hours and PDA plates at 25° C. for 72 hours. The inhibition of pathogens and molds was observed as a clear zone around the *bacillus* strain inoculated wells and 10% hydrogen peroxide served as a positive control.

16S rDNA Sequence

The identity of the strain was confirmed as *B. subtilis* according to the National Center for Biotechnology Information (NCBI) database according to the 16S-rRNA (SEQ ID NO: 3) sequencing result.

Complete Genome Sequence

The complete genome sequence of *B. amyloliquefaciens* 298 was generated using the PacBio RS platform with single-molecule real-time (SMRT) sequencing at Theragenetex (Seoul, South Korea). Annotations were performed by merging the results obtained from the Rapid Annotations using Subsystems Technology (RAST) server, Glimmer 3.02 modeling software, tRNAscan-SE 2.0, and RNAmmer 1.2. In addition, the contigs were searched against the KEGG, UniProt, and Clusters of Orthologous Groups (COG) databases to annotate the gene description. The results are shown in SEQ ID NO: 4.

Metabolite Analysis

Total protein was extracted from growth media of *B. amyloliquefaciens* 298 after 18 hours at 37° C. incubation to evaluate the secreted metabolites of *B. amyloliquefaciens* 298. A stock solution was prepared dissolving 500 g of Trichloroacetic acid (TCA) into 350 ml of distilled water. 1 volume of TCA stock solution was added to 4 volumes of *B. amyloliquefaciens* 298 growth media and incubated at 4° C. for 10 min. The tube was centrifuged at 14,000 rpm for 5 min and supernatant was removed to concentrate the protein pellet. The pellet was washed with 200 μl cold acetone and again concentrated by 14,000 rpm centrifugation for 5 min. This step was repeated for three times and the pellet was sent to be analyzed using LC-LTQ-Orbitrap at Technopark Biocenter (Pohang, South Korea). The raw data was analyzed using UniProt database to match predicted proteins from the growth media of *B. amyloliquefaciens* 298.

Example 1A

In-Vitro Safety Evaluation of Lecithinase and Hemolysis Activity

*B. amyloliquefaciens* 298 did not show lecithinase activity observed as the absence of a white precipitate around the *Bacillus* colonies and all *B. amyloliquefaciens* 298 showed negative reaction for hemolysis as well.

TABLE 1

Lecithinase and hemolysis activity of *B. amyloliquefaciens* 298 and *B. cereus* ATCC 27348.

| Strain | Lecithinase activity | Hemolysis activity |
|---|---|---|
| *Bacillus amyloliquefaciens* 298 | Negative | Gamma |
| *Bacillus cereus* ATCC 27348 (positive control) | Positive | Beta |

Example 1B

In-Vitro Evaluation of Antibiotic Resistance

The agar dilution was used to evaluate the minimal inhibitory concentration (MIC) of antibiotics. *B. amyloliquefaciens* 298 was found to be sensitive to erythromycin, gentamicin, tetracycline, streptomycin, vancomycin, chloramphenicol, kanamycin and clindamycin according to the European Food Safety Authority MIC breakpoints for *Bacillus* species. The determined MIC values are clearly below or equal to the EFSA breakpoint values (Table 2).

TABLE 2

Minimum inhibitory concentrations (MIC) of *B. amyloliquefaciens* 298. Antibiotic resistance test

| Strain | Minimum inhibitory concentration (mg/L) of antibiotics | | | | | | | |
|---|---|---|---|---|---|---|---|---|
| | Ery | Gen | Tet | Str | Van | Chl | Kan | Cli |
| *B. amyloliquefaciens* 298 | ≤0.125 | ≤2 | ≤0.125 | 8 | 0.25 | ≤4 | ≤4 | 0.5 |
| EFSA breakpoint | 4 | 4 | 8 | 8 | 4 | 8 | 8 | 4 |

Ery: Erythromycin;
Gen: Gentamicin;
Tet: Tetracycline;
Str: Streptomycin;
Vm: Vancomycin;
Chl: Chloramphenicol;
Kan: Kanamycin;
Cli: Clindamycin.

Example 1C

Respiratory Tract Infection Test

Figure 2:
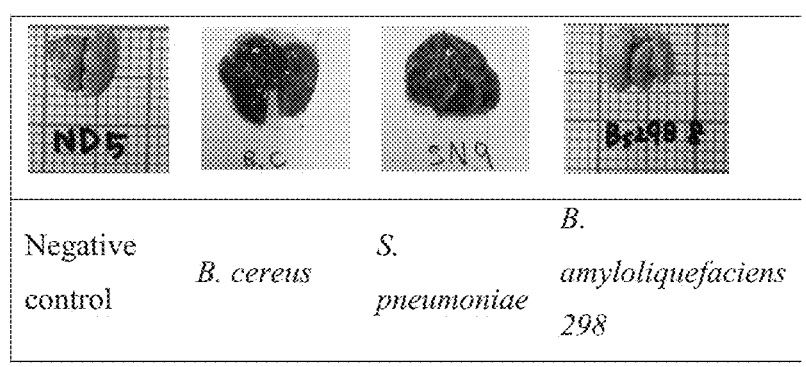
FIG. 2 is a photograph showing the appearance of lungs in each group described in FIG. 1.

The survival rate after respiratory tract infection of *B. amyloliquefaciens* 298 was 100% while the positive control of pathogenic bacteria infected groups including *S. pneumoniae* and *B. cereus* showed 100% mortality after 24 hours (FIG. 1). Lung pictures were taken and showed strong damage in pathogen infected positive groups while lung of *B. amyloliquefaciens* 298 infected groups showed similar lung status as negative control group (FIG. 2) and any colony of *Bacillus* was found from the homogenized lung of *B. amyloliquefaciens* 298 infected group (data not shown). These data demonstrate that *B. amyloliquefaciens* 298 does not infect lung probably due to lack of colonization in the lung.

Example 1D

Efficacy Tests

Figure 3:
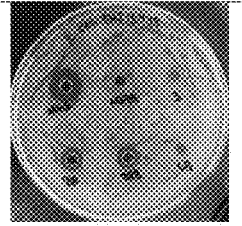
FIG. 3 is a photograph showing antagonism of pathogenic bacteria by *B. amyloliquefaciens* 298.
Figure 3:
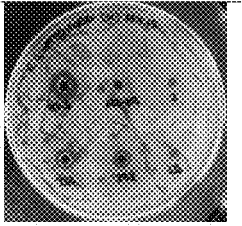
Figure 3:
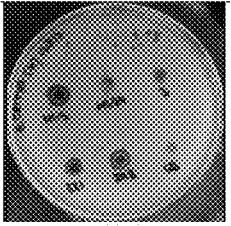
Figure 3:
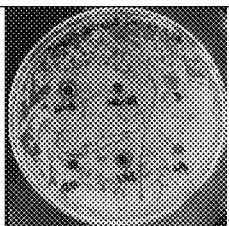
Figure 3:
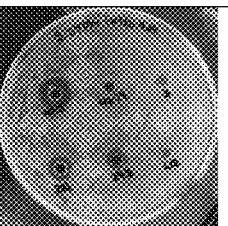
Figure 3:
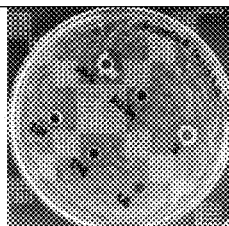

The antagonism test results of *B. amyloliquefaciens* 298 showed inhibited growth of *E. coli* ATCC 22922, *P. aeruginosa*, *B. cereus* ATCC 27348 and *S. Typhimurium* ATCC 14028 at different degrees (FIG. 3 and Table 3).

TABLE 3

Antagonistic activity of *Bacillus amyloliquefaciens* 298 against pathogens.

| Pathogens | *B. amyloliquefaciens* 298 |
|---|---|
| *Escherichia coli* ATCC 22922 | 2 |
| *Pseudomonas aeruginosa* | 1 |
| *Bacillus cereus* ATCC 27348 | 2 |
| *Staphylococcus aureus* ATCC 11335 | 1 |
| *Salmonella Typhimurium* ATCC 14028 | 2 |
| *Listeria innocua* ATCC 3586 | NA |

NA: No antagonism was observed

Figure 4:
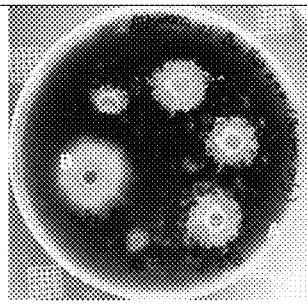
FIG. 4 is a photographic representation of results for the antagonism of test molds using *B. amyloliquefaciens* 298 (A) and 10% hydrogen peroxide (B) as a positive control.
Figure 4:
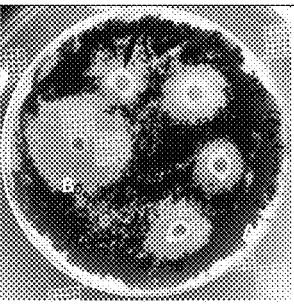
Figure 4:
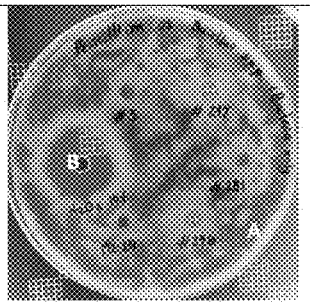

*B. amyloliquefaciens* 298 antagonism against mold indicates positive antagonism against *Alternaria alternata* (Fries) Keissler (ATCC® MYA-4642™) and *Cladosporium sphaerospermum* Penzig (ATCC® MYA-4645™) at variable level (Table 4). The inhibition of the mold growth is evidently expressed as a clear zone around the wells inoculated with the *B. amyloliquefaciens* 298 (FIG. 4). *Penicillium chrysogenum* Thom (ATCC® MYA-4644™) was not inhibited at all for any of the strains used on this experiment, however the mycelium color around the well inoculated with *B. amyloliquefaciens* 298 show and slightly decrease in the intensity (data not shown) from green to white.

TABLE 4

Antifungal activity of *Bacillus amyloliquefaciens* 298 against molds.

| | Inhibition zone (mm) | | |
|---|---|---|---|
| Strain | *Alternaria alternata* (Fries) Keissler (ATCC MYA-4642) | *Cladosporium sphaerospermum* Penzig (ATCC MYA-4645) | *Penicillium chrysogenum* Thom (ATCC MYA-4644) |
| *Bacillus amyloliquefaciens* 298 | 6 | 6 | NA |
| Hydrogen peroxide 10% | 8 | 12 | 10 |

NA: No antagonism was observed

Example 1E

Taxonomic Identification

The identity of the strain was confirmed as *B. subtilis* according to the National Center for Biotechnology Information (NCBI) database. API results were monitored for further identification of physiological characteristics.

Example 1F

Complete Genome Sequence

A Single run of PacBio provided total number of 151,771 reads which comprises in total of 1,368,609,189 bases. Raw data was assembled using Canu v1.6 and single contig was produced in size of 3,928,316 base pairs (Separate attached text file of "*Bacillus amyloliquefaciens* 298.fasta"). Total number of genes were 3,854 (3,740 coding sequences) and 3,044 annotated genes were found which calculated as 81.39% of total genes (gene annotations are listed in Table 5 below).

Lengthy table referenced here

US11602550-20230314-T00001

Please refer to the end of the specification for access instructions.

Example 2

Materials and Methods

Strains

*Bacillus* strains were isolated from home-made Doenjang using Luria Bertani Miller agar (BD, Difco) agar for plating. Representative colonies were picked from plates with the highest dilution still showing colonies. After purification, the strains were stored at −80° C. Before each experiment, the stock culture was cultured in 10 ml LB Miller broth (BD, Difco) in 50 ml falcon sterile tubes for 18 hours at 37° C. in a shaking incubator (rotatory, 120 RPM), the tubes were located in a slope position at an angle of ca80° relative to the vertical line. Then 1% diluted to fresh media (and grown in the same conditions). The culture was then streaked on LB Miller agar (BD, Difco) and incubated for 18 hours. Representative colony was picked and cultured on LB Miller broth (BD, Difco) at 37° C. in a shaking incubator (rotatory, 120 RPM according to the time indicated at each test. Reference strains were obtained from ATCC (American Type Culture Collection) and KACC (Korean Agricultural Culture Collection) and KCTC (Korea, Collection for Type Cultures).

16S rDNA Sequencing

Pure cultures of *Bacillus subtilis* 3 were grown on LB Miller agar (BD Difco) at 37° C. for 24 hours. The plate was sent to Solgent Inc. (Deajun, South Korea) for bi-directional 16S rDNA sequencing using (5'-AGA GTT TGATCMTGG CTC AG-3', SEQ ID NO: 1) and 1492R (5'-TAC GGY TAC CTT GTT ACG ACTT-3', SEQ ID NO: 2) primers by (Reysenbach, Giver et al. 1992). Bi-directional sequencing results were assembled using Codon Code Aligner (Codon Code Corporation, USA) and compared with reference sequences of *Bacillus* species on the GenBank database (www(dot)ncbi(dot)nlm(dot)nih(dot)gov/Blastn/).

API Test

Specific sugar fermentation pattern was monitored using API 50CHB strips (Biomerieux). The *Bacillus* strain pellet was prepared using LB Miller agar (BD Difco) at 37° C. for 24 hours and centrifuged 14,000 rpm for 5 min. The pellet was suspended using the preparation media in the kit and applied on different sugars according to the instruction manual.

Hemolysis Test

*B. subtilis* 3 was grown at 37° C. for 18 hours in LB broth and then streaked onto 5% sheep blood agar (Hanil Komed) and incubated for 24 h at 37° C. Alpha (α) hemolysis was considered as the partial decomposition of the hemoglobin of the red blood cells, beta (β) hemolysis as the complete breakdown of the hemoglobin of the red blood cells observed as a clear zone in the agar plate and gamma (γ) hemolysis as the lack of hemolysis. *B. cereus* ATCC 27348 was used as a positive control.

Lecithinase Test

*B. subtilis* 3 and *B. cereus* ATCC 27348 (positive control) were grown at 37° C. for 18 hours in LB Miller broth and streaked out onto egg yolk agar. The plates were incubated for 24 h at 37° C. and the formation of a white precipitate around the colonies was considered as positive for lecithinase activity (Hong, Huang et al. 2008, Sorokulova, Pinchuk et al. 2008).

Antibiotic Resistance Test

The basic protocol was followed by CLSI recommendation (Jorgensen and Turnidge 2015). Pure cultures of *B. subtilis* 3 were cultivated at 37° C. for 18 hours in LB Miller agar. The agar dilution method was used to assess the minimal inhibitory concentration (MIC) of the strain against antibiotics. A single colony was resuspended in phosphate buffer saline (PBS) 1× and adjusted 0.01 optical density (OD). Ten microliters ($1 \times 10^5$ CFU/mL) of strain were inoculated on the plates using multipin-inoculator and incubated at 37° C. for 24 hours. The strain was considered susceptible when they were inhibited at a concentration for a specific antimicrobial equal or lower than the established cut-off value and resistant bacterial strain when it was not inhibited at a concentration of a specific antimicrobial higher than the established cut-off value according to the parameters established by the European Food Safety Authority (EFSA).

Inhalation Infection Test

The animal study was approved by Handong Global University Ethical committee. For the experiment, 40 mice were divided into four groups comprising negative control, two positive controls infected with pathogenic microorganisms of *Streptococcus pneumoniae* ATCC49619 and *Bacillus cereus* ATCC27348. Potential probiotic *B. subtilis* 3 was infected in dose of $1 \times 10^7$ CFU/mouse with pre-treatment of cyclophosphamide to induce immunocompromised status. The cyclophosphamide was used to derive immunocompromised animal model to monitor more emphasized influence of infected microorganims so called worst case scenario (Kong, Hellermann et al. 2005). The *Bacillus* strain was grown for 18 hours in LB Miller broth (BD Difco) at 37° C. while *S. pneumoniae* ATCC49619 was cultured on 5% Sheep blood agar and subcultured to Brain Heart Infusion broth (BD Difco) and incubated at 37° C. The bacterial solution was diluted using 1×PBS to $1 \times 10^7$ CFU/mouse. The inoculum concentration was determined by enumeration of cultured bacteria on agar plates.

The animal lung infection model was carried out in 4-week-old female ICR mice (Hyo-chang science). The mice were anesthetized during respiratory infection using 50 µL of bacterial suspension through intranasal route. After 24 h post infection, 2 mice of each group were selected randomly and sacrificed with diethyl ether for enumeration of viable colonies in lungs. Lungs were extracted and homogenized with Phophate-buffered saline (PBS). Before homogenization, lungs were monitored visually. The homogenized lung samples were diluted and spread on 5% Sheep blood agar to enumerate number of pathogens in the lungs. The plates were incubated for 18 hours. The rest of the mice were monitored during 1 week to measure their survival rates (Ginsberg, Moldawer et al. 1991).

Efficacy Tests

The agar well diffusion assay was performed to evaluate the antagonistic activity of B. subtilis 3 against the growth of pathogenic bacteria including Escherichia coli ATCC 25922, Pseudomonas aeruginosa ATCC 27853, B. cereus ATCC 27348, Staphylococcus aureus ATCC 6538, Salmonella Typhymurium ATCC 14028 and Listeria inocua ATCC 33090. The antagonistic activity of B. subtilis 3 was also verified against molds such as Alternaria alternata (Fries) Keissler (ATCC® MYA-4642™), Cladosporium sphaerospermum Penzig (ATCC® MYA-4645™) and Penicillium chrysogenum Thom (ATCC® MYA-4644™). Brain Heart Infusion (BHI) Agar was used for the antagonism against pathogenic microorganisms while the Potato Dextrose Agar (PDA) was used for evaluation against molds. Reference pathogens were prepared using BHI broth 37° C. for 18 hours, while B. subtilis 3 was grown using LB broth at 37° C. for 18 hours. Molds were prepared using PDA at 25° C. with 85% HR for 7 days. Mold spores, pathogens and B. subtilis 3 were harvested and resuspended in PBS. Pathogens and B. subtilis 3 was adjusted at optical density of 0.2 and 100 μL of pathogen suspended in PBS was spreaded on BHI agar plates. The same amount of mold spore suspension was inoculated on PDA. Wells were made in all the plates and 20 μL of B. subtilis 3 suspensions were inoculated in the holes while the BHI plates were incubated at 37° C. for 24 hours and PDA plates at 25° C. for 72 hours. The inhibition of pathogens and molds were observed as a clear zone around the bacillus strain inncoulated wells and 10% hydrogen peroxide was served as a positive control.

Complete Genome Sequence

The complete genome sequence of B. subtilis 3 was generated using the PacBio RS platform with single-molecule real-time (SMRT) sequencing at Theragenetex (Seoul, South Korea). Annotations were performed by merging the results obtained from the Rapid Annotations were performed by merging the results obtained from the Papid Annotaions using Subsystems Technology (RAST) server, Glimmer 3.02 modeling software, tRNAscan-SE 2.0, and RNAmmer 1.2. In addition, the contigs were searched against the KEGG, UniProt, and Clusters of Orthologous Groups (COG) databses to annotate the gene description.

Metabolite Analysis

Total protein was extracted from growth media of B. subtilis 3 after 18 hours at 37° C. incubation to evaluate metabolite of B. subtilis 3. Stock solution was prepared dissolving 500 g of Trichloroacetic acid (TCA) into 350 ml of distilled water. 1 volume of TCA stock solution was added to 4 volumes of B. subtilis 3 growth media and incubated at 4° C. for 10 min. Tube was centrifuged at 14,000 rpm for 5 min and supernatant was removed to concentrate protein pellet. The pellet was washed with 200 μL of cold acetone and again concentrated by 14,000 rpm centrifugation for 5 min. This step was repeated three times and the pellet was sent to be analyzed using LC-LTQ-Orbitrap at Technopark Biocenter (Pohang, South Korea). The raw data was analyzed using UniProt database to match predicted proteins from the growth media of B. subtilis 3.

Example 2A

In-Vitro Safety Evaluation of Lecithinase and Hemolysis Activity

B. subtilis 3 did not show lecithinase activity observed as the absence of a white precipitate around the Bacillus colonies and B. subtilis 3 showed negative reaction for hemolysis as well.

TABLE 6

Lecithinase and hemolysis activity of B. subtilis 3 and B. cereus ATCC 27348.

| Strain | Lecithinase activity | Hemolysis activity |
| --- | --- | --- |
| Bacillus subtilis 3 | Negative | Gamma |
| Bacillus cereus ATCC 27348 (positive control) | Positive | Beta |

Example 2B

In-Vitro Evaluation of Antibiotic Resistance

The agar dilution was used to evaluate the minimal inhibitory concentration (MIC) of antibiotics. B. subtilis 3 was found to be sensitive to erythromycin, gentamicin, tetracycline, streptomycin, vancomycin, chloramphenicol, kanamycin and clindamycin according to the European Food Safety Authority MIC breakpoints for Bacillus species. The determined MIC values are clearly below or equal to the EFSA breakpoint values (Table 2).

TABLE 7

Minimum inhibitory concentrations (MIC) of B. subtilis 3. Antibiotic resistance test

| Strain | Minimum inhibitory concentration (mg/L) of antibiotics | | | | | | | |
| --- | --- | --- | --- | --- | --- | --- | --- | --- |
| | Ery | Gen | Tet | Str | Van | Chl | Kan | Cli |
| B. subtilis 3 | ≤2 | ≤2 | ≤4 | 8 | ≤2 | ≤4 | ≤4 | 4 |
| EFSA breakpoint | 4 | 4 | 8 | 8 | 4 | 8 | 8 | 4 |

Ery: Erythromycin;
Gen: Gentamicin;
Tet: Tetracycline;
Str: Streptomycin;
Vm: Vancomycin;
Chl: Chloramphenicol;
Kan: Kanamycin;
Cli: Clindamycin.

Example 2C

Respiratory Tract Infection Test

Figure 5:
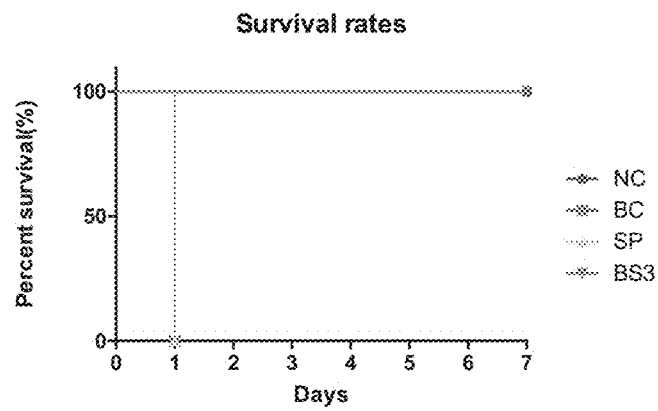
FIG. 5 is a graph showing Survival rates of mice after respiratory tract infection (NC: negative control, BC: *B. cereus*, SP: *S. pneumoniae*, BS3: *B. subtilis* 3).
Figure 6:
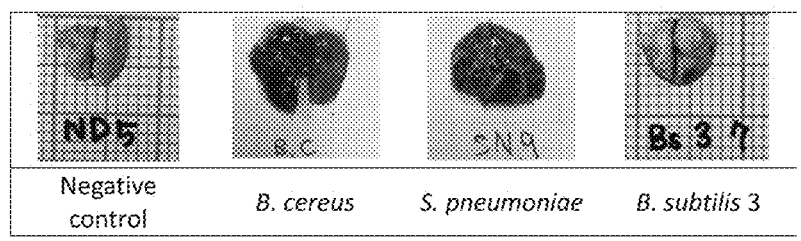
FIG. 6 is a photograph showing the appearance of lungs in each group described in FIG. 5.

The survival rate after respiratory tract infection of three candidates of B. subtilis 3 was 100% while the positive control of pathogenic bacteria infected groups including S. pneumoniae and B. cereus showed 100% mortality after 24 hours (FIG. 5). All lung pictures were taken and showed strong damage in pathogen infected positive groups, while lung of B. subtilis 3 infected groups showed similar lung status as negative control group (FIG. 6) and no colony of *Bacillus* was found from the homogenized lung of *B. subtilis* 3 infected group (data not shown).

Example 2D

Efficacy Tests

Figure 7:
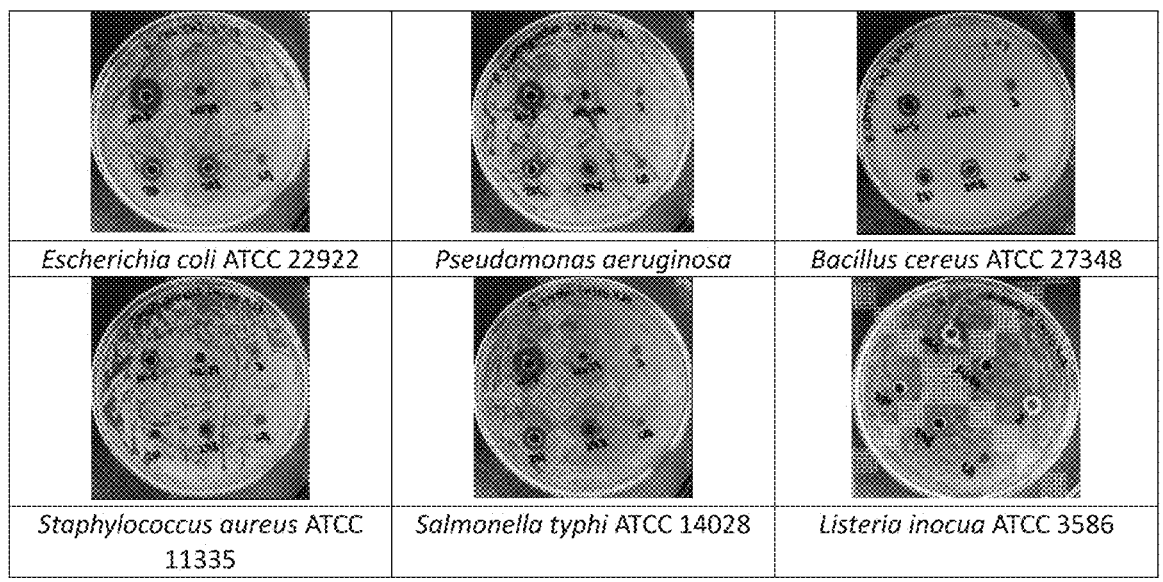
FIG. 7 is a photograph showing antagonism of pathogenic bacteria by *B. subtilis* 3.

The antagonism test results of *B. subtilis* 3 against pathogenic bacteria indicate that *B. subtilis* 3 reduce the growth of *E. coli* ATCC 22922, *S. aureus* ATCC 11335 and *L. inocua* ATCC 3586 at various levels (FIG. 7).

TABLE 8

| Antagonistic activity of *Bacillus subtilis* 3 against pathogens. | |
|---|---|
| Pathogens | *B. subtilis* 3 |
| *Escherichia coli* ATCC 25922 | 1 |
| *Pseudomonas aeruginosa* ATCC 27853 | NA |
| *Bacillus cereus* ATCC 27348 | NA |
| *Staphylococcus aureus* ATCC 6538 | 1 |
| *Salmonella Typhmurium* ATCC 14028 | NA |
| *Listeria inocua* ATCC 33090 | 2 |

NA: No antagonism was observed

Figure 8:
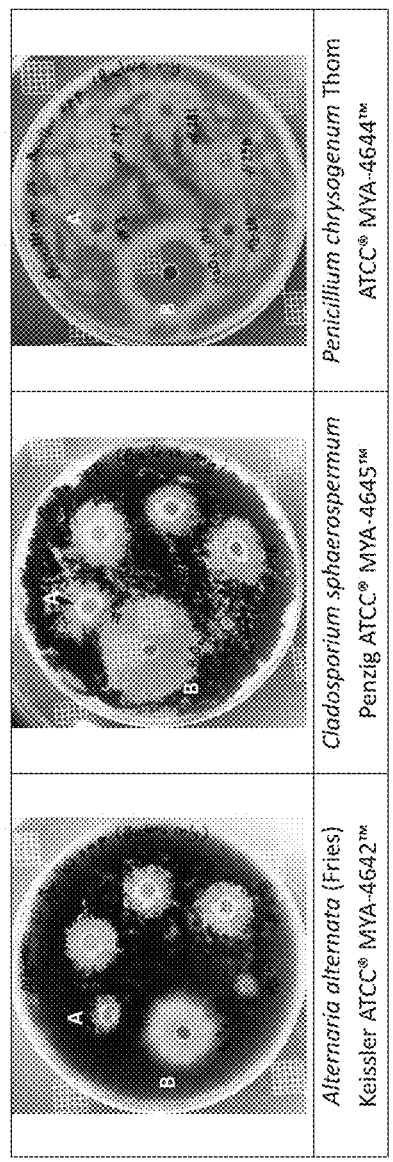
FIG. 8 is a photograph showing antagonism of molds using *B. subtilis* 3 (A) and 10% hydrogen peroxide (B) as a positive control.

*B. subtilis* 3 antagonism against mold indicate positive antagonism against *Alternaria alternata* (Fries) Keissler (ATCC® MYA-4642™) and *Cladosporium sphaerospermum* Penzig (ATCC® MYA-4645™) at variable level (Table 4). The inhibition of the mold growth is evidently expressed as a clear zone around the wells inoculated with the *B. subtilis* 3 (FIG. 8). *Penicillium chrysogenum* Thom (ATCC® MYA4644™) was not inhibited at all for any of the strains used on this experiment.

TABLE 9

| Antifungal activity of *Bacillus subtilis* 3 against molds. | | | |
|---|---|---|---|
| | Inhibition zone (mm) | | |
| Strain | *Alternaria alternata* (Fries) Keissler (ATCC MYA-4642) | *Cladosporium sphaerospermum* Penzig (ATCC MYA-4645) | *Penicillium chrysogenum* Thom (ATCC MYA-4644) |
| *Bacillus subtilis* 3 | 2 | 4 | NA |
| Hydrogen peroxide 10% | 8 | 12 | 10 |

NA: No antagonism was observed

Example 2E

Taxonomic Identification

The identity of the strain was confirmed as *B. subtilis* according to the National Center for Biotechnology Information (NCBI) database. API results were monitored for further identification of physiological characteristics.

Example 2F

16S rRNA

The identity of the strain having the 16S rRNA sequence as set forth in SEQ ID NO: 5 was confirmed as *B. subtilis*, according to the National Center for Biotechnology Information (NCBI) database.

Example 2G

Complete Genome Sequence

Single run of PacBio provided total number of 187,256 reads which comprises in total of 1,717,197,946 bases. Raw data was assembled using Canu v1.6 and single contig was produced in size of 4,096,210 base pairs (Separate attached text file of "*Bacillus subtilis* 3.fasta"). Total number of genes were 4,338 (4,220 coding sequences) and 3,387 annotated genes were found which calculated as 80.26% of total genes.

Lengthy table referenced here

US11602550-20230314-T00002

Please refer to the end of the specification for access instructions.

Example 3

Materials and Methods

Strains

*Bacillus* strains were isolated from home-made Doenjang using Luria Bertani Miller agar (BD, Difco) agar for plating. Representative colonies were picked from plates with the highest dilution still showing colonies. After purification, the strains were stored at −80° C. Before each experiment, the stock culture was cultured in 10 ml LB Miller broth (BD, Difco) in 50 ml falcon sterile tubes for 18 hours at 37° C. in a shaking incubator (rotatory, 120 RPM), the tubes were located in a slope position at an angle of ca80° relative to the vertical line. Then 1% diluted to fresh media (and grown in the same conditions). The culture was then streaked on LB Miller agar (BD, Difco) and incubated for 18 hours. Representative colony was picked and cultured on LB Miller broth (BD, Difco) at 37° C. in a shaking incubator (rotatory, 120 RPM according to the time indicated at each test). Reference strains were obtained from ATCC (American Type Culture Collection) and KACC (Korean Agricultural Culture Collection) and KCTC (Korea, Collection for Type Cultures).

16S rDNA Sequencing

Pure cultures of *Bacillus subtilis* 281 were grown on LB Miller agar (BD Difco) at 37° C. for 24 hours. The plate was sent to Solgent Inc. (Deajun, South Korea) for bi-directional 16S rDNA sequencing using (5'-AGA GTT TGATCMTGG CTC AG-3', SEQ ID NO: 1) and 1492R (5'-TAC GGY TAC CTT GTT ACG ACTT-3' SEQ ID NO: 2) primers by (Reysenbach, Giver et al. 1992). Bi-directional sequencing results were assembled using Codon Code Aligner (Codon Code Corporation, USA) and compared with reference sequences of *Bacillus* species on the GenBank database (www(dot)ncbi(dot)nlm(dot)nihdotgov/Blastn/).

API Test

Specific sugar fermentation pattern was monitored using API 50CHB strips (Biomerieux). The Bacillus strain pellet was prepared using LB Miller agar (BD Difco) at 37° C. for 24 hours and centrifuged 14,000 rpm for 5 min. The pellet was suspended using the preparation media in the kit and applied on different sugars according to the instruction manual.

Hemolysis Test

Bacillus subtilis 281 was grown at 37° C. for 18 hours in LB broth and then streaked onto 5% sheep blood agar (Hanil Komed) and incubated for 24 h at 37° C. Alpha (α) hemolysis was considered as the partial decomposition of the hemoglobin of the red blood cells, beta (β) hemolysis as the complete breakdown of the hemoglobin of the red blood cells observed as a clear zone in the agar plate and gamma (γ) hemolysis as the lack of hemolysis. B. cereus ATCC 27348 was used as a positive control.

Lecithinase Test

Bacillus subtilis 2818 and B. cereus ATCC 27348 (positive control) were grown at 37° C. for 18 hours in LB Miller broth and streaked out onto egg yolk agar. The plates were incubated for 24 h at 37° C. and the formation of a white precipitate around the colonies was considered as positive for lecithinase activity (Hong, Huang et al. 2008, Sorokulova, Pinchuk et al. 2008).

Antibiotic Resistance Test

The basic protocol was followed by CLSI recommendation (Jorgensen and Turnidge 2015). Pure cultures of Bacillus subtilis 281 were cultivated at 37° C. for 18 hours in LB Miller agar. The agar dilution method was used to assess the minimal inhibitory concentration (MIC) of the antibiotics against the strain. A single colony was resuspended in phosphate buffer saline (PBS) 1× and adjusted to 0.01 optical density (OD). Ten microliters ($1 \times 10^5$ CFU/mL) of strain were inoculated on the plates using multipin-inoculator and incubated at 37 C for 24 hours. The strain was considered susceptible when they were inhibited at a concentration for a specific antimicrobial equal or lower than the established cut-off value and resistant bacterial strain when it was not inhibited at a concentration of a specific antimicrobial higher than the established cut-off value according to the parameters established by the European Food Safety Authority (EFSA).

Inhalation Infection Test

The animal study was approved by Handong Global University Ethical committee. For the experiment, 40 mice were divided into four groups comprising negative control, two positive controls infected with pathogenic microorganisms of Streptococcus pneumoniae ATCC49619 and Bacillus cereus ATCC27348 and one group infected with the tested microorganism. Potential probiotic Bacillus subtilis 281 was infected at a dose of $1 \times 10^7$ CFU/mouse with pre-treatment of cyclophosphamide to induce immunocompromised status. The cyclophosphamide was used to derive an immunocompromised animal model in order to monitor more pronounced influence of the infected microorganism as a so called worst case scenario (Kong, Hellermann et al. 2005).

The Bacillus subtilis 281 was grown for 18 hours in LB Miller broth (BD Difco) at 37° C. while S. pneumoniae ATCC49619 was cultured on 5% Sheep blood agar and sub-cultured in Brain Heart Infusion broth (BD Difco) and incubated at 37° C. The bacterial solution was diluted using 1×PBS to $1 \times 10^7$ CFU/mouse. The inoculum concentration was determined by enumeration of cultured bacteria on agar plates.

The animal lung infection model was carried out in 4-week-old female ICR mice (Hyo-chang science). The mice were anesthetized during respiratory infection using 50 μL of bacterial suspension through the intranasal route. After 24 h post infection, 2 mice of each group were selected randomly and sacrificed with diethyl ether for enumeration of viable colonies in lungs. Lungs were extracted and homogenized with phosphate-buffered saline (PBS). Before homogenization, lungs were monitored visually. The homogenized lung samples were diluted and spread on 5% Sheep blood agar to enumerate number of pathogens in the lungs. The plates were incubated for 18 h. The rest of mice were monitored during 1 week to measure their survival rates (Ginsberg, Moldawer et al. 1991).

Efficacy Tests

The agar well diffusion assay was performed to evaluate the antagonistic activity of B. subtilis 281 against the growth of pathogenic bacteria including Escherichia coli ATCC 25922, Pseudomonas aeruginosa ATCC 27853, B. cereus ATCC 27348, Staphylococcus aureus ATCC 6538, Salmonella Typhimurium ATCC 14028 and Listeria innocua ATCC 33090. The antagonistic activity of B. subtilis 281 was also verified against molds such as Alternaria alternata (Fries) Keissler (ATCC® MYA-4642™), Cladosporium sphaerospermum Penzig (ATCC® MYA-4645™) and Penicillium chrysogenum Thom (ATCC® MYA-4644™). Brain Heart Infusion (BHI) Agar was used for the antagonism against pathogenic microorganisms while the Potato Dextrose Agar (PDA) was used for evaluation against molds. Reference pathogens were prepared using BHI broth 37° C. for 18 h while B. subtilis 281 was grown using LB broth at 37° C. for 18 h. Molds were prepared using PDA at 25° C. with 85% HR for 7 days. Mold spores, pathogens and B. subtilis 281 were harvested and resuspended in PBS. Pathogens and B. subtilis 281 was adjusted at optical density of 0.2 and 100 μL of pathogen suspended in PBS was spread on BHI agar plates. The same amount of mold spore suspension was inoculated on PDA. Wells were made in all the plates and 20 μL of B. subtilis 281 suspensions were inoculated in the holes while the BHI plates were incubated at 37° C. for 24 h and PDA plates at 25° C. for 72 h. The inhibition of pathogens and molds were observed as a clear zone around the bacillus strain innoulated wells and 10% hydrogen peroxide served as a positive control.

Complete Genome Sequence

The complete genome sequence of B. subtilis 281 was generated using the PacBio RS platform with single-molecule real-time (SMRT) sequencing at Theragenetex (Seoul, South Korea). Annotations were performed by merging the results obtained from the Rapid Annotations were performed by merging the results obtained from the Papid Annotaions using Subsystems Technology (RAST) server, Glimmer 3.02 modeling software, tRNAscan-SE 2.0, and RNAmmer 1.2. In addition, the contigs were searched against the KEGG, UniProt, and Clusters of Orthologous Groups (COG) databases to annotate the gene description.

Metabolite Analysis

Total protein was extracted from growth media of *B. subtilis* 281 after 18 h at 37° C. incubation to evaluate the metabolites of *B. subtilis* 281. Stock solution was prepared by dissolving 500 g of Trichloroacetic acid (TCA) into 350 mL of distilled water. 1 volume of TCA stock solution was added to 4 volume of *B. subtilis* 281 growth media and incubated at 4° C. for 10 min. Tube was centrifuged at 14,000 rpm for 5 min and supernatant was removed to concentrate protein pellet. The pellet was washed with 200 µL of cold acetone and again concentrated by 14,000 rpm centrifugation for 5 min. This step was repeated for three times and the pellet was sent to be analyzed using LC-LTQ-Orbitrap at Technopark Biocenter (Pohang, South Korea). The raw data was analyzed using UniProt database to match predicted proteins from the growth media of *B. subtilis* 281.

Example 3A

In-Vitro Safety Evaluation of Lecithinase and Hemolysis Activity

*B. subtilis* 281 did not show lecithinase activity observed as the absence of white precipitation around the *Bacillus* colonies and all *B. subtilis* 281 showed negative reaction for hemolysis as well.

TABLE 11

Lecithinase and hemolysis activity of *B. subtilis* 281 and *B. cereus* ATCC 27348.

| Strain | Lecithinase activity | Hemolysis activity |
| --- | --- | --- |
| *B. subtilis* 281 | Negative | Gamma |
| *Bacillus cereus* ATCC 27348 (positive control) | Positive | Beta |

Example 3B

In-Vitro Evaluation of Antibiotic Resistance

The agar dilution was used to evaluate the minimal inhibitory concentration (MIC) of antibiotics. *B. subtilis* 281 was found to be sensitive to erythromycin, gentamicin, tetracycline, streptomycin, vancomycin, chloramphenicol, kanamycin and clindamycin according to the European Food Safety Authority MIC breakpoints for *Bacillus* species. The determined MIC values are clearly below or equal to the EFSA breakpoint values (Table 2).

TABLE 12

Minimum inhibitory concentrations (MIC) of *B. subtilis* 281. Antibiotic resistance test

| | Minimum inhibitory concentration (mg/L) of antibiotics | | | | | | | |
| --- | --- | --- | --- | --- | --- | --- | --- | --- |
| Strain | Ery | Gen | Tet | Str | Van | Chl | Kan | Cli |
| *B. subtilis* 281 | ≤0.125 | ≤2 | ≤0.125 | 8 | 0.25 | ≤4 | ≤4 | 2 |
| EFSA breakpoint | 4 | 4 | 8 | 8 | 4 | 8 | 8 | 4 |

Ery: Erythromycin;
Gen: Gentamicin;
Tet: Tetracycline;
Str: Streptomycin;
Vm: Vancomycin;
Chl: Chloramphenicol;
Kan: Kanamycin;
Cli: Clindamycin.

Example 3C

Respiratory Tract Infection Test

Figure 9:
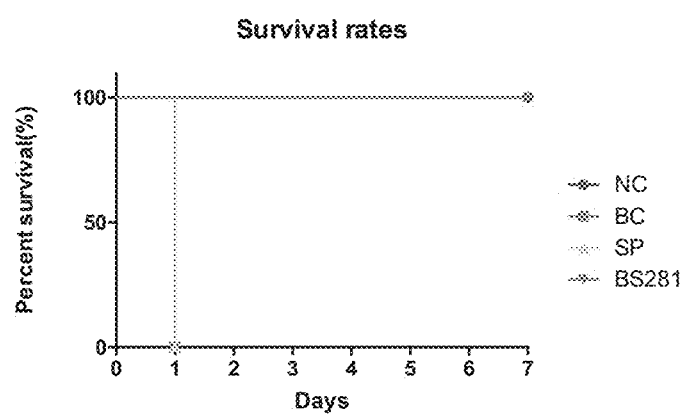
FIG. 9 is a graph showing the survival rates of mice after respiratory tract infection (NC: negative control, BC: *B. cereus*, SP: *S. pneumoniae*, BS281: *B. subtilis* 281).
Figure 10:
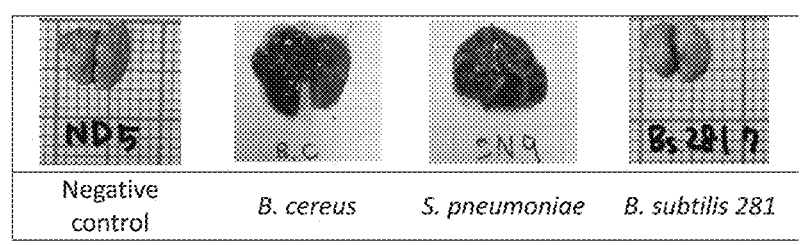
FIG. 10 is a photograph showing the appearance of lungs in each group described in FIG. 9.

The survival rate after respiratory tract infection of *B. subtilis* 281 was 100% while the positive control of pathogenic bacteria infected groups including *S. pneumoniae* and *B. cereus* showed 100% mortality after 24 hours (FIG. 9). Lung pictures were taken and showed strong damage in pathogen infected positive groups while lung of *B. subtilis* 281 infected groups showed similar lung status as negative control group (FIG. 10) and any colony of *Bacillus* was found from the homogenized lung of *B. subtilis* 281 infected group (data not shown).

Example 3D

Efficacy Tests

Figure 11:
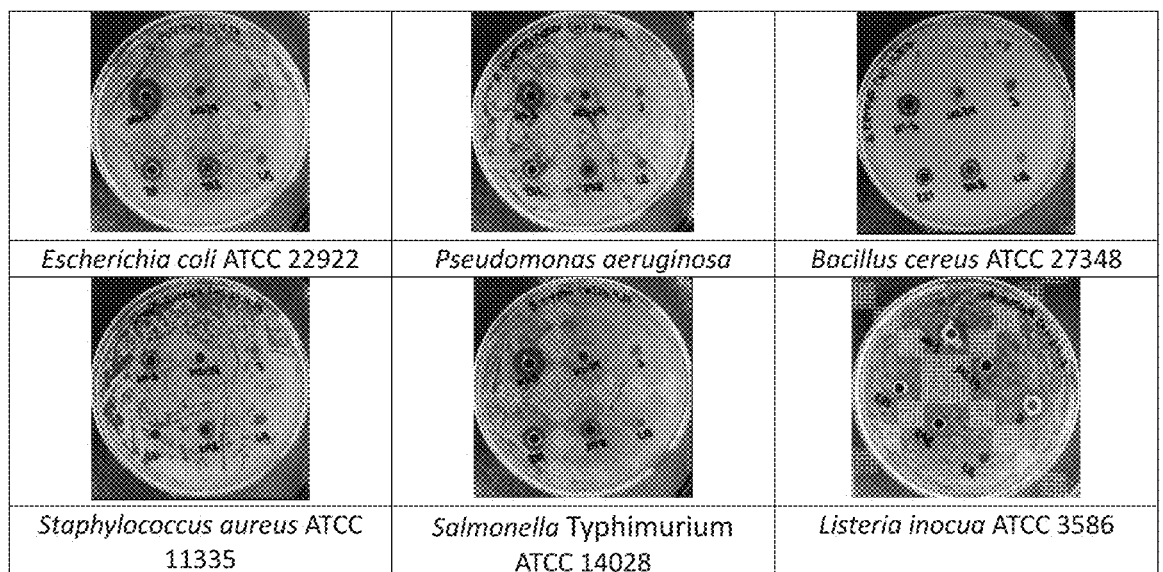
FIG. 11 is a photograph showing antagonism of pathogenic bacteria by *B. subtilis* 281.

The antagonism test results of *B. subtilis* 281 showed inhibited growth of *E. coli* ATCC 22922, *P. aeruginosa, B. cereus* ATCC 27348 and *S. Typhimurium* ATCC 14028 at different degrees (FIG. 11 and Table 13).

TABLE 13

Antagonistic activity of *Bacillus subtilis* 281 against pathogens.

| Pathogens | *B. subtilis* 281 |
| --- | --- |
| *Escherichia coli* ATCC 25922 | 2 |
| *Pseudomonas aeruginosa* ATCC 27853 | 1 |
| *Bacillus cereus* ATCC 27348 | 1 |
| *Staphylococcus aureus* ATCC 6538 | NA |
| *Salmonella Typhimurium* ATCC 14028 | 2 |
| *Listeria innocua* ATCC 33090 | NA |

NA: No antagonism was observed

Figure 12:
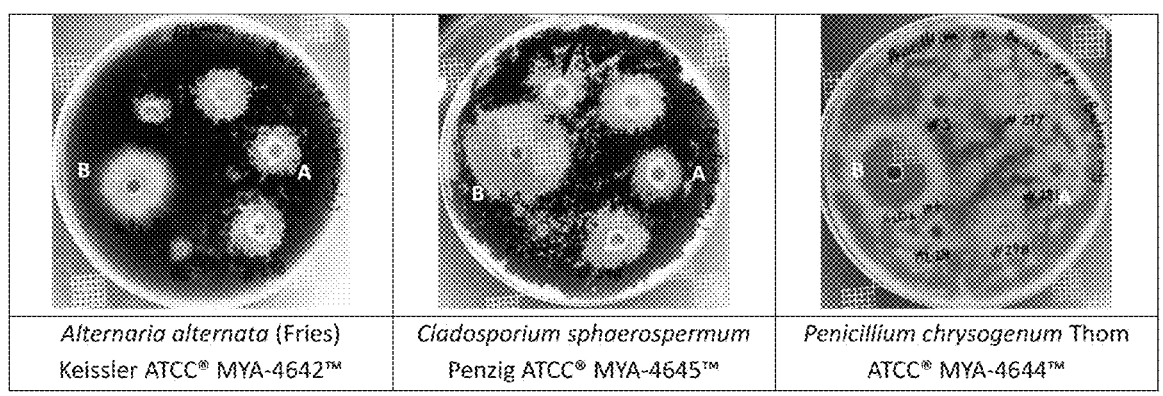
FIG. 12 is a photographic representation of results for the antagonism of test molds using *B. subtilis* 281 (A) and 10% hydrogen peroxide (B) as a positive control.
Figure 13:
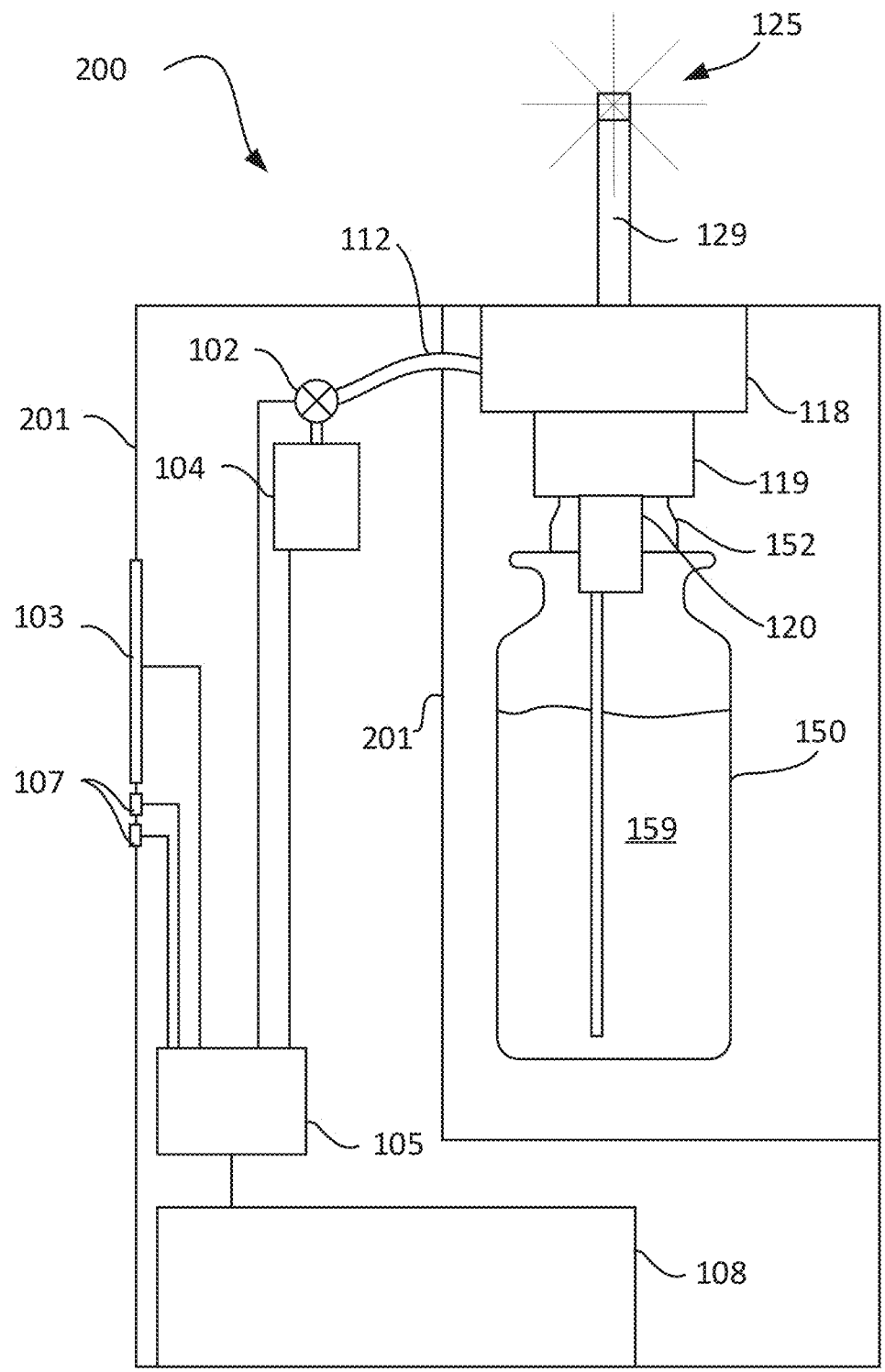
FIG. 13 is a simplified schematic drawing of an example aerosol dispensing device in accordance with some example embodiments.
Figures 14A, 14B:
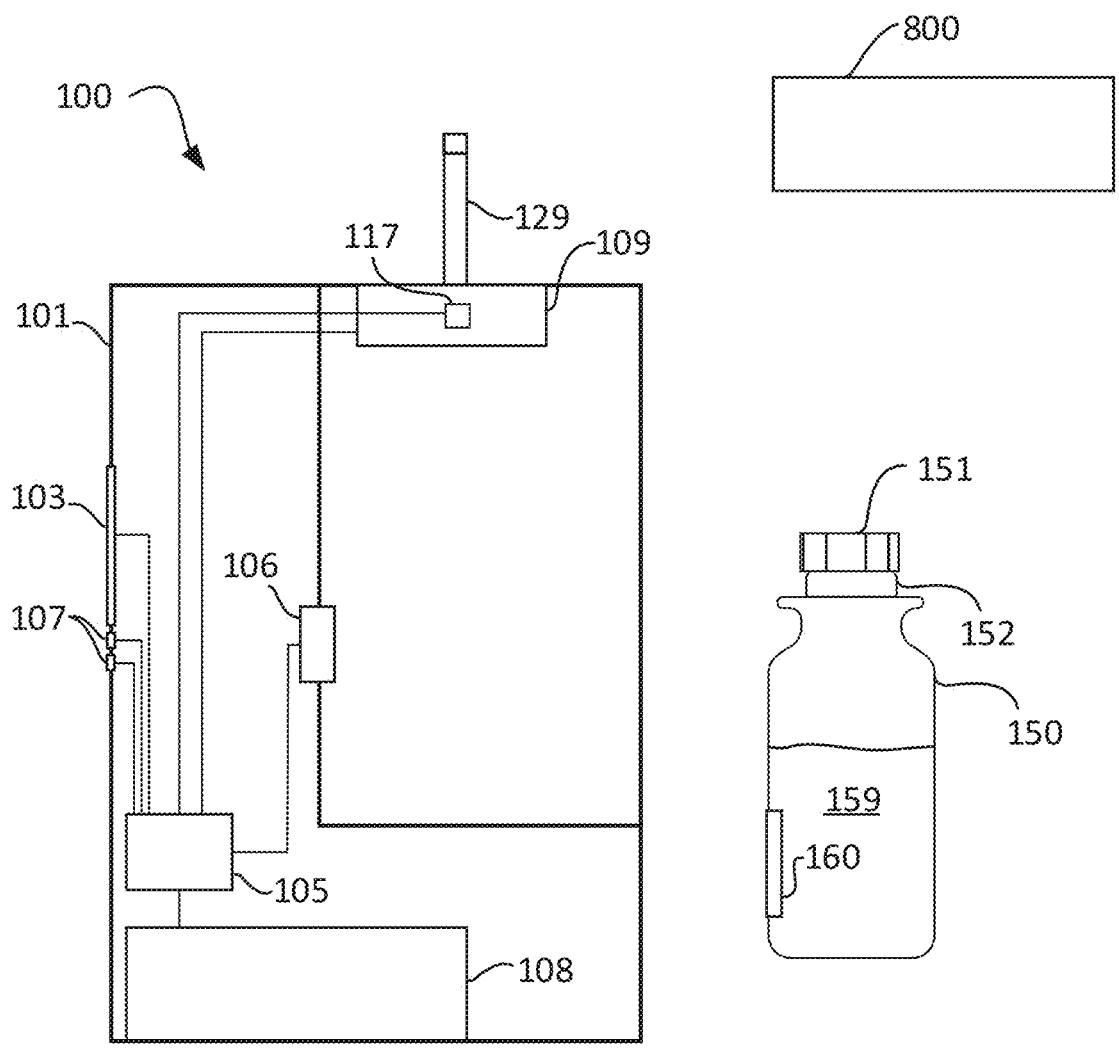
FIGS. 14A and 14B are simplified schematic drawings of an example aerosol dispensing device and an example replaceable cartridge respectively in accordance with some example embodiments.
Figure 15:
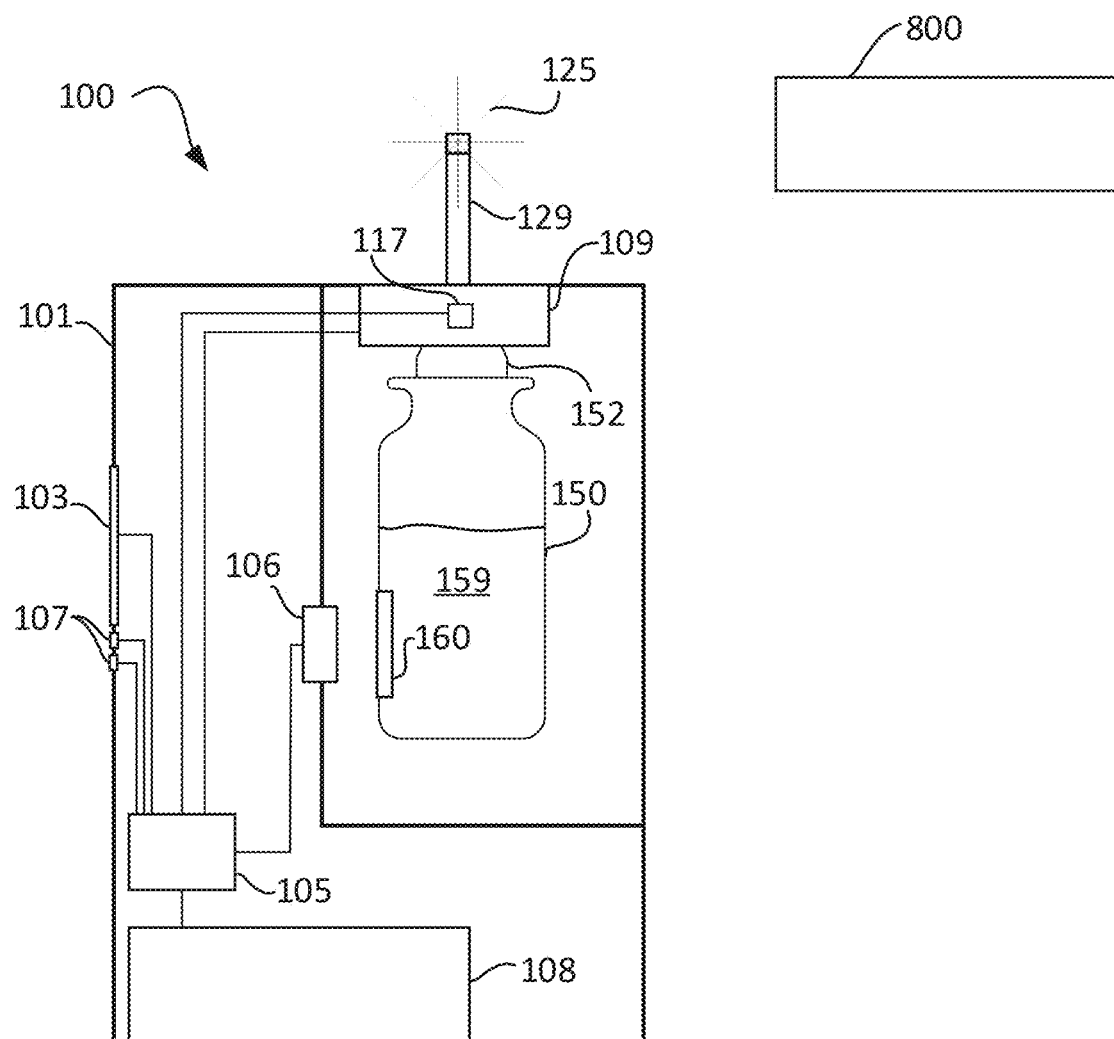
FIG. 15 is a simplified schematic drawing of an example replaceable cartridge installed in an example aerosol dispensing device in accordance with some example embodiments.
Figure 16:
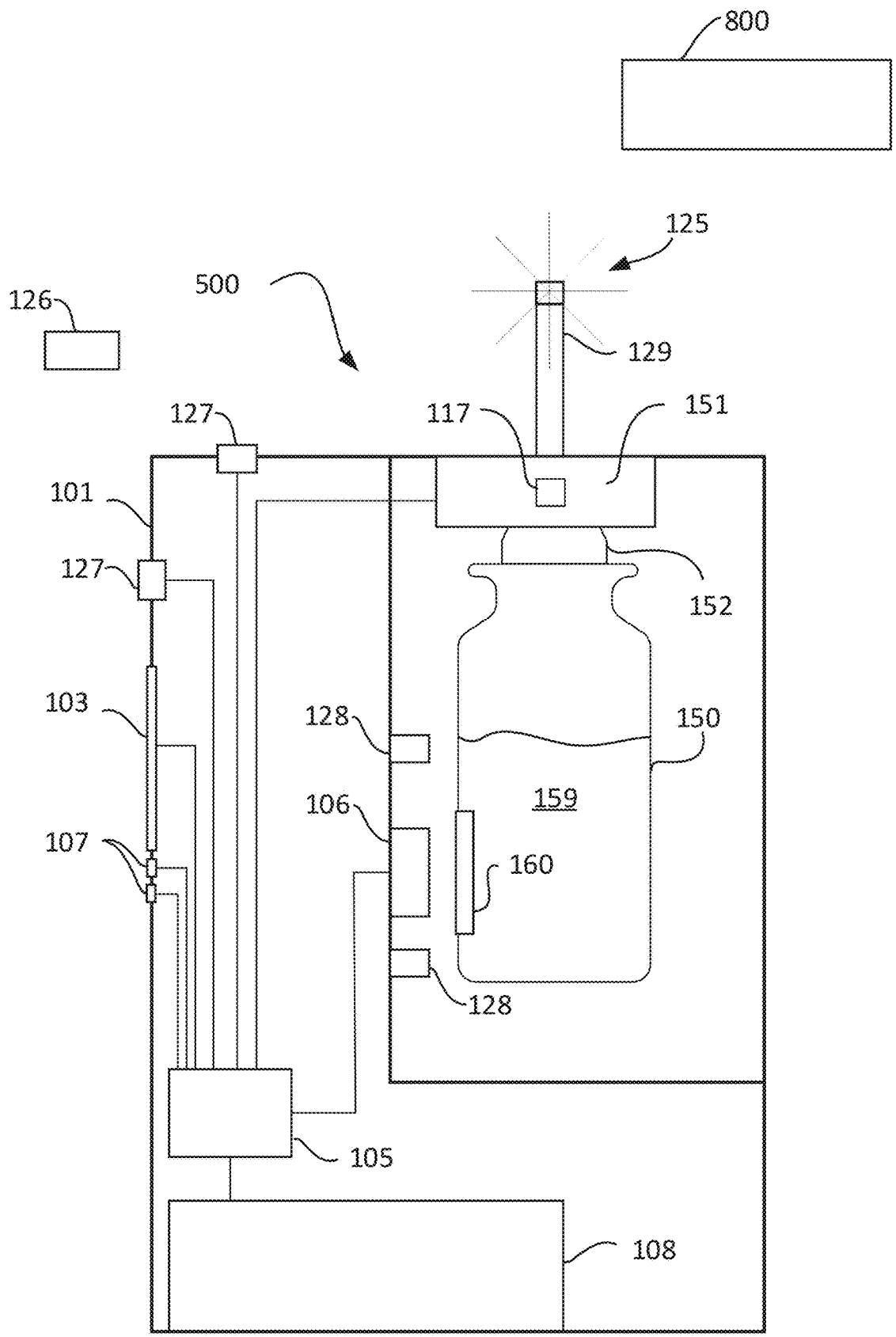
FIG. 16 is simplified schematic drawing of an example aerosol dispensing device including one or more sensors in accordance with some example embodiments.

*B. subtilis* 281 antagonism tests against mold showed positive antagonism against *Alternaria alternata* (Fries) Keissler (ATCC® MYA-4642™) and *Cladosporium sphaerospermum* Penzig (ATCC® MYA-4645™) at variable levels (Table 4). The inhibition of the mold growth is evidently expressed as a clear zone around the wells inoculated with the B. subtilis 281 (FIG. 12). Penicillium chrysogenum Thom (ATCC® MYA-4644™) was not inhibited at all for any of the strains used on this experiment, however the mycelium color around the well inoculated with B. subtilis 281 showed and slightly decrease in the intensity (data not shown) from green to white.

TABLE 14

Antifungal activity of Bacillus subtilis 281 against molds.

| Strain | Inhibition zone (mm) | | |
|---|---|---|---|
| | Alternaria alternata (Fries) Keissler (ATCC MYA-4642) | Cladosporium sphaerospermum Penzig (ATCC MYA-4645) | Penicillium chrysogenum Thom (ATCC MYA-4644) |
| Bacillus subtilis 281 | 5 | 5 | NA |
| Hydrogen peroxide 10% | 8 | 12 | 10 |

NA: No antagonism was observed

Example 3E

Taxonomic Identification

The identity of the strain was confirmed as B. subtilis according to the National Center for Biotechnology Information (NCBI) database. API results were monitored for further identification of physiological characteristics.

Example 3F

Complete Genome Sequence

Single run of PacBio provided total number of 99,139 reads which comprises in total of 917,648,089 bases. Raw data was assembled using Canu v1.6 and single contig was produced in size of 4,089,095 base pairs (Separately attached text file of "Bacillus subtilis 281.fasta"). Total number of genes were 4,365 (4,248 coding sequences) and 3,399 annotated genes were found which calculated as 80.01% of total genes (Table 5).

Lengthy table referenced here

US11602550-20230314-T00003

Please refer to the end of the specification for access instructions.

Example 4

Materials and Methods

As described above.

Example 4A

In-Vitro Safety Evaluation of Lecithinase and Hemolysis Activity

B. subtilis 3, B. subtilis 281 and B. amyloliquefaciens 298 did not show lecithinase activity observed as the absence of withe precipitated around the Bacillus colonies and all strains showed negative reaction for hemolysis as well.

TABLE 16

Lecithinase and hemolysis activity of B. subtilis strain 3, B. subtilis 281 and B. amyloliquefaciens 298 and B. cereus ATCC 27348.

| Strain | Lecithinase activity | Hemolysis activity |
|---|---|---|
| Bacillus subtilis 3 | Negative | Gamma |
| Bacillus subtilis 281 | Negative | Gamma |
| Bacillus amyloliquefaciens 298 | Negative | Gamma |
| Bacillus cereus ATCC 27348 (positive control) | Positive | Beta |

Example 4B

In-Vitro Evaluation of Antibiotic Resistance

An agar dilution was used to evaluate the minimal inhibitory concentration (MIC) of antibiotics. B. subtilis 3, B. subtilis 281 and B. amyloliquefaciens 298 were found to be sensitive to erythromycin, gentamicin, tetracycline, streptomycin, vancomycin, chloramphenicol, kanamycin and clindamycin according to the European Food Safety Authority MIC breakpoints for Bacillus species. The determined MIC values are clearly below or equal to the EFSA breakpoint values (Table 17).

TABLE 17

Minimum inhibitory concentrations (MIC) of B. subtilis strains number 3, B. subtilis strain 3, B. subtilis 281 and B. amyloliquefaciens 298.

Antibiotic resistance test

| Strain | Minimum inhibitory concentration (mg/L) of antibiotics | | | | | | | |
|---|---|---|---|---|---|---|---|---|
| | Ery | Gen | Tet | Str | Van | Chl | Kan | Cli |
| B. subtilis 3 | ≤2 | ≤2 | ≤4 | 8 | ≤2 | ≤4 | ≤4 | 4 |
| B. subtilis 281 | ≤0.125 | ≤2 | ≤0.125 | 8 | 0.25 | ≤4 | ≤4 | 2 |

TABLE 17-continued

Minimum inhibitory concentrations (MIC) of *B. subtilis* strains number 3,
*B. subtilis* strain 3, *B. subtilis* 281 and *B. amyloliquefaciens* 298.
Antibiotic resistance test

| Strain | Minimum inhibitory concentration (mg/L) of antibiotics | | | | | | | |
|---|---|---|---|---|---|---|---|---|
| | Ery | Gen | Tet | Str | Van | Chl | Kan | Cli |
| *B. amyloliquefaciens* 298 | ≤0.125 | ≤2 | ≤0.125 | 8 | 0.25 | ≤4 | ≤4 | 0.5 |
| EFSA breakpoint | 4 | 4 | 8 | 8 | 4 | 8 | 8 | 4 |

Ery: Erythromycin;
Gen: Gentamicin;
Tet: Tetracycline;
Str: Streptomycin;
Vm: Vancomycin;
Chl: Chloramphenicol;
Kan: Kanamycin;
Cli: Clindamycin.

Example 4C

Respiratory Tract Infection Test

Figure 17:
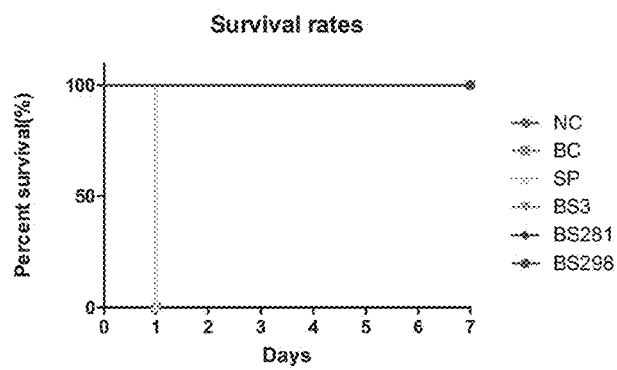
FIG. 17 is a graph showing the survival rates of mice after respiratory tract infection (NC: negative control, BC: *B. cereus*, SP: *S. pneumoniae*, BS3: *B. subtilis* 3, BS281: *B. subtilis* 281, BS298: *B. amyloliquefaciens* 298).
Figure 18:
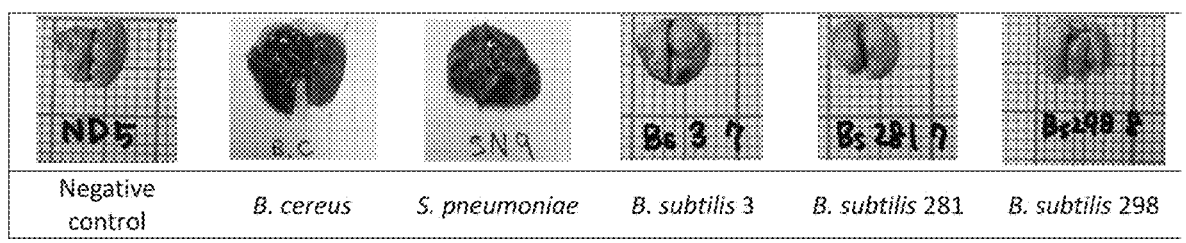
FIG. 18 is a photograph showing the appearance of lungs in each group described in FIG. 17.

The survival rate after respiratory tract infection of *B. subtilis* 3, *B. subtilis* 281 and *B. amyloliquefaiciens* 298 was 100% while the positive control of pathogenic bacteria infected groups including *S. pneumoniae* and *B. cereus* showed 100% mortality after 24 hours (FIG. 17). All lung pictures were taken and showed strong damage in pathogen infected positive groups while lung of *B. subtilis* 3, *B. subtilis* 281 and *B. amyloliquefaiciens* 298 infected groups showed similar lung status as negative control group (FIG. 18) and any colony forming units of *Bacillus* strains were found from the homogenized lung of *B. subtilis* 3, *B. subtilis* 281 and *B. amyloliquefaiciens* 298 infected groups (data not shown).

Example 4D

Efficacy Tests

Figure 19:
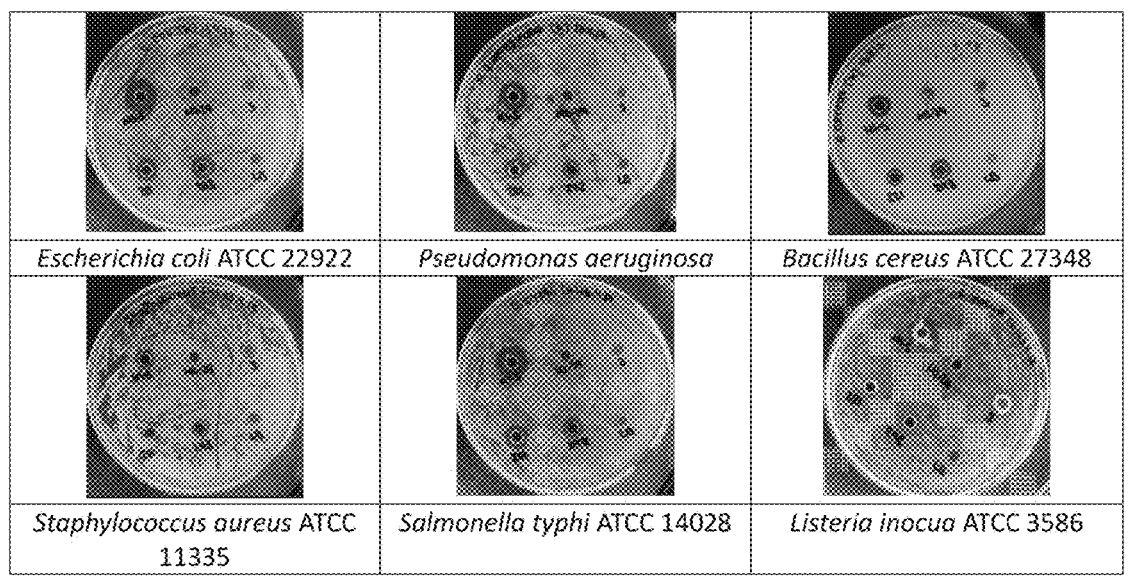
FIG. 19 is a photograph showing antagonism of pathogenic bacteria by *B. subtilis* 3, *B. subtilis* 281 and *B. amyloliquefaiciens* 298.

The antagonism test results of *B. subtilis* 3, *B. subtilis* 281 and *B. amyloliquefaiciens* 298 against pathogenic bacteria indicate that *B. subtilis* 3 reduce the growth of *E. coli* ATCC 22922, *S. aureus* ATCC 11335 and *L. inocua* ATCC 3586 at various levels. Regarding to *B. subtilis* 281 and *B. amyloliquefaiciens* 298, they seem to antagonize the growing of *E. coli* ATCC 22922, *P. aeruginosa*, *B. cereus* ATCC 27348 and *S. typhi* ATCC 14028 also at different degrees. In addition, *B. amyloliquefaiciens* 298 has also the ability of slightly reduce the growth of *S. aureus* ATCC 11335. In general, *B. amyloliquefaiciens* 298 could be more effective against pathogenic bacteria than the other two strains (FIG. 19).

TABLE 18

Antagonistic activity of *Bacillus subtilis* strains against pathogens.

| *Bacillus* strains | Pathogens Inhibition zone (mm) | | |
|---|---|---|---|
| | *B. subtilis* 3 | *B. subtilis* 281 | *B. amyloliquefaiciens* 298 |
| *Escherichia coli* ATCC 22922 | 1 | 2 | 2 |
| *Pseudomonas aeruginosa* | NA | 1 | 1 |
| *Bacillus cereus* ATCC 27348 | NA | 1 | 2 |
| *Staphylococcus aureus* ATCC 11335 | 1 | NA | 1 |
| *Salmonella typhi* ATCC 14028 | NA | 2 | 2 |
| *Listeria inocua* ATCC 3586 | 2 | NA | NA |

NA: No antagonism was observed

Figure 20:
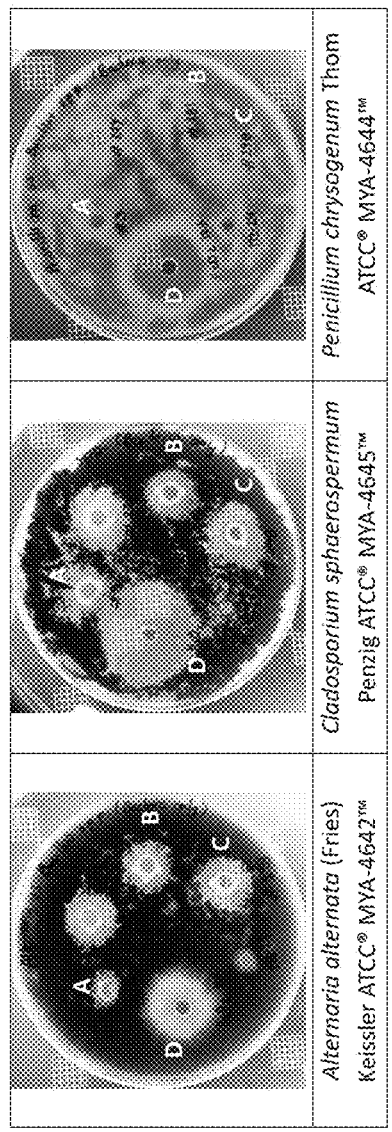
FIG. 20 is a photographic representation of results for the antagonism of test molds using *B. subtilis* strains 3 (A), *B. subtilis* 281 (B) and *B. amyloliquefaciens* 298 (C) and 10% hydrogen peroxide (D) as a positive control.

*B. subtilis* 3, *B. subtilis* 281 and *B. amyloliquefaiciens* 298 antagonism against mold indicate the strain 3, 281 and 298 has antagonism against *Alternaria alternata* (Fries) Keissler (ATCC® MYA-4642™) and *Cladosporium sphaerospermum* Penzig (ATCC® MYA-4645™) at variable level (Table 19). The inhibition of the mold growth is evidently expressed as a clear zone around the wells inoculated with the *B. subtilis* 3, *B. subtilis* 281 and *B. amyloliquefaiciens* 298 (FIG. 20). *Penicillium chrysogenum* Thom (ATCC® MYA-4644™) was not inhibited at all for any of the strains used on this experiment, however the mycelium color around the well inoculated with strains number 281 and 298 show and slightly decrease in the intensity (data not shown) from green to white.

TABLE 19

Antifungal activity of *Bacillus subtilis* strains against molds.

| Strain | Inhibition zone (mm) | | |
|---|---|---|---|
| | *Alternaria alternata* (Fries) Keissler (ATCC MYA-4642) | *Cladosporium sphaerospermum* Penzig (ATCC MYA-4645) | *Penicillium chrysogenum* Thom (ATCC MYA-4644) |
| *Bacillus subtilis* 3 | 2 | 4 | NA |

TABLE 19-continued

Antifungal activity of *Bacillus subtilis* strains against molds.

| | Inhibition zone (mm) | | |
|---|---|---|---|
| Strain | *Alternaria alternata* (Fries) Keissler (ATCC MYA-4642) | *Cladosporium sphaerospermum* Penzig (ATCC MYA-4645) | *Penicillium chrysogenum* Thom (ATCC MYA-4644) |
| *Bacillus subtilis* 281 | 5 | 5 | NA |
| *Bacillus amyloliquefaciens* 298 | 6 | 6 | NA |
| Hydrogen peroxide 10% | 8 | 12 | 10 |

NA: No antagonism was observed

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

REFERENCES

1. Cho, K.-M. (2008). "Characterization of potential probiotics *Bacillus subtilis* CS90 from soybean paste (doenjang) and its antimicrobial activity against food-borne pathogens." Journal of Applied Biological Chemistry 51(6): 285-291.
2. FRANZ, C. M., A. HUMMEL and W. H. HOLZAPFEL (2005). "Problems related to the safety assessment of lactic acid bacteria starter cultures and probiotics." Mitteilungen aus Lebensmitteluntersuchung and Hygiene 96(1): 39-65.
3. Ginsberg, H. S., L. L. Moldawer, P. B. Sehgal, M. Redington, P. L. Kilian, R. M. Chanock and G. A. Prince (1991). "A mouse model for investigating the molecular pathogenesis of adenovirus pneumonia." Proceedings of the National Academy of Sciences 88(5): 1651-1655.
4. Holzapfel, W. H. and U. Schillinger (2002). "Introduction to pre- and probiotics." Food Research International 35(2): 109-116.
5. Hong, H., J. M. Huang, R. Khaneja, L. Hiep, M. Urdaci and S. Cutting (2008). "The safety of *Bacillus subtilis* and *Bacillus indicus* as food probiotics." Journal of applied microbiology 105(2): 510-520.
6. Jeon, H. H., J. Y. Jung, B.-H. Chun, M.-D. Kim, S. Y. Baek, J. Y. Moon, S.-H. Yeo and C. O. Jeon (2016). "Screening and characterization of potential *Bacillus* starter cultures for fermenting low salt soybean paste (doenjang)." J. Microbiol. Biotechnol 26(4): 666-674.
7. Jorgensen, J. H. and J. D. Turnidge (2015). Susceptibility test methods: dilution and disk diffusion methods. Manual of Clinical Microbiology, Eleventh Edition, American Society of Microbiology: 1253-1273.
8. Kong, X., G. R. Hellermann, G. Patton, M. Kumar, A. Behera, T. S. Randall, J. Zhang, R. F. Lockey and S. S. Mohapatra (2005). "An immunocompromised BALB/c mouse model for respiratory syncytial virus infection." Virology journal 2(1): 3.
9. Leuschner, R. G., T. P. Robinson, M. Hugas, P. S. Cocconcelli, F. Richard-Forget, G. Klein, T. R. Licht, C. Nguyen-The, A. Querol and M. Richardson (2010). "Qualified presumption of safety (QPS): a generic risk assessment approach for biological agents notified to the European Food Safety Authority (EFSA)." Trends in Food Science & Technology 21(9): 425-435.
10. Reysenbach, A.-L., L. J. Giver, G. S. Wickham and N. R. Pace (1992). "Differential amplification of rRNA genes by polymerase chain reaction." Applied and Environmental Microbiology 58(10): 3417-3418.
11. Sorokulova, I. B., I. V. Pinchuk, M. Denayrolles, I. G. Osipova, J. M. Huang, S. M. Cutting and M. C. Urdaci (2008). "The safety of two *Bacillus* probiotic strains for human use." Digestive diseases and sciences 53(4): 954-963.
12. Wang, L.-T., F.-L. Lee, C.-J. Tai and H. Kasai (2007). "Comparison of gyrB gene sequences, 16S rRNA gene sequences and DNA-DNA hybridization in the *Bacillus subtilis* group." International Journal of Systematic and Evolutionary Microbiology 57(8): 1846-1850.
13. Xu, S. J., D. H. Park, J.-Y. Kim and B.-S. Kim (2016). "Biological control of gray mold and growth promotion of tomato using *Bacillus* spp. isolated from soil." Tropical Plant Pathology 41(3): 169-176.

LENGTHY TABLES

The patent contains a lengthy table section. A copy of the table is available in electronic form from the USPTO web site (https://seqdata.uspto.gov/?pageRequest=docDetail&DocID=US11602550B2). An electronic copy of the table will also be available from the USPTO upon request and payment of the fee set forth in 37 CFR 1.19(b)(3).

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11602550B2). An electronic copy of the "Sequence Listing" will also be available from the USPTO upon request and payment of the fee set forth in 37 CFR 1.19(b)(3).

What is claimed is:

1. A composition comprising *Bacillus subtilis* 281, *Bacillus subtilis* 3, *Bacillus amyloliquefaciens* 298, wherein the composition does not comprise more than 5 different species of microbes, wherein:
   a sample of *Bacillus subtilis* 281, has been deposited as KCTC 13468BP at the Korean Collection for Type Cultures;
   a sample of *Bacillus subtilis* 3, has been deposited as KCTC 13467BP at the Korean Collection for Type Cultures; and
   a sample of *Bacillus amyloliquefaciens* 298, has been deposited as KCTC 13469BP at the Korean Collection for Type Cultures.

2. The composition of claim 1, wherein said bacterial strain is attached to a solid support.

3. The composition of claim 1, wherein said bacterial strain is soluble.

4. The composition of claim 1, wherein said *Bacillus subtilis* 281, *Bacillus subtilis* 3 and *Bacillus amyloliquefaciens* 298 are present in a ratio of about 1:1:1.

* * * * *